US010005756B2

(12) United States Patent
Heinrich et al.

(10) Patent No.: US 10,005,756 B2
(45) Date of Patent: Jun. 26, 2018

(54) PYRROLIDINONE DERIVATIVES AS METAP-2 INHIBITORS

(71) Applicant: Merck Patent GmbH, Darmstadt (DE)

(72) Inventors: Timo Heinrich, Gross-Umstadt (DE); Frank Zenke, Darmstadt (DE); Felix Rohdich, Worfelden (DE); Manja Friese-Hamim, Moerfelden-Walldorf (DE); Diane Hahn, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days. days.

(21) Appl. No.: 15/501,494

(22) PCT Filed: Jul. 10, 2015

(86) PCT No.: PCT/EP2015/001421
§ 371 (c)(1),
(2) Date: Feb. 3, 2017

(87) PCT Pub. No.: WO2016/020031
PCT Pub. Date: Feb. 11, 2016

(65) Prior Publication Data
US 2017/0226080 A1 Aug. 10, 2017

(30) Foreign Application Priority Data
Aug. 4, 2014 (EP) .................... 14002720

(51) Int. Cl.
C07D 471/04 (2006.01)
A61K 31/437 (2006.01)
C07D 401/04 (2006.01)
A61K 31/4025 (2006.01)
A61K 31/00 (2006.01)
A61K 31/4015 (2006.01)
C07D 207/277 (2006.01)
C07D 401/06 (2006.01)
C07D 401/12 (2006.01)
C07D 403/04 (2006.01)
C07D 403/12 (2006.01)
C07D 405/04 (2006.01)
C07D 405/12 (2006.01)
C07D 405/14 (2006.01)
C07D 409/12 (2006.01)
C07D 413/10 (2006.01)
C07D 413/12 (2006.01)

(52) U.S. Cl.
CPC ............ *C07D 401/04* (2013.01); *A61K 31/00* (2013.01); *A61K 31/4015* (2013.01); *A61K 31/4025* (2013.01); *C07D 207/277* (2013.01); *C07D 401/06* (2013.01); *C07D 401/12* (2013.01); *C07D 403/04* (2013.01); *C07D 403/12* (2013.01); *C07D 405/04* (2013.01); *C07D 405/12* (2013.01); *C07D 405/14* (2013.01); *C07D 409/12* (2013.01); *C07D 413/10* (2013.01); *C07D 413/12* (2013.01); *C07D 471/04* (2013.01)

(58) Field of Classification Search
None
See application file for complete search history.

(56) References Cited

U.S. PATENT DOCUMENTS

| 8,895,535 B2 | 11/2014 | Heinrich et al. |
| 2013/0296274 A1 | 11/2013 | Heinrich et al. |
| 2015/0031670 A1 | 1/2015 | Heinrich et al. |

FOREIGN PATENT DOCUMENTS

| DE | 102010048374 A1 | 4/2012 | | |
| DE | 102012006884 A1 | 10/2013 | | |
| WO | WO 2012/048775 | * 4/2012 | ......... | C07D 207/277 |
| WO | WO 2013/149704 | * 10/2013 | ......... | C07D 223/08 |

OTHER PUBLICATIONS

International Search Report dated Sep. 18, 2015 issued in corresponding PCT/EP2015/001421 application (3 pages).
Written Opinion of the International Searching Authority dated Sep. 18, 2015 issued in corresponding PCT/EP2015/001421 application (4 pages).

* cited by examiner

*Primary Examiner* — Alicia L Otton
(74) *Attorney, Agent, or Firm* — Millen White Zelano and Branigan, PC

(57) ABSTRACT

Compounds according to Claim 1, are inhibitors of methionine aminopeptidase and can be employed for the treatment of tumors.

8 Claims, No Drawings

PYRROLIDINONE DERIVATIVES AS METAP-2 INHIBITORS

The invention relates to compounds selected from the group

| Compound No. | Structure/name |
|---|---|
| "A1" | 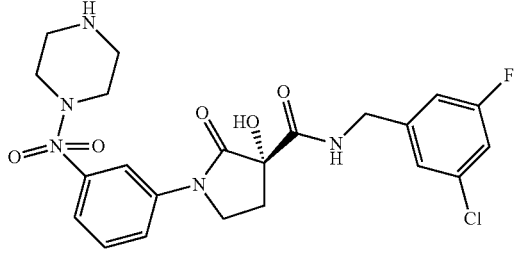<br>(S)-3-Hydroxy-2-oxo-1-[3-(piperazine-1-sulfonyl)-phenyl]-pyrrolidine-3-carboxylic acid 3-chloro-5-fluoro-benzylamide |
| "A2" | 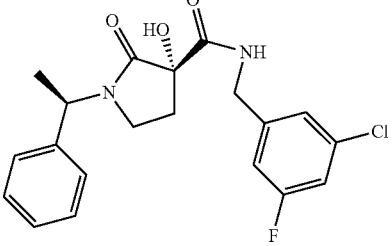<br>(S)-3-Hydroxy-2-oxo-1-((R)-1-phenyl-ethyl)-pyrrolidine-3-carboxylic acid 3-chloro-5-fluoro-benzylamide |
| "A3" | 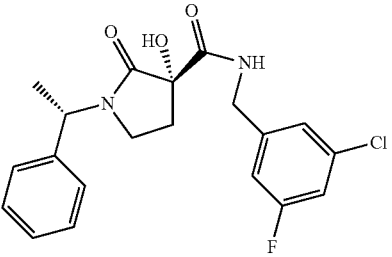<br>(S)-3-Hydroxy-2-oxo-1-((S)-1-phenyl-ethyl)-pyrrolidine-3-carboxylic acid 3-chloro-5-fluoro-benzylamide |
| "A4" | 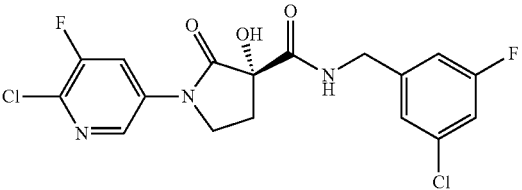<br>(S)-1-(6-Chloro-5-fluoro-pyridin-3-yl)-3-hydroxy-2-oxo-pyrrolidine-3-carboxylic acid 3-chloro-5-fluoro-benzylamide |

-continued

| Compound No. | Structure/name |
|---|---|
| "A5" | 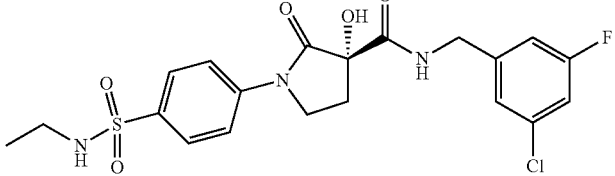<br>(S)-1-(4-Ethylsulfamoyl-phenyl)-3-hydroxy-2-oxo-pyrrolidine-3-carboxylic acid 3-chloro-5-fluoro-benzylamide |
| "A6" | 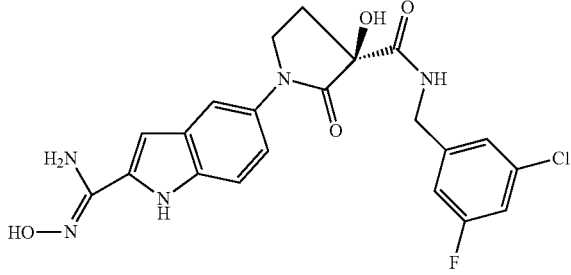<br>(S)-3-Hydroxy-1-[2-(N-hydroxycarbamimidoyl)-1H-indol-5-yl]-2-oxo-pyrrolidine-3-carboxylic acid 3-chloro-5-fluoro-benzylamide |
| "A7" | 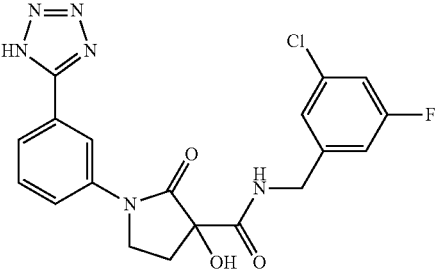<br>3-Hydroxy-2-oxo-1-[3-(1H-tetrazol-5-yl)-phenyl]-pyrrolidine-3-carboxylic acid 3-chloro-5-fluoro-benzylamide |
| "A8" | 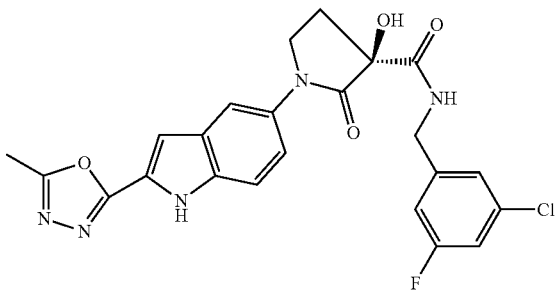<br>(S)-3-Hydroxy-1-[2-(5-methyl-[1,3,4]oxadiazol-2-yl)-1H-indol-5-yl]-2-oxo-pyrrolidine-3-carboxylic acid 3-chloro-5-fluoro-benzylamide |

| Compound No. | Structure/name |
|---|---|
| "A9" | 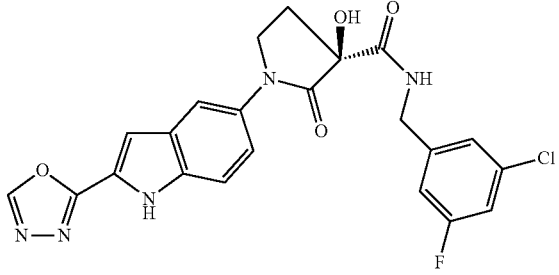
(S)-3-Hydroxy-1-(2-[1,3,4]oxadiazol-2-yl-1H-indol-5-yl)-2-oxo-pyrrolidine-3-carboxylic acid 3-chloro-5-fluoro-benzylamide |
| "A10" | 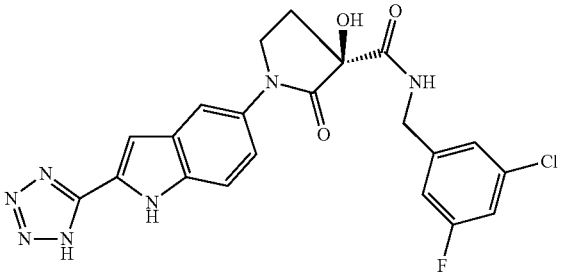
(S)-3-Hydroxy-2-oxo-1-[2-(1H-tetrazol-5-yl)-1H-indol-5-yl]-pyrrolidine-3-carboxylic acid 3-chloro-5-fluoro-benzylamide |
| "A11" | 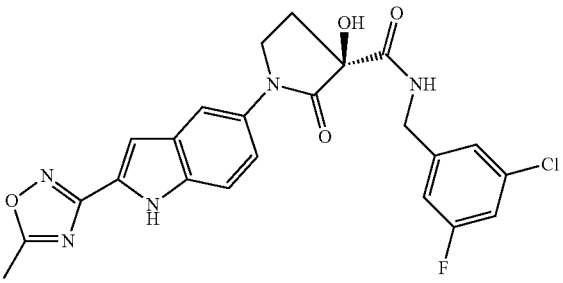
(S)-3-Hydroxy-1-[2-(5-methyl-[1,2,4]oxadiazol-3-yl)-1H-indol-5-yl]-2-oxo-pyrrolidine-3-carboxylic acid 3-chloro-5-fluoro-benzylamide |
| "A12" | 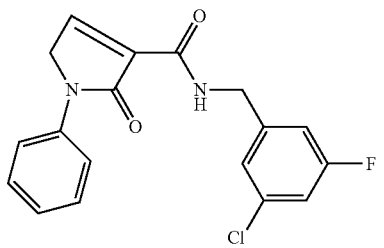
2-Oxo-1-phenyl-2,5-dihydro-1H-pyrrole-3-carboxylic acid 3-chloro-5-fluoro-benzylamide |

-continued

| Compound No. | Structure/name |
|---|---|
| "A13" | 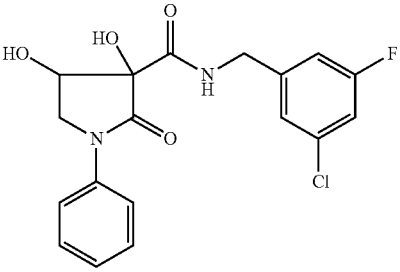<br>3,4-Dihydroxy-2-oxo-1-phenyl-pyrrolidine-3-carboxylic acid 3-chloro-5-fluoro-benzylamide |
| "A14" | 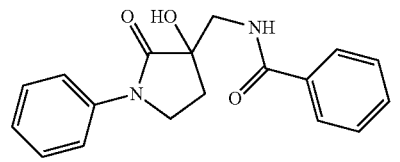<br>N-(3-Hydroxy-2-oxo-1-phenyl-pyrrolidin-3-ylmethyl)-benzamide |
| "A15" | 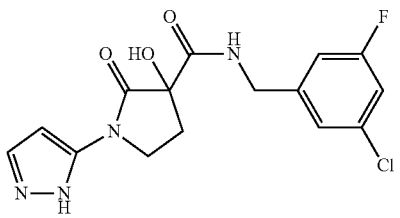<br>3-Hydroxy-2-oxo-1-(2H-pyrazol-3-yl)-pyrrolidine-3-carboxylic acid 3-chloro-5-fluoro-benzylamide |
| "A16" | 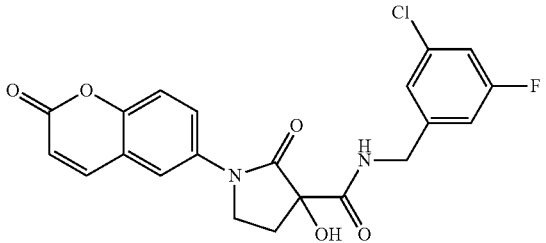<br>3-Hydroxy-2-oxo-1-(2-oxo-2H-chromen-6-yl)-pyrrolidine-3-carboxylic acid 3-chloro-5-fluoro-benzylamide |
| "A17" | 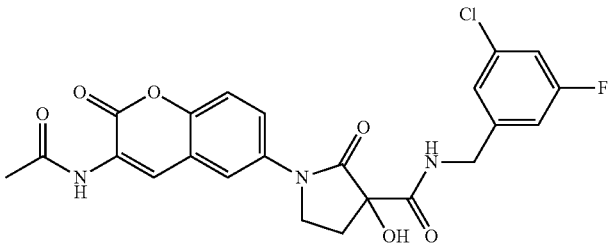<br>1-(3-Acetylamino-2-oxo-2H-chromen-6-yl)-3-hydroxy-2-oxo-pyrrolidine-3-carboxylic acid 3-chloro-5-fluoro-benzylamide |

| Compound No. | Structure/name |
|---|---|
| "A18" | 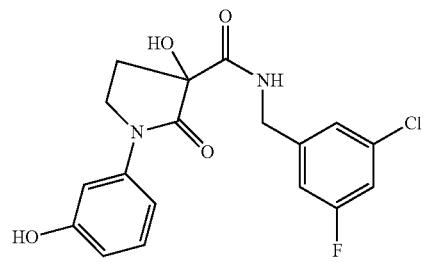<br>3-Hydroxy-1-(3-hydroxy-phenyl)-2-oxo-pyrrolidine-3-carboxylic acid 3-chloro-5-fluoro-benzylamide |
| "A19" | 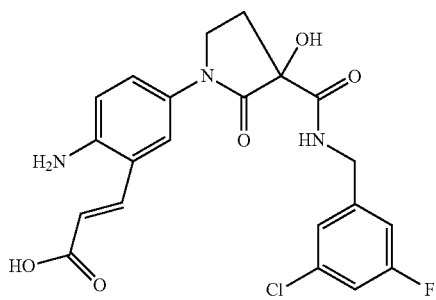<br>(E)-3-{2-Amino-5-[3-(3-chloro-5-fluoro-benzylcarbamoyl)-3-hydroxy-2-oxo-pyrrolidin-1-yl]-phenyl}-acrylic acid |
| "A20" | 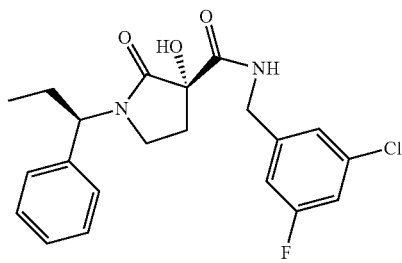<br>(S)-3-Hydroxy-2-oxo-1-((R)-1-phenyl-propyl)-pyrrolidine-3-carboxylic acid 3-chloro-5-fluoro-benzylamide |
| "A21" | 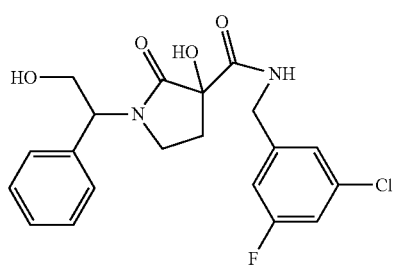<br>3-Hydroxy-1-(2-hydroxy-1-phenyl-ethyl)-2-oxo-pyrrolidine-3-carboxylic acid 3-chloro-5-fluoro-benzylamide |

| Compound No. | Structure/name |
|---|---|
| "A22" | 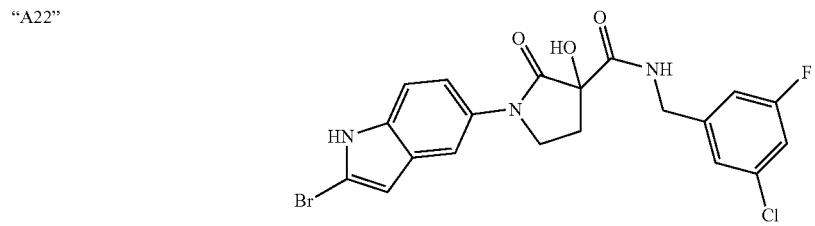

1-(2-Bromo-1H-indol-5-yl)-3-hydroxy-2-oxo-pyrrolidine-3-carboxylic acid 3-chloro-5-fluoro-benzylamide |
| "A23" | 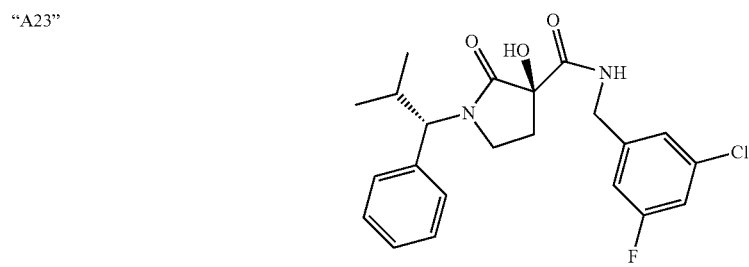

(R)-3-Hydroxy-1-((S)-2-methyl-1-phenyl-propyl)-2-oxo-pyrrolidine-3-carboxylic acid 3-chloro-5-fluoro-benzylamide |
| "A24" | 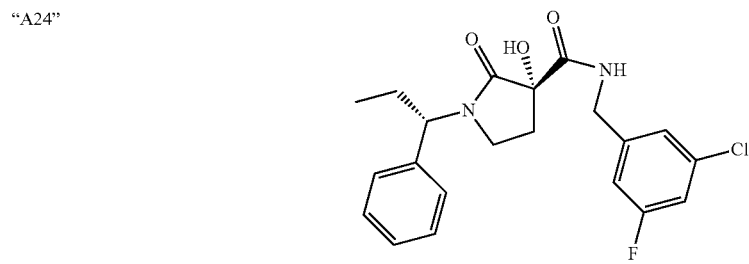

(S)-3-Hydroxy-2-oxo-1-((S)-1-phenyl-propyl)-pyrrolidine-3-carboxylic acid 3-chloro-5-fluoro-benzylamide |
| "A25" | 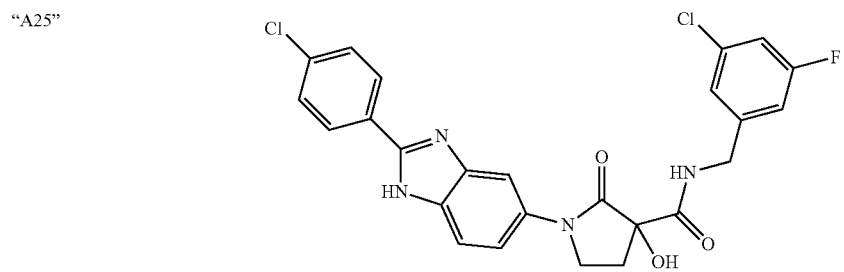

1-[2-(4-Chloro-phenyl)-1H-benzoimidazol-5-yl]-3-hydroxy-2-oxo-pyrrolidine-3-carboxylic acid 3-chloro-5-fluoro-benzylamide |

| Compound No. | Structure/name |
|---|---|
| "A26" | 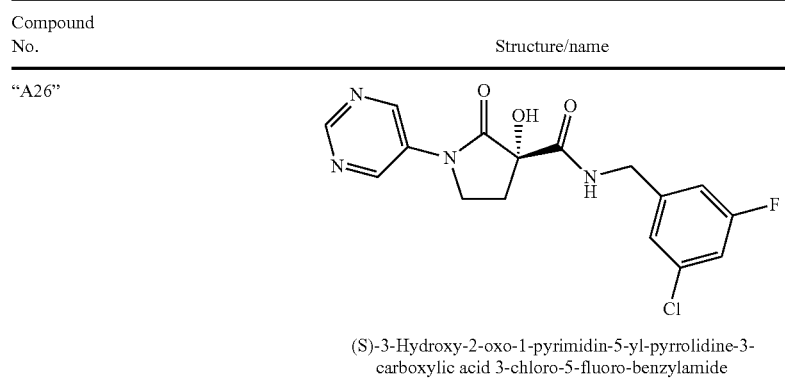
(S)-3-Hydroxy-2-oxo-1-pyrimidin-5-yl-pyrrolidine-3-carboxylic acid 3-chloro-5-fluoro-benzylamide |
| "A27" | 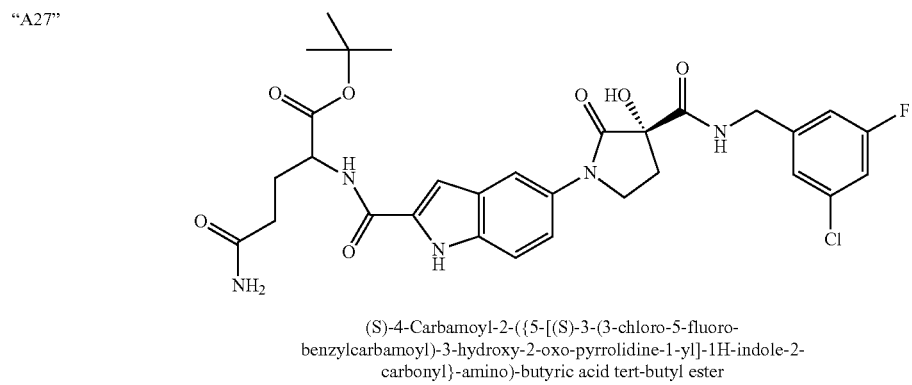
(S)-4-Carbamoyl-2-({5-[(S)-3-(3-chloro-5-fluoro-benzylcarbamoyl)-3-hydroxy-2-oxo-pyrrolidine-1-yl]-1H-indole-2-carbonyl}-amino)-butyric acid tert-butyl ester |
| "A28" | 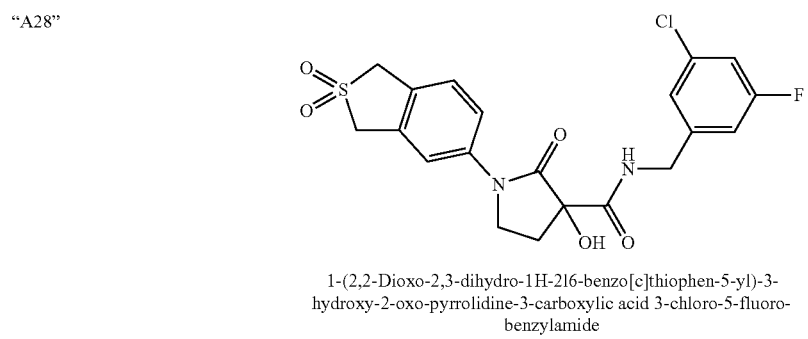
1-(2,2-Dioxo-2,3-dihydro-1H-2l6-benzo[c]thiophen-5-yl)-3-hydroxy-2-oxo-pyrrolidine-3-carboxylic acid 3-chloro-5-fluoro-benzylamide |
| "A29" | 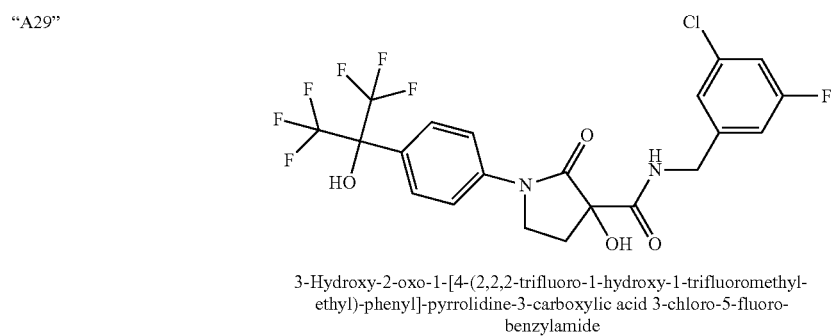
3-Hydroxy-2-oxo-1-[4-(2,2,2-trifluoro-1-hydroxy-1-trifluoromethyl-ethyl)-phenyl]-pyrrolidine-3-carboxylic acid 3-chloro-5-fluoro-benzylamide |

| Compound No. | Structure/name |
|---|---|
| "A30" | 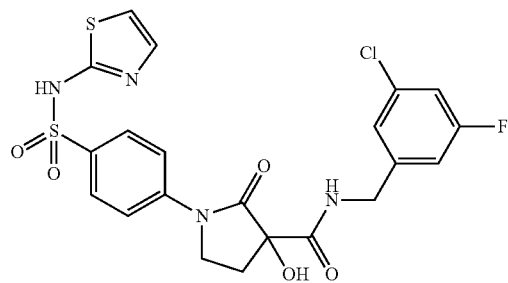<br>3-Hydroxy-2-oxo-1-[4-(thiazol-2-ylsulfamoyl)-phenyl]-pyrrolidine-3-carboxylic acid 3-chloro-5-fluoro-benzylamide |
| "A31" | 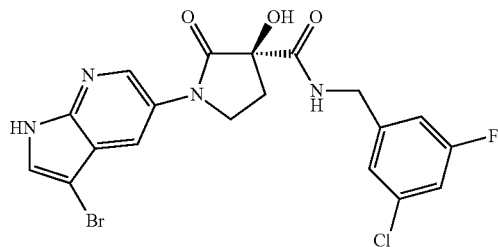<br>(R)-1-(3-Bromo-1H-pyrrolo[2,3-b]pyridin-5-yl)-3-hydroxy-2-oxo-pyrrolidine-3-carboxylic acid 3-chloro-5-fluoro-benzylamide |
| "A32" | 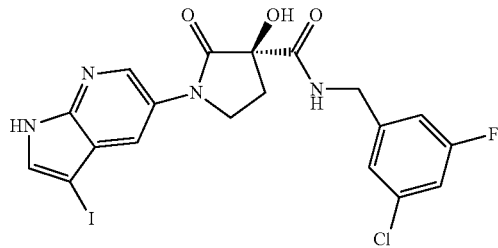<br>(R)-3-Hydroxy-1-(3-iodo-1H-pyrrolo[2,3-b]pyridin-5-yl)-2-oxo-pyrrolidine-3-carboxylic acid 3-chloro-5-fluoro-benzylamide |
| "A33" | 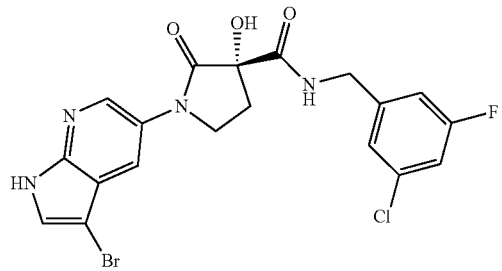<br>(S)-1-(3-Bromo-1H-pyrrolo[2,3-b]pyridin-5-yl)-3-hydroxy-2-oxo-pyrrolidine-3-carboxylic acid 3-chloro-5-fluoro-benzylamide |

| Compound No. | Structure/name |
|---|---|
| "A34" | 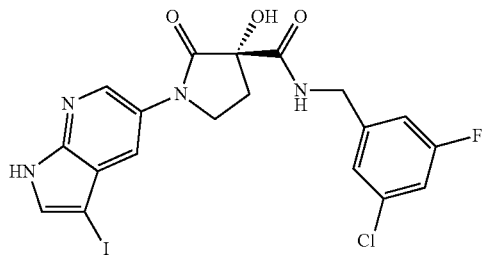<br>(S)-3-Hydroxy-1-(3-iodo-1H-pyrrolo[2,3-b]pyridin-5-yl)-2-oxo-pyrrolidine-3-carboxylic acid 3-chloro-5-fluoro-benzylamide |
| "A35" | 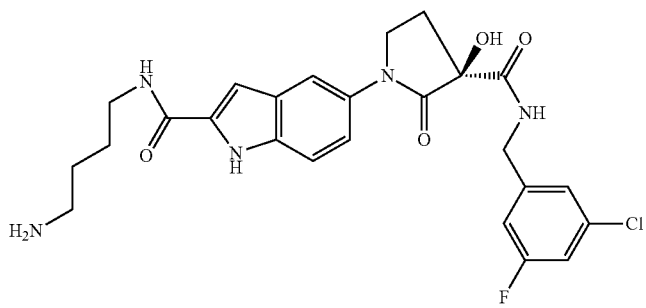<br>5-[(S)-3-(3-Chloro-5-fluoro-benzylcarbamoyl)-3-hydroxy-2-oxo-pyrrolidin-1-yl]-1H-indole-2-carboxylic acid (4-amino-butyl)-amide |
| "A36" | 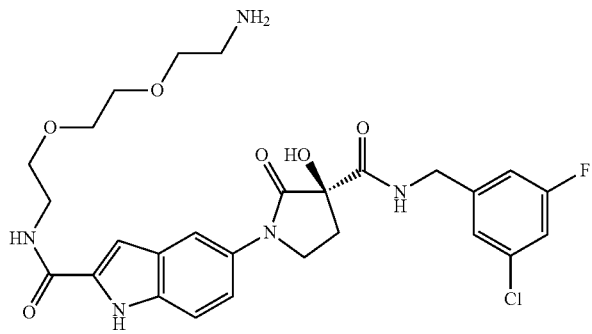<br>5-[(R)-3-(3-Chloro-5-fluoro-benzylcarbamoyl)-3-hydroxy-2-oxo-pyrrolidin-1-yl]-1H-indole-2-carboxylic acid {2-[2-(2-amino-ethoxy)-ethoxy]-ethyl}-amide |
| "A37" | 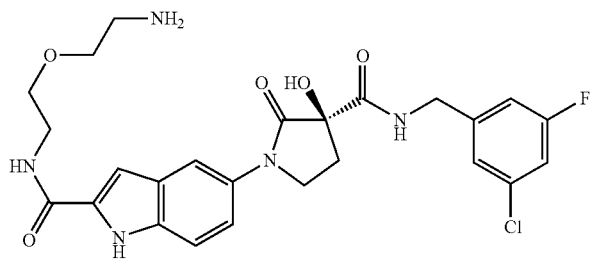<br>5-[(R)-3-(3-Chloro-5-fluoro-benzylcarbamoyl)-3-hydroxy-2-oxo-pyrrolidin-1-yl]-1H-indole-2-carboxylic acid [2-(2-amino-ethoxy)-ethyl]-amide |

| Compound No. | Structure/name |
|---|---|
| "A38" | 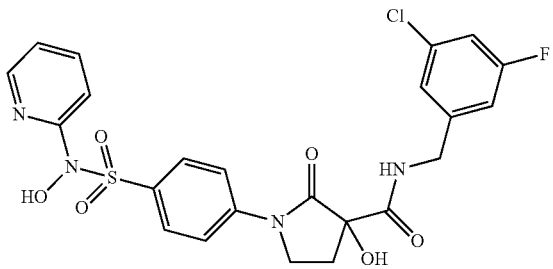<br>3-Hydroxy-1-[4-(hydroxy-pyridin-2-yl-sulfamoyl)-phenyl]-2-oxo-pyrrolidine-3-carboxylic acid 3-chloro-5-fluoro-benzylamide |
| "A39" | 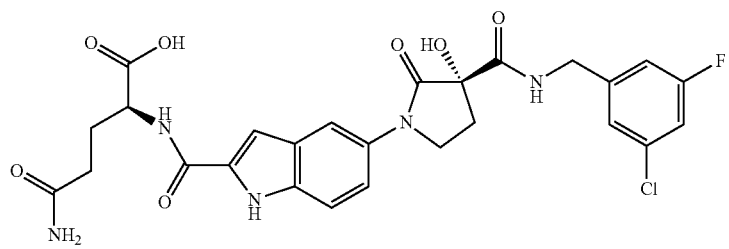<br>(S)-4-Carbamoyl-2-({5-[(S)-3-(3-chloro-5-fluoro-benzylcarbamoyl)-3-hydroxy-2-oxo-pyrrolidin-1-yl]-1H-indole-2-carbonyl}-amino)-butyric acid |
| "A40" | 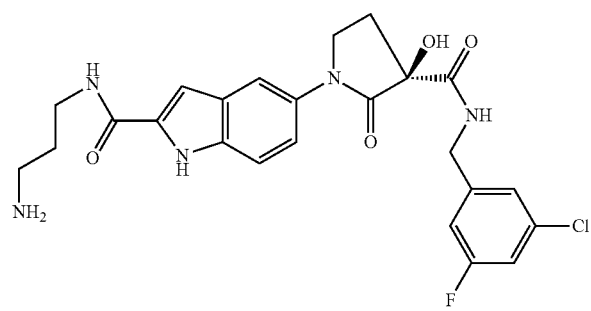<br>5-[(S)-3-(3-Chloro-5-fluoro-benzylcarbamoyl)-3-hydroxy-2-oxo-pyrrolidin-1-yl]-1H-indole-2-carboxylic acid (3-amino-butyl)-amide |
| "A41" | 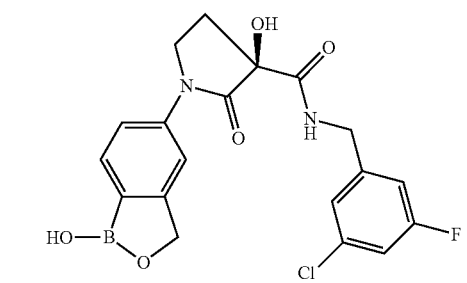<br>(S)-3-Hydroxy-1-(1-hydroxy-1,3-dihydro-benzo[c][1,2]oxaborol-5-yl)-2-oxo-pyrrolidine-3-carboxylic acid 3-chloro-5-fluoro-benzylamide |

-continued

| Compound No. | Structure/name |
|---|---|
| "A42" | 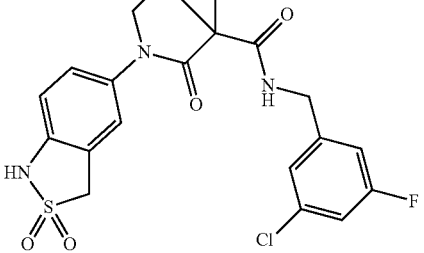
1-(2,2-Dioxo-2,3-dihydro-1H-2l6-benzo[c]isothiazol-5-yl)-3-hydroxy-2-oxo-pyrrolidine-3-carboxylic acid 3-chloro-5-fluoro-benzylamide |
| "A43" | 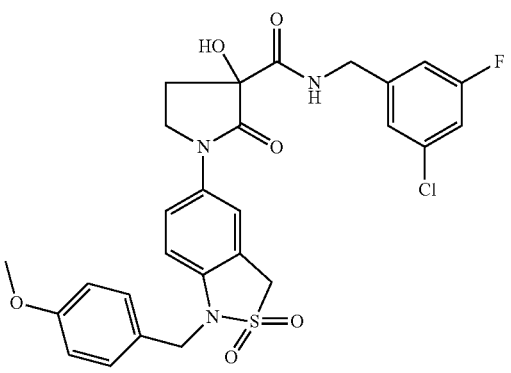
3-Hydroxy-1-[1-(4-methoxy-benzyl)-2,2-dioxo-2,3-dihydro-1H-2l6-benzo[c]isothiazol-5-yl]-2-oxo-pyrrolidine-3-carboxylic acid 3-chloro-5-fluoro-benzylamide |
| "A44" | 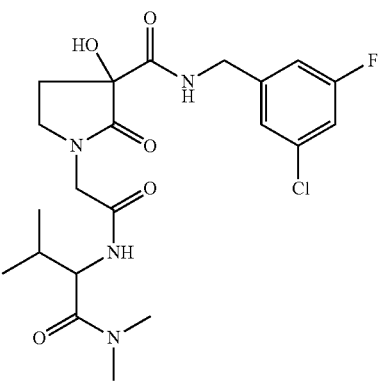
1-[(1-Dimethylcarbamoyl-2-methyl-propylcarbamoyl)-methyl]-3-hydroxy-2-oxo-pyrrolidine-3-carboxylic acid 3-chloro-5-fluoro-benzylamide |

| Compound No. | Structure/name |
|---|---|
| "A46" | 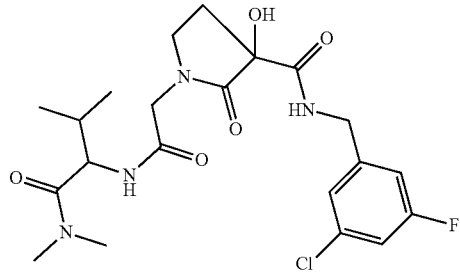<br>1-[(1-Dimethylcarbamoyl-2-methyl-propylcarbamoyl)-methyl]-3-hydroxy-2-oxo-pyrrolidine-3-carboxylic acid 3-chloro-5-fluoro-benzylamide |
| "A47" | 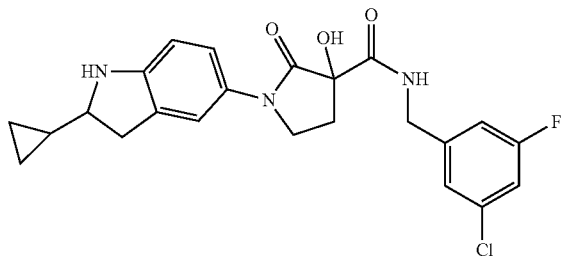<br>1-(2-Cyclopropyl-2,3-dihydro-1H-indol-5-yl)-3-hydroxy-2-oxo-pyrrolidine-3-carboxylic acid 3-chloro-5-fluoro-benzylamide |
| "A48" | 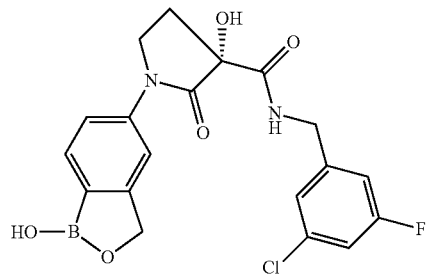<br>(R)-3-Hydroxy-1-(1-hydroxy-1,3-dihydro-benzo[c][1,2]oxaborol-5-yl)-2-oxo-pyrrolidine-3-carboxylic acid 3-chloro-5-fluoro-benzylamide |
| "A49" | 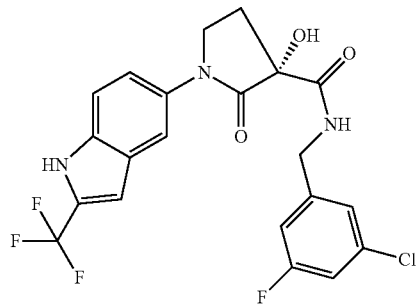<br>(R)-3-Hydroxy-2-oxo-1-(2-trifluoromethyl-1H-indol-5-yl)-pyrrolidine-3-carboxylic acid 3-chloro-5-fluoro-benzylamide |

| Compound No. | Structure/name |
|---|---|
| "A50" | 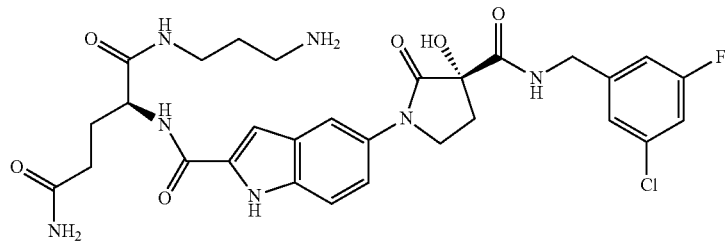<br>(S)-2-({5-[(S)-3-(3-Chloro-5-fluoro-benzylcarbamoyl)-3-hydroxy-2-oxo-pyrrolidin-1-yl]-1H-indole-2-carbonyl}-amino)-pentanedioic acid 5-amide 1-[(3-amino-propyl)-amide] |
| "A51" | 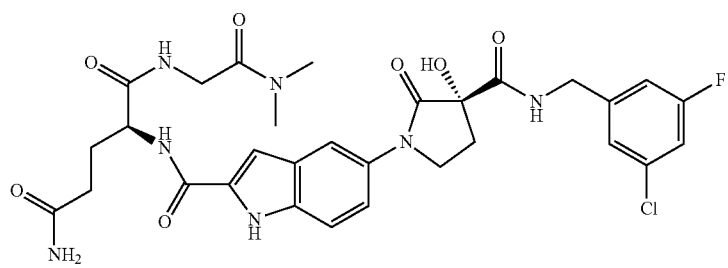<br>(S)-2-({5-[(S)-3-(3-Chloro-5-fluoro-benzylcarbamoyl)-3-hydroxy-2-oxo-pyrrolidin-1-yl]-1H-indole-2-carbonyl}-amino)-pentanedioic acid 5-amide 1-dimethylcarbamoylmethyl-amide |
| "A52" | 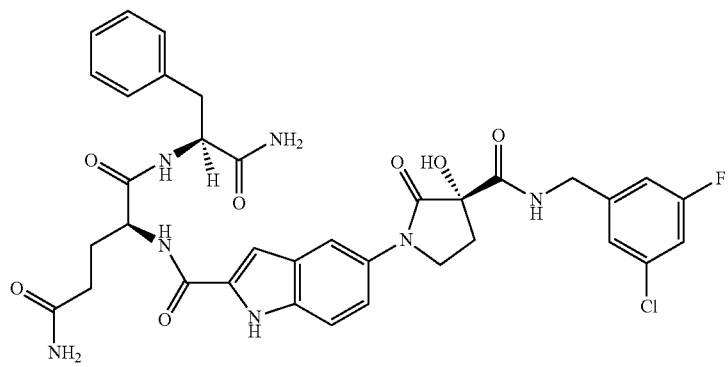<br>(S)-2-({5-[(S)-3-(3-Chloro-5-fluoro-benzylcarbamoyl)-3-hydroxy-2-oxo-pyrrolidin-1-yl]-1H-indole-2-carbonyl}-amino)-pentanedioic acid 5-amide 1-[((S)-1-carbamoyl-2-phenyl-ethyl)-amide] |
| "A53" | 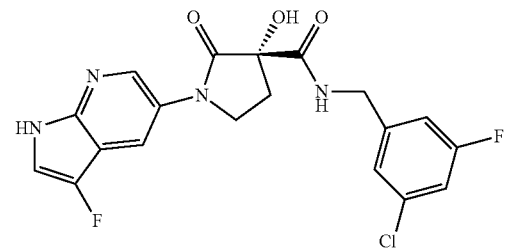<br>(S)-1-(3-Fluoro-1H-pyrrolo[2,3-b]pyridin-5-yl)-3-hydroxy-2-oxo-pyrrolidine-3-carboxylic acid 3-chloro-5-fluoro-benzylamide |

| Compound No. | Structure/name |
|---|---|
| "A54" | 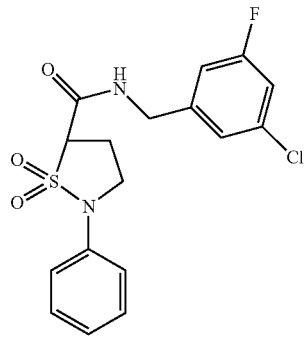
1,1-Dioxo-2-phenyl-1l6-isothiazolidine-5-carboxylic acid 3-chloro-5-fluoro-benzylamide |
| "A55" | 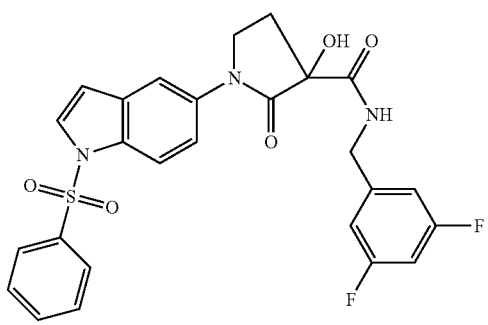
1-(1-Benzenesulfonyl-1H-indol-5-yl)-3-hydroxy-2-oxo-pyrrolidine-3-carboxylic acid 3,5-difluoro-benzylamide |
| "A56" | 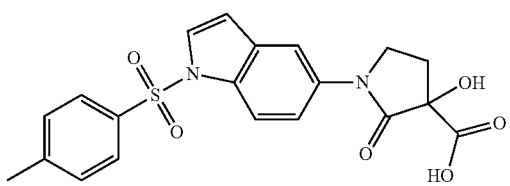
3-Hydroxy-2-oxo-1-[1-(toluene-4-sulfonyl)-1H-indol-5-yl]-pyrrolidine-3-carboxylic acid |
| "A57" | 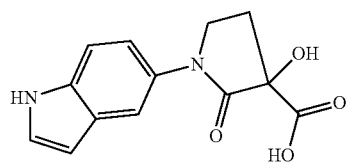
3-Hydroxy-1-(1H-indol-5-yl)-2-oxo-pyrrolidine-3-carboxylic acid |

| Compound No. | Structure/name |
|---|---|
| "A58" | 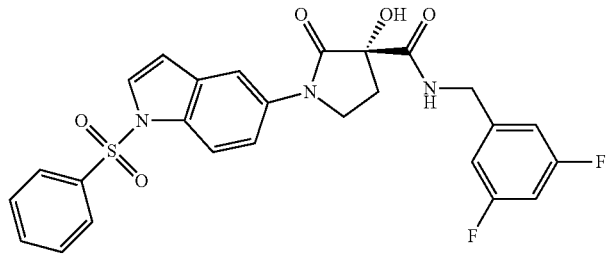<br>(S)-1-(1-Benzenesulfonyl-1H-indol-5-yl)-3-hydroxy-2-oxo-pyrrolidine-3-carboxylic acid 3,5-difluoro-benzylamide |
| "A59" | 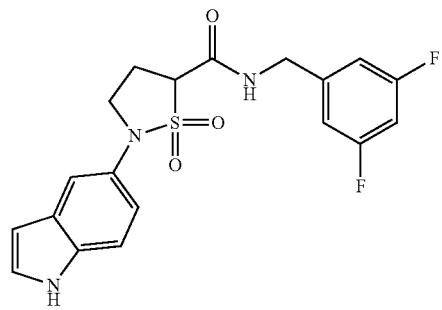<br>2-(1H-Indol-5-yl)-1,1-dioxo-1l6-isothiazolidine-5-carboxylic acid 3,5-difluoro-benzylamide |
| "A60" | 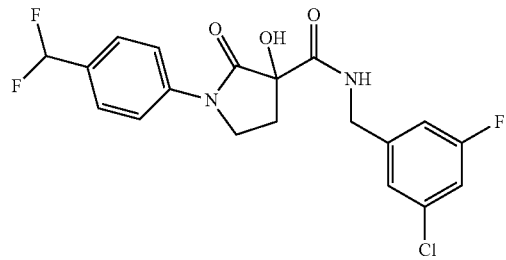<br>1-(4-Difluoromethyl-phenyl)-3-hydroxy-2-oxo-pyrrolidine-3-carboxylic acid 3-chloro-5-fluoro-benzylamide |
| "A61" | 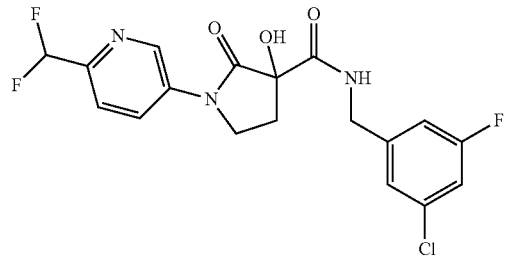<br>1-(6-Difluoromethyl-pyridin-3-yl)-3-hydroxy-2-oxo-pyrrolidine-3-carboxylic acid 3-chloro-5-fluoro-benzylamide |

| Compound No. | Structure/name |
|---|---|
| "A62" | 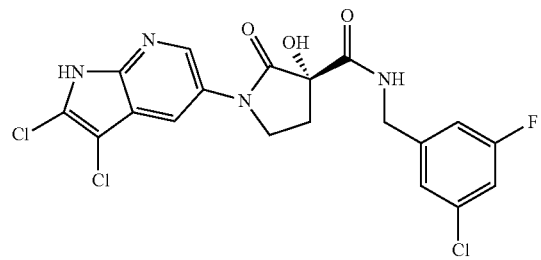<br>(S)-1-(2,3-Dichloro-1H-pyrrolo[2,3-b]pyridin-5-yl)-3-hydroxy-2-oxo-pyrrolidine-3-carboxylic acid 3-chloro-5-fluoro-benzylamide |
| "A63" | 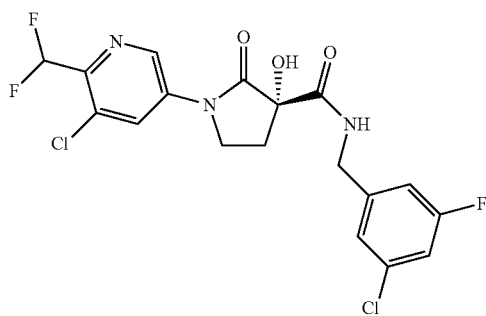<br>(S)-1-(5-Chloro-6-difluoromethyl-pyridin-3-yl)-3-hydroxy-2-oxo-pyrrolidine-3-carboxylic acid 3-chloro-5-fluoro-benzylamide |
| "A64" | 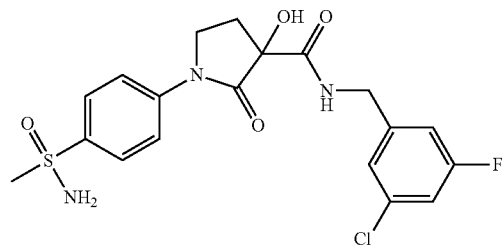<br>3-Hydroxy-1-(4-methanesulfoximinoyl-phenyl)-2-oxo-pyrrolidine-3-carboxylic acid 3-chloro-5-fluoro-benzylamide |
| "A65" | 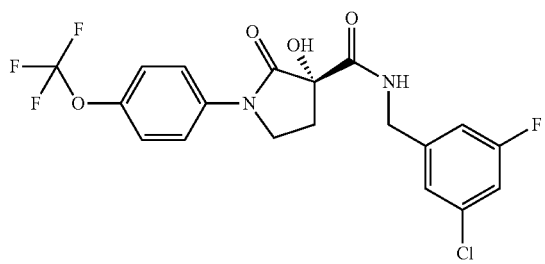<br>(S)-3-Hydroxy-2-oxo-1-(4-trifluoromethoxy-phenyl)-pyrrolidine-3-carboxylic acid 3-chloro-5-fluoro-benzylamide |

| Compound No. | Structure/name |
|---|---|
| "A66" | 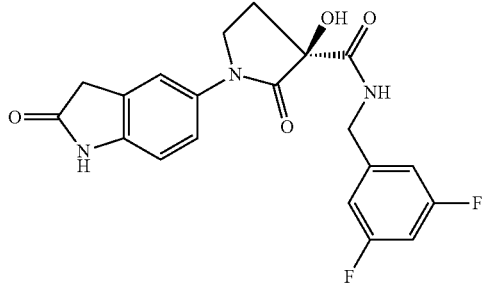<br>(S)-3-Hydroxy-2-oxo-1-(2-oxo-2,3-dihydro-1H-indol-5-yl)-pyrrolidine-3-carboxylic acid 3,5-difluoro-benzylamide |
| "A67" | 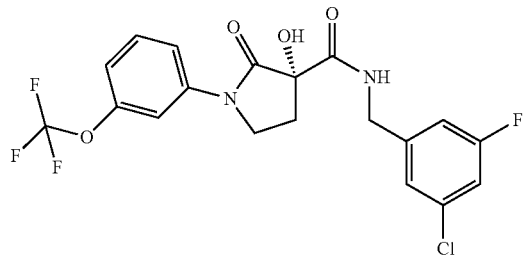<br>(S)-3-Hydroxy-2-oxo-1-(3-trifluoromethoxy-phenyl)-pyrrolidine-3-carboxylic acid 3-chloro-5-fluoro-benzylamide |
| "A68" | 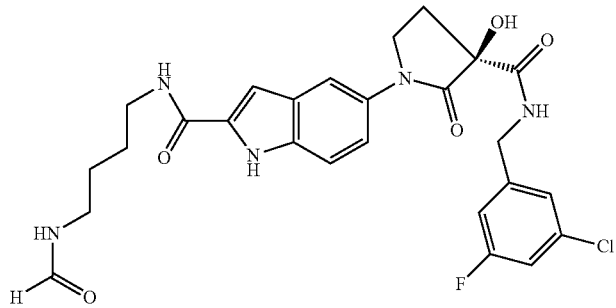<br>5-[(S)-3-(3-Chloro-5-fluoro-benzylcarbamoyl)-3-hydroxy-2-oxo-pyrrolidin-1-yl]-1H-indole-2-carboxylic acid (4-formylamino-butyl)-amide |
| "A69" | 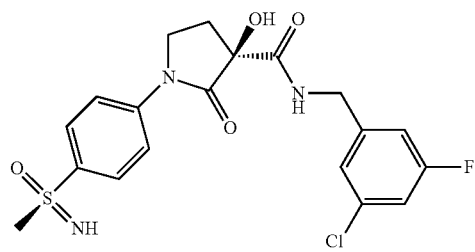<br>$(R)_S,(S)$-3-Hydroxy-1-(4-methanesulfoximinoyl-phenyl)-2-oxo-pyrrolidine-3-carboxylic acid 3-chloro-5-fluoro-benzylamide |

| Compound No. | Structure/name |
|---|---|
| "A70" | 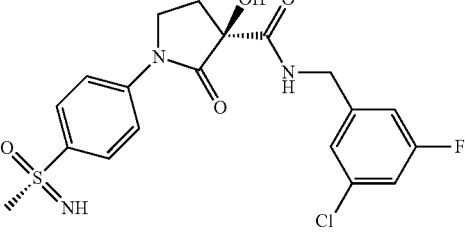<br>(S)$_S$,(S)-3-Hydroxy-1-(4-methanesulfoximinoyl-phenyl)-2-oxo-pyrrolidine-3-carboxylic acid 3-chloro-5-fluoro-benzylamide |
| "A71" | 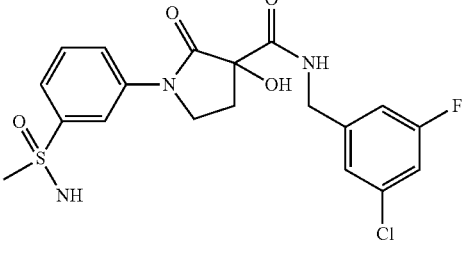<br>3-Hydroxy-1-(3-methanesulfoximinoyl-phenyl)-2-oxo-pyrrolidine-3-carboxylic acid 3-chloro-5-fluoro-benzylamide |
| "A72" | 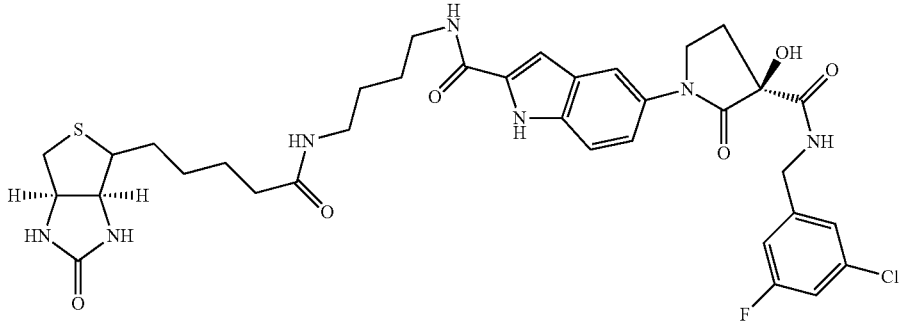<br>5-[(S)-3-(3-Chloro-5-fluoro-benzylcarbamoyl)-3-hydroxy-2-oxo-pyrrolidin-1-yl]-1H-indole-2-carboxylic acid {4-[5-((3aR,6aS)-2-oxo-hexahydro-thieno[3,4-d]imidazol-6-yl)-pentanoylamino]-butyl}-amide |
| "A73" | 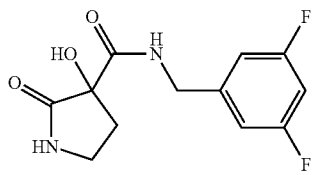<br>3-Hydroxy-2-oxo-pyrrolidine-3-carboxylic acid 3,5-difluoro-benzylamide |

| Compound No. | Structure/name |
|---|---|
| "A74" | 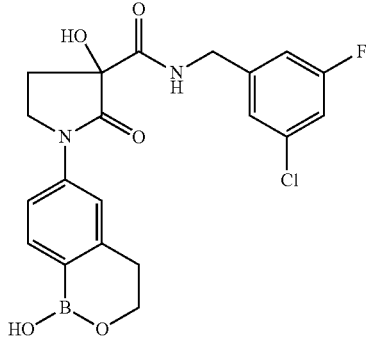<br>3-Hydroxy-1-(1-hydroxy-3,4-dihydro-1H-benzo[c][1,2]oxaborinin-6-yl)-2-oxo-pyrrolidine-3-carboxylic acid 3-chloro-5-fluoro-benzylamide |
| "A75" | 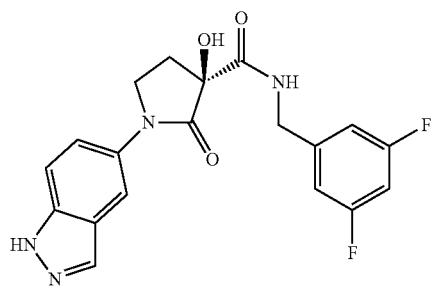<br>(S)-3-Hydroxy-1-(1H-indazol-5-yl)-2-oxo-pyrrolidine-3-carboxylic acid 3,5-difluoro-benzylamide |
| "A76" | 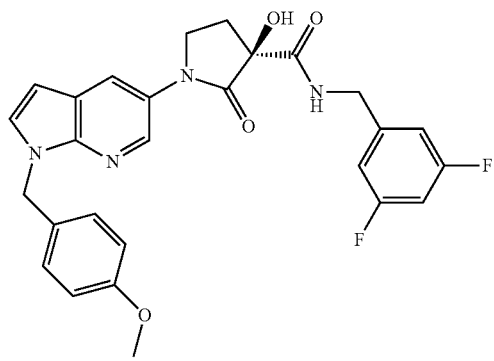<br>(S)-3-Hydroxy-1-[1-(4-methoxy-benzyl)-1H-pyrrolo[2,3-b]pyridin-5-yl]-2-oxo-pyrrolidine-3-carboxylic acid 3,5-difluoro-benzylamide |
| "A77" | 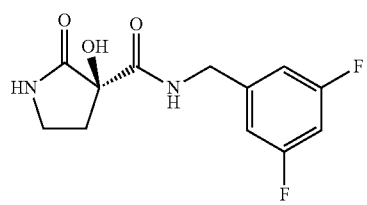<br>(S)-3-Hydroxy-2-oxo-pyrrolidine-3-carboxylic acid 3,5-difluoro-benzylamide |

| Compound No. | Structure/name |
|---|---|
| "A78" | 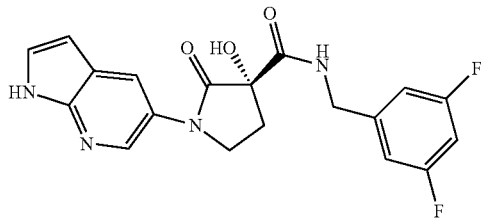<br>(S)-3-Hydroxy-2-oxo-1-(1H-pyrrolo[2,3-b]pyridin-5-yl)-pyrrolidine-3-carboxylic acid 3,5-difluoro-benzylamide |
| "A79" | 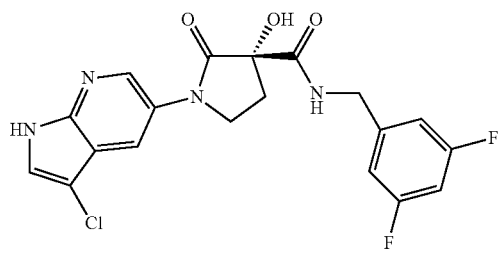<br>(S)-1-(3-Chloro-1H-pyrrolo[2,3-b]pyridin-5-yl)-3-hydroxy-2-oxo-pyrrolidine-3-carboxylic acid 3,5-difluoro-benzylamide |
| "A80" | 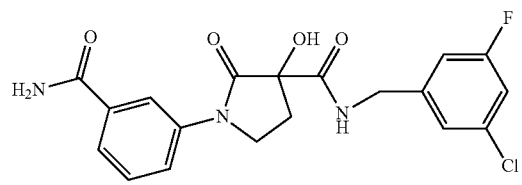<br>1-(3-Carbamoyl-phenyl)-3-hydroxy-2-oxo-pyrrolidine-3-carboxylic acid 3-chloro-5-fluoro-benzylamide |
| "A81" | 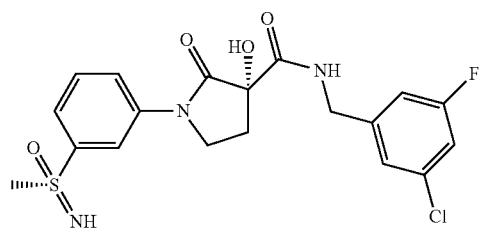<br>(S)$_S$,(S)-3-Hydroxy-1-(3-methanesulfoximinoyl-phenyl)-2-oxo-pyrrolidine-3-carboxylic acid 3-chloro-5-fluoro-benzylamide |
| "A82" | 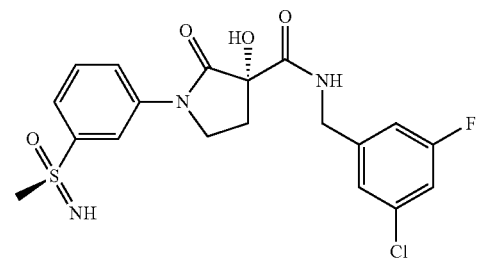<br>(R)$_S$,(S)-3-Hydroxy-1-(3-methanesulfoximinoyl-phenyl)-2-oxo-pyrrolidine-3-carboxylic acid 3-chloro-5-fluoro-benzylamide |

| Compound No. | Structure/name |
|---|---|
| "A83" | 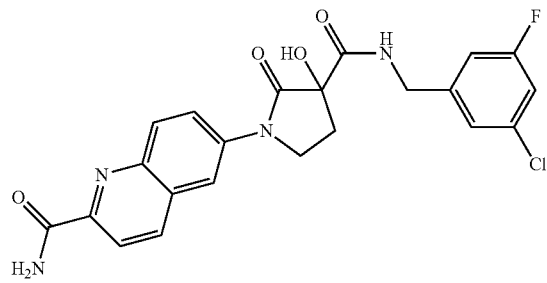<br>6-[3-(3-Chloro-5-fluoro-benzylcarbamoyl)-3-hydroxy-2-oxo-pyrrolidin-1-yl]-quinoline-2-carboxylic acid amide |
| "A85" | 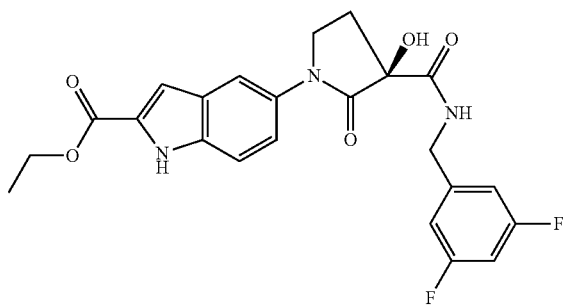<br>5-[(R)-3-(3,5-Difluoro-benzylcarbamoyl)-3-hydroxy-2-oxo-pyrrolidin-1-yl]-1H-indole-2-carboxylic acid ethyl ester |
| "A86" | 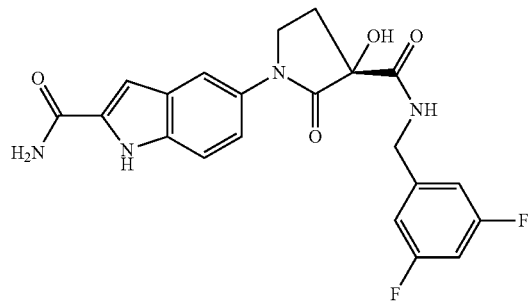<br>5-[(S)-3-(3,5-Difluoro-benzylcarbamoyl)-3-hydroxy-2-oxo-pyrrolidin-1-yl]-1H-indole-2-carboxylic acid amide |
| "A87" | 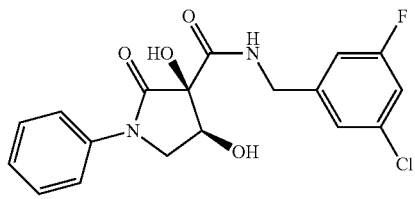<br>(3S,4R)-N-[(3-chloro-5-fluoro-phenyl)methyl]-3,4-dihydroxy-2-oxo-1-phenyl-pyrrolidine-3-carboxamide |

| Compound No. | Structure/name |
|---|---|
| "A88" | 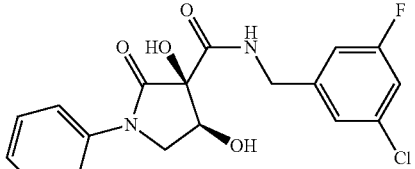<br>(3R,4S)-N-[(3-chloro-5-fluoro-phenyl)methyl]-3,4-dihydroxy-2-oxo-1-phenyl-pyrrolidine-3-carboxamide |
| "A89" | 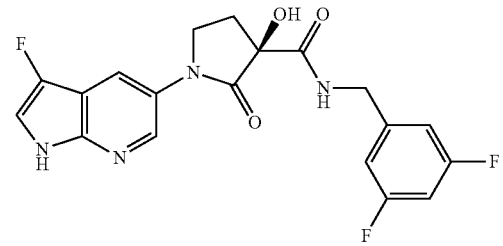<br>(S)-1-(3-Fluoro-1H-pyrrolo[2,3-b]pyridin-5-yl)-3-hydroxy-2-oxo-pyrrolidine-3-carboxylic acid 3,5-difluoro-benzylamide |
| "A90" | (S)-1-(2-Bromo-1H-indol-5-yl)-3-hydroxy-2-oxo-pyrrolidine-3-carboxylic acid 3-chloro-5-fluoro-benzylamide |
| "A91" | (R)-1-(2-Bromo-1H-indol-5-yl)-3-hydroxy-2-oxo-pyrrolidine-3-carboxylic acid 3-chloro-5-fluoro-benzylamide |
| "A92" | 5-[(R)-3-(3-Chloro-5-fluoro-benzylcarbamoyl)-3-hydroxy-2-oxo-pyrrolidin-1-yl]-1H-indole-2-carboxylic acid (4-amino-butyl)-amide | and pharmaceutically usable salts, tautomers and stereoisomers thereof, including mixtures thereof in all ratios.

The invention was based on the object of finding novel compounds having valuable properties, in particular those which can be used for the preparation of medicaments.

It has been found that the compounds according to the invention and salts thereof have very valuable pharmacological properties while being well tolerated.

In particular, they exhibit a regulatory, modulatory and/or inhibiting action on metal proteases, preferably on methionine aminopeptidase (MetAP), particularly on the sub-type MetAP-2.

They can be used as medicaments against cancer, but also as medicaments which positively influence fat metabolism, but also as medicaments against inflammation.

Other hydroxyl-substituted pyrrolidinones are known from:
WO 2011/004608 (MetAP2-inhibitors) and WO 2013/149704 (MetAP2-inhibitors);
Zeitschrift für Naturforschung, B: Chemical Sciences (1994), 49(11), 1586-95; Analytica Chimica Acta (1987), 202, 167-74;
Journal of Electroanalytical Chemistry and Interfacial Electrochemistry (1988), 239(1-2), 161-73;
Zeitschrift fuer Naturfor. Part B: Anorg. Chem. Org. Chem (1978), 336(12), 1540-6;
J. Chem. Soc. (1965), (October), 5556-62;
J. Chem. Soc. (1965), (October), 5551-6.
WO 01/79157 describes substituted hydrazides and N-alkoxyamides which have MetAP-2 inhibitory activity and can be used for the inhibition of angiogenesis, in particular for the treatment of diseases, such as, for example, cancer, whose development is dependent on angiogenesis.

WO 02/081415 describes MetAP-2 inhibitors which can be used for the treatment of cancer, haemangioma, proliferative retinopathy, rheumatoid arthritis, atherosclerotic neovascularisation, psoriasis, ocular neovascularisation and obesity.

WO 2008/011114 describes compounds as angiogenesis inhibitors and MetAP-2 inhibitors which can be used for the treatment of lymphoid leukaemia and lymphoma.

The action of the compounds according to the invention against cancer lies in particular in their action against angiogenesis. Angiogenesis inhibition has proven helpful in more than 70 diseases, such as, for example, ovarian cancer (F. Spinella et al. J. Cardiovasc. Pharmacol. 2004, 44, S140), breast cancer (A. Morabito et al. Crit. Rev. Oncol./Hematol. 2004, 49, 91), prostate cancer (B. Nicholson et al. Cancer Metastas. Rev. 2001, 20, 297), diabetic blindness, psoriasis and macular degeneration (E. Ng et al. Can. J. Ophthalmol. 2005, 23, 3706).

Proteases regulate many different cell processes, particularly the modulation of peptides and proteins, particularly protein conversion, protein ripening and signal peptide processing, the breakdown of abnormal proteins and the deactivation/activation of regulatory proteins. In particular, the amino-terminal modification of nascent polypeptides represents the most frequent modulation. Aminoproteases are metalloproteases which cleave off amino acids from the unprotected N terminus of peptides or proteins, which can be carried out in either a co- or post-translatory manner.

Methionine aminopeptidase (MetAP) cleaves terminal methionine of nascent peptides in particular if the penultimate amino acid is small and uncharged (for example Gly, Ala, Ser, Thr, Val, Pro or Cys).

In many disease processes, angiogenesis is either causally at the centre of the disease or has a worsening effect on the progression of the disease. In cancer events, for example, angiogenesis results in the tumour increasing in size and being able to enter other organs. Other diseases in which angiogenesis plays an importantrole are psoriasis, arthrosis, arteriosclerosis and eye diseases, such as diabetic retinopathy, age-induced macular degeneration, rubeosis iridis or neovascular glaucoma, furthermore in inflammations. The compounds on which this invention is based, compositions which comprise these compounds, and the processes described can thus be employed for the treatment of these diseases.

Accordingly, the compounds according to the invention or a pharmaceutically acceptable salt thereof are administered for the treatment of cancer, including solid carcinomas, such as, for example, carcinomas (of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The present invention therefore relates to compounds according to the invention as medicaments and/or medicament active compounds in the treatment and/or prophylaxis of the said diseases and to the use of compounds according to the invention for the preparation of a pharmaceutical for the treatment and/or prophylaxis of the said diseases and to a process for the treatment of the said diseases comprising the administration of one or more compounds according to the invention to a patient in need of such an administration.

It can be shown that the compounds according to the invention have an anti-carcinogenic action. The compounds according to the invention are administered to a patient having a disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both the prevention of diseases and the treatment of pre-existing conditions. The prevention of proliferation/vitality is achieved by administration of the compounds according to the invention prior to the development of overt disease, for example for preventing tumour growth. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compounds according to the invention can be determined by in vitro testing. Typically, a culture of the cell is incubated with a compound according to the invention at various concentrations for a period of time which is sufficient to allow the active agents to induce cell death or to inhibit cell proliferation, cell vitality or migration, usually between about one hour and one week. In vitro testing can be carried out using cultivated cells from a biopsy sample. The amount of cells remaining after the treatment are then determined.

The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

It has been found that the compounds according to the invention cause specific inhibition of MetAP-2. The compounds according to the invention preferably exhibit an advantageous biological activity which can be detected in the tests described, for example, herein. In such tests, the compounds according to the invention exhibit and cause an inhibiting effect, which is usually documented by $IC_{50}$ values in a suitable range, preferably in the micromolar range and more preferably in the nanomolar range.

In addition, the compounds according to the invention can be used to achieve additive or synergistic effects in certain existing cancer chemotherapies and radiotherapies and/or to restore the efficacy of certain existing cancer chemotherapies and radiotherapies.

The compounds according to the invention can also be used for the treatment of obesity. Henri R. Lijnen et al. in Obesity, Vol. 18 no. 12, 2241-2246 (2010) describes the use of fumagillin, an Met-AP2 inhibitor, in the reduction of adipose tissue.

The use of Met-AP2 inhibitors (compounds of the fumagillin type) for the treatment of obesity is also described in WO 2011/085201 A1.

The compounds according to the invention can also be used for the treatment of malaria. X. Chem et al. in Chemistry & Biology, Vol. 16, 193-202 (2009) describes the use of fumagillin, an Met-AP2 inhibitor, for the treatment of malaria.

The compounds according to the invention can also be used for the treatment of benign prostate hypertrophy.

The use of Met-AP2 inhibitors (compounds of the fumagillin type) for the treatment of benign prostate hypertrophy is described in WO 2011/085198 A1.

Compounds according to the invention are also taken to mean the hydrates and solvates of these compounds, furthermore pharmaceutically usable derivatives. The invention also relates to the optically active forms (stereoisomers), salts, the enantiomers, the racemates, the diastereomers and the hydrates and solvates of these compounds. The term solvates of the compounds is taken to mean adductions of inert solvent molecules onto the compounds which form owing to their mutual attractive force. solvates are, for example, mono- or dihydrates or alkoxides.

The term pharmaceutically usable derivatives is taken to mean, for example, the salts of the compounds according to the invention and also so-called prodrug compounds.

The term prodrug derivatives is taken to mean compounds according to the invention which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active compound which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side effects or also the reduction in the advance of a disease, condition or disorder.

The expression "therapeutically effective amount" also encompasses the amounts which are effective for increasing normal physiological function.

The invention also relates to the use of mixtures of the compounds according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Preferred compounds according to the invention are selected from the group

| Compound No. | Structure/name |
| --- | --- |
| "A55" | 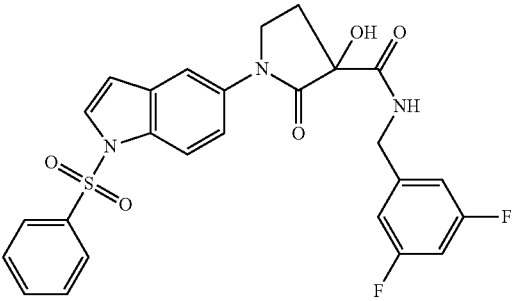<br>1-(1-Benzenesulfonyl-1H-indol-5-yl)-3-hydroxy-2-oxo-pyrrolidine-3-carboxylic acid 3,5-difluoro-benzylamide |
| "A58" | 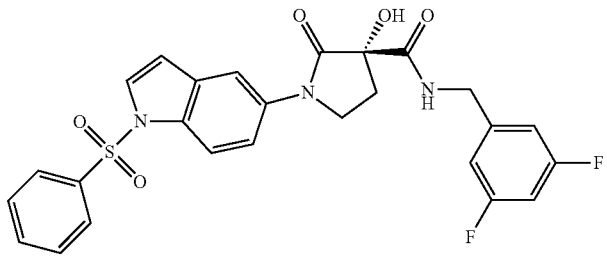<br>(S)-1-(1-Benzenesulfonyl-1H-indol-5-yl)-3-hydroxy-2-oxo-pyrrolidine-3-carboxylic acid 3,5-difluoro-benzylamide |
| "A59" | 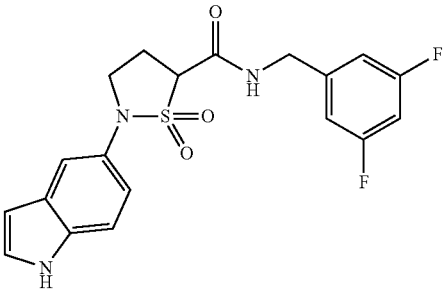<br>2-(1H-Indol-5-yl)-1,1-dioxo-1l6-isothiazolidine-5-carboxylic acid 3,5-difluoro-benzylamide |

| Compound No. | Structure/name |
|---|---|
| "A66" | 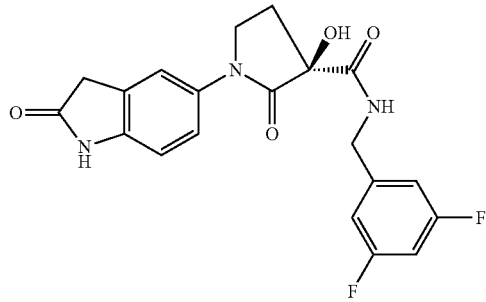<br>(S)-3-Hydroxy-2-oxo-1-(2-oxo-2,3-dihydro-1H-indol-5-yl)-pyrrolidine-3-carboxylic acid 3,5-difluoro-benzylamide |
| "A73" | 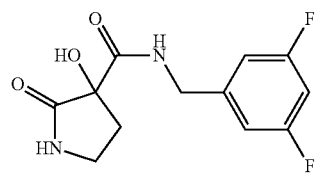<br>3-Hydroxy-2-oxo-pyrrolidine-3-carboxylic acid 3,5-difluoro-benzylamide |
| "A75" | 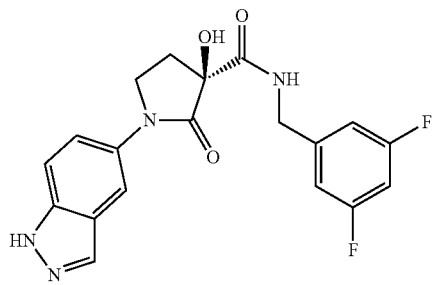<br>(S)-3-Hydroxy-1-(1H-indazol-5-yl)-2-oxo-pyrrolidine-3-carboxylic acid 3,5-difluoro-benzylamide |
| "A76" | 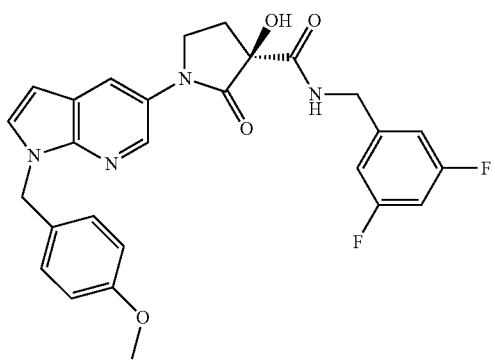<br>(S)-3-Hydroxy-1-[1-(4-methoxy-benzyl)-1H-pyrrolo[2,3-b]pyridin-5-yl]-2-oxo-pyrrolidine-3-carboxylic acid 3,5-difluoro-benzylamide |

-continued

| Compound No. | Structure/name |
|---|---|
| "A77" | 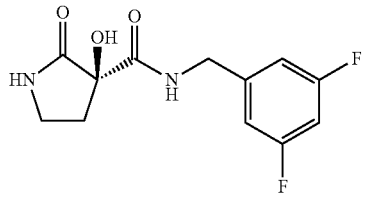<br>(S)-3-Hydroxy-2-oxo-pyrrolidine-3-carboxylic acid 3,5-difluoro-benzylamide |
| "A78" | 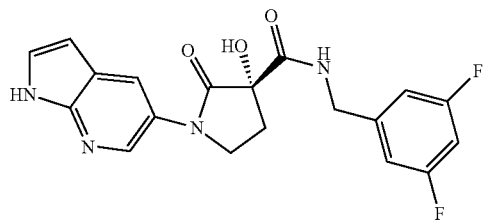<br>(S)-3-Hydroxy-2-oxo-1-(1H-pyrrolo[2,3-b]pyridin-5-yl)-pyrrolidine-3-carboxylic acid 3,5-difluoro-benzylamide |
| "A79" | 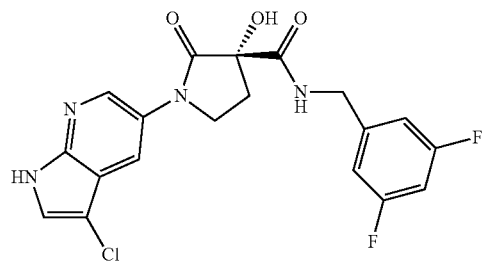<br>(S)-1-(3-Chloro-1H-pyrrolo[2,3-b]pyridin-5-yl)-3-hydroxy-2-oxo-pyrrolidine-3-carboxylic acid 3,5-difluoro-benzylamide |
| "A85" | 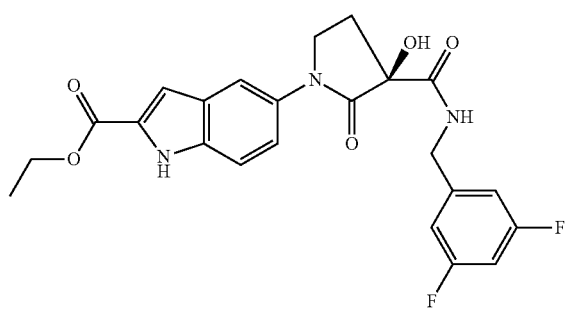<br>5-[(R)-3-(3,5-Difluoro-benzylcarbamoyl)-3-hydroxy-2-oxo-pyrrolidin-1-yl]-1H-indole-2-carboxylic acid ethyl ester |

| Compound No. | Structure/name |
|---|---|
| "A86" | 5-[(S)-3-(3,5-Difluoro-benzylcarbamoyl)-3-hydroxy-2-oxo-pyrrolidin-1-yl]-1H-indole-2-carboxylic acid amide | and pharmaceutically usable salts, tautomers and stereoisomers thereof, including mixtures thereof in all ratios.

Moreover, preferred compounds according to the invention are selected from the group

| Compound No. | Structure/name |
|---|---|
| "A64" | 3-Hydroxy-1-(4-methanesulfoximinoyl-phenyl)-2-oxo-pyrrolidine-3-carboxylic acid 3-chloro-5-fluoro-benzylamide |
| "A69" | (R)$_S$,(S)-3-Hydroxy-1-(4-methanesulfoximinoyl-phenyl)-2-oxo-pyrrolidine-3-carboxylic acid 3-chloro-5-fluoro-benzylamide |
| "A70" | (S)$_S$,(S)-3-Hydroxy-1-(4-methanesulfoximinoyl-phenyl)-2-oxo-pyrrolidine-3-carboxylic acid 3-chloro-5-fluoro-benzylamide |
| "A71" | 3-Hydroxy-1-(3-methanesulfoximinoyl-phenyl)-2-oxo-pyrrolidine-3-carboxylic acid 3-chloro-5-fluoro-benzylamide |
| "A81" | (S)$_S$,(S)-3-Hydroxy-1-(3-methanesulfoximinoyl-phenyl)-2-oxo-pyrrolidine-3-carboxylic acid 3-chloro-5-fluoro-benzylamide |

| Compound No. | Structure/name |
|---|---|
| "A82" | 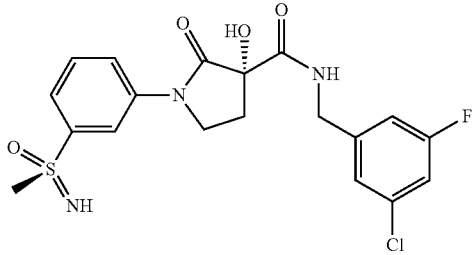<br>(R)$_S$,(S)-3-Hydroxy-1-(3-methanesulfoximinoyl)-phenyl)-2-oxo-pyrrolidine-3-carboxylic acid 3-chloro-5-fluoro-benzylamide | and pharmaceutically usable salts, tautomers and stereoisomers thereof, including mixtures thereof in all ratios.

Preferably preferred are "A75", "A78" and "A79" and pharmaceutically usable salts, tautomers and stereoisomers thereof, including mixtures thereof in all ratios.

Compounds according to the invention and salts thereof are prepared as described for compounds of formula I in WO 2011/004608 and WO 2013/149704.

Preparation of compounds according to the invention is performed analogously to compounds of the formula I as described in WO 2011/004608 and pharmaceutically usable salts, tautomers and stereoisomers thereof, characterised in that a) a compound of the formula II

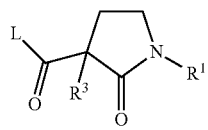

in which $R^1$ and $R^3$ have the meanings indicated in Claim 1 of WO 2011/004608,
and L denotes Cl, Br, I or a free or reactively functionally modified OH group,
is reacted with a compound of the formula III $R^2$—NHR$^4$     III 

in which $R^2$ and $R^4$ have the meanings indicated in Claim 1 of WO 2011/004608,
or b) for the preparation of compounds of the formula I of WO 2011/004608, in which $R^3$ denotes OH,
a compound of the formula IV

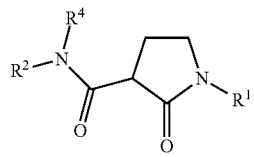

in which $R^1$, $R^2$ and $R^4$ have the meanings indicated in Claim 1 of WO 2011/004608,
is oxidised,
or c) a radical $R^3$ is converted into another radical $R^3$ by replacing an OH group with a halogen atom,
or replacing a halogen atom with $N_3$,
and/or a base or acid of the formula I is converted into one of its salts.

The compounds according to the invention and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Compounds according to the invention and compounds of the formula I as described in WO 2011/004608 or in WO 2013/149704 can preferably be obtained by reacting compounds of the formula II with a compound of the formula III.

The compounds of the formula II and of the formula III are generally known. If they are novel, however, they can be prepared by methods known per se.

In the compounds of the formula II, L preferably denotes Cl, Br, I or a free or a reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

The reaction preferably succeeds in the presence of a dehydrating agent, such as, for example, a carbodiimide, such as N,N'-dicyclohexylcarbodiimide ("DCCI"), 1,1'-carbonyldiimidazole or N-3-dimethylaminopropyl-N'-ethylcarbodiimide ("DAPECI"), furthermore propanephosphonic anhydride T3P (cf. Angew. Chem. 92, 129 (1980)), diphenylphosphoryl azide or 2-ethoxy-N-ethoxycarbonyl-1,2-dihydroquinoline, optionally in the presence of N-hydroxybenzotriaole;

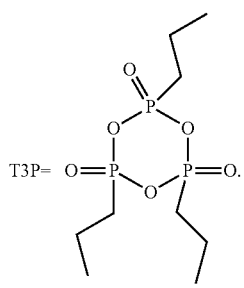 [SMILES: CCCP1(=O)OP(=O)(CCC)OP(=O)(CCC)O1]

The reaction is carried out in an inert solvent and is generally carried out in the presence of an acid-binding agent, preferably an organic base, such as DIPEA, triethylamine, dimethylaniline, pyridine or quinoline.

The addition of an alkali or alkaline-earth metal hydroxide, carbonate or bicarbonate or another salt of a weak acid of the alkali or alkaline-earth metals, preferably of potassium, sodium, calcium or caesium, may also be favourable.

Depending on the conditions used, the reaction time is between a few minutes and 14 days, the reaction temperature is between about −15° and 150°, normally between 40° and 130°, particularly preferably between 60° and 110° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to glycol ethers, such as ethylene glycol monomethyl ether, THF, dichloromethane and/or DMF.

Compounds of the formula I can furthermore preferably be obtained by oxidising compounds of the formula IV.

The oxidation is preferably carried out using tert-butyl hydroperoxide.

Depending on the conditions used, the reaction time is between a few minutes and 14 days, the reaction temperature is between about −15° and 150°, normally between 40° and 130°, particularly preferably between 60° and 110° C.

The solvent is preferably water, where the addition of an alkali or alkaline-earth metal hydroxide, carbonate or bicarbonate or another salt of a weak acid of the alkali or alkaline-earth metals, preferably of potassium, sodium, calcium or caesium, is also favourable.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds according to the invention are likewise included. In the case of certain compounds according to the invention, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoaryl-sulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds according to the invention which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds according to the invention are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds according to the invention are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active compound which comprises a compound according to the invention in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

The invention furthermore relates to medicaments comprising at least one compound according to the invention and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active compound per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethyl-aspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound according to the invention depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable salts and stereoisomers thereof, including mixtures thereof in all ratios, and at least one further medicament active compound.

The invention also relates to a set (kit) consisting of separate packs of
(a) an effective amount of a compound according to the invention and/or pharmaceutically usable salts and stereoisomers thereof, including mixtures thereof in all ratios,
and
(b) an effective amount of a further medicament active compound.

The set comprises suitable containers, such as boxes, individual bottles, bags or ampoules. The set may, for example, comprise separate ampoules, each containing an effective amount of a compound according to the invention and/or pharmaceutically usable salts and stereoisomers thereof, including mixtures thereof in all ratios,
and an effective amount of a further medicament active compound in dissolved or lyophilised form.

The invention relates to the compounds according to the invention, and pharmaceutically usable salts, tautomers and stereoisomers thereof, including mixtures thereof in all ratios, for use for the treatment of tumours, tumour metastases, proliferative diseases of the mesangial cells, haemangioma, proliferative retinopathy, rheumatoid arthritis, atherosclerotic neovascularisation, psoriasis, ocular neovascularisation, osteoporosis, diabetes and obesity, lymphoid leukaemia, lymphoma, malaria and prostate hypertrophy
Use The present compounds are suitable as pharmaceutical active compounds for mammals, especially for humans, in the treatment and control of diseases. These diseases include the proliferation of tumour cells, pathological neovascularisation (or angiogenesis), which promotes the growth of solid tumours, neovascularisation in the eye (diabetic retinopathy, age-induced macular degeneration and the like) and inflammation (psoriasis, rheumatoid arthritis and the like), and proliferative diseases of the mesangial cells.

The present invention encompasses the use of the compounds according to the invention and/or physiologically acceptable salts and solvates thereof for the preparation of a medicament for the treatment or prevention of tumours, tumour diseases and/or tumour metastases.

The tumour disease is preferably selected from the group tumour of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx, the lung, the skin, monocytic leukaemia, lung adenocarcinoma, small-cell lung carcinoma, pancreatic cancer, glioblastoma, breast carcinoma, acute myeloid leukaemia, chronic myeloid leukaemia, acute lymphatic leukaemia, chronic lymphatic leukaemia, Hodgkin's lymphoma, non-Hodgkin's lymphoma.

Likewise encompassed is the use of the compounds according to the invention and/or physiologically acceptable salts and solvates thereof for the preparation of a medicament for the treatment of osteoporosis, diabetes and obesity.

Likewise encompassed is the use of the compounds according to the invention and/or physiologically acceptable salts and solvates thereof for the preparation of a medicament for the treatment or prevention of a disease in which angiogenesis is involved.

A disease of this type in which angiogenesis is involved is an eye disease, such as retina vascularisation, diabetic retinopathy, age-induced macular degeneration and the like.

The angiogenic disease is preferably selected from the group diabetic retinopathy, arthritis, cancer, psoriasis, Kaposi's sarcoma, haemangioma, myocardial angiogenesis, atherosclerotic plaque neovascularisation, angiogenic eye diseases, choroidal neovascularisation, retrolental fibroplasia, macular degeneration, corneal transplant rejection, rubeosis iridis, neuroscular glaucoma, Oster Webber syndrome.

The proliferative disease of the mesangial cells is preferably selected from the group
glomerulonephritis, diabetic nephropathy, malignant nephrosclerosis, thrombotic microangiopathy syndrome, transplant rejection, glomerulopathy.

The use of compounds according to the invention and/or physiologically acceptable salts and solvates thereof for the preparation of a medicament for the treatment or prevention of inflammatory diseases likewise falls within the scope of the present invention. Examples of such inflammatory diseases include rheumatoid arthritis, psoriasis, contact dermatitis, delayed hypersensitivity reaction and the like.

The inflammatory disease is preferably selected from the group inflammatory bowel disease, arthritis, atheroscleros
is, asthma, allergies, inflammatory kidney diseases, multiple sclerosis, chronic obstructive pulmonary disease, inflammatory skin diseases, pardontal diseases, psoriasis, T-cell-promoted immune disease.

The inflammatory bowel disease is preferably selected from the group ulcerative colitis, Crohn's disease, non-specific colitis.

The T-cell-promoted immune disease is preferably selected from the group allergic encephalomyelitis, allergic neuritis, transplant rejection, graft-versus-host reaction, myocarditis, thyroiditis, nephritis, systemic lupus erythematosus, insulin-dependent diabetes mellitus.

The arthritis disease is preferably selected from the group rheumatoid arthritis, osteoarthritis, Caplan's syndrome, Felty's syndrome, Sjogren's syndrome, spondylitis ankylosans, Still's disease, chondrocalcinosis, metabolic arthritis, rheumatic fever, Reiter's disease, Wissler's syndrome.

The inflammatory kidney disease is preferably selected from the group glomerulonephritis, glomerular injury, nephrotic syndrome, interstitial nephritis, lupus nephritis, Goodpasture's syndrome, Wegener's granulomatosis, renal vasculitis, IgA nephropathy, idiopatic glomerular disease.

The inflammatory skin disease is preferably selected from the group psoriasis, atopic dermatitis, contact sensitivity, acne.

Likewise encompassed is the use of the compounds according to the invention and/or pharmaceutically acceptable salts and solvates thereof for the preparation of a medicament for the treatment or prevention of a disease or condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds according to the invention and/or physiologically acceptable salts and solvates thereof for the preparation of a medicament for the treatment or prevention of retinal vascularisation.

Likewise encompassed is the use of the compounds according to the invention and/or pharmaceutically acceptable salts thereof for the preparation of a medicament for the treatment and/or combating of a tumour-induced disease in a mammal, in which to this method a therapeutically effective amount of a compound according to the invention is administered to a sick mammal in need of such treatment. The therapeutic amount varies according to the specific disease and can be determined by the person skilled in the art without undue effort.

The disclosed compounds according to the invention can be administered in combination with other therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds, conventional surgery or radiotherapy or medicinal therapy. Such medicinal therapy, e.g. a chemotherapy or a targeted therapy, may include one or more, but preferably one, of the following anti-tumor agents:

Alkylating Agents
such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone;
apaziquone, fotemustine, glufosfamide, palifosfamide, pipobroman, trofosfamide, uramustine, TH-302[4], VAL-083[4];
Platinum Compounds
such as carboplatin, cisplatin, eptaplatin, miriplatine hydrate, oxaliplatin, lobaplatin, nedaplatin, picoplatin, satraplatin;
lobaplatin, nedaplatin, picoplatin, satraplatin;
DNA Altering Agents
such as amrubicin, bisantrene, decitabine, mitoxantrone, procarbazine, trabectedin, clofarabine;
amsacrine, brostallicin, pixantrone, laromustine[1,3];
Topoisomerase Inhibitors
such as etoposide, irinotecan, razoxane, sobuzoxane, teniposide, topotecan; amonafide, belotecan, elliptinium acetate, voreloxin;
Microtubule Modifiers
such as cabazitaxel, docetaxel, eribulin, ixabepilone, paclitaxel, vinblastine, vincristine, vinorelbine, vindesine, vinflunine;
fosbretabulin, tesetaxel;
Antimetabolites
such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur;
doxifluridine, elacytarabine, raltitrexed, sapacitabine, tegafur[2,3], trimetrexate;
Anticancer Antibiotics
such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin;
aclarubicin, peplomycin, pirarubicin;
Hormones/Antagonists
such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];
Aromatase Inhibitors
such as aminoglutethimide, anastrozole, exemestane, fadrozole, letrozole, testolactone;
formestane;
Small Molecule Kinase Inhibitors
such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib;
afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];
Photosensitizers
such as methoxsalen[3];
porfimer sodium, talaporfin, temoporfin;
Antibodies
such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3];
catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];
Cytokines
such as aldesleukin, interferon alfa[2], interferon alfa2a[3], interferon alfa2b[2,3];
celmoleukin, tasonermin, teceleukin, oprelvekin[1,3], recombinant interferon beta-1a[4];
Drug Conjugates
such as denileukin diftitox, ibritumomab tiuxetan, iobenguane I123, prednimustine, trastuzumab emtansine, estramustine, gemtuzumab, ozogamicin, aflibercept;
cintredekin besudotox, edotreotide, inotuzumab ozogamicin, naptumomab estafenatox, oportuzumab monatox, technetium (99mTc) arcitumomab[1,3], vintafolide[1,3];
Vaccines
such as sipuleucel[3]; vitespen[3], emepepimut-S[3], oncoVAX[4], rindopepimut[3], troVax[4], MGN-1601[4], MGN-1703[4];
Miscellaneous
alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat;
celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4];
[1]Prop. INN (Proposed International Nonproprietary Name)
[2]Rec. INN (Recommended International Nonproprietary Names)
[3]USAN (United States Adopted Name)
[4]no INN.

Evidence of the Action of Pharmacological Inhibitors on the Proliferation/Vitality of Tumour Cells In Vitro 1.0 Background In the present experiment description, the inhibition of tumour cell proliferation/tumour cell vitality by active compounds is described.

The cells are sown in a suitable cell density in microtitre plates (96-well format) and the test substances are added in the form of a concentration series. After four further days of cultivation in serum-containing medium, the tumour cell proliferation/tumour cell vitality can be determined by means of an Alamar Blue test system.

2.0 Experimental Procedure 2.1 Cell Culture

For example commercially available colon carcinoma cell lines, ovary cell lines, prostate cell lines or breast cell lines, etc.

The cells are cultivated in medium. At intervals of several days, the cells are detached from the culture dishes with the aid of trypsin solution and sown in suitable dilution in fresh medium. The cells are cultivated at 37° Celsius and 10% $CO_2$.

2.2. Sowing of the Cells

A defined number of cells (for example 2000 cells) per culture/well in a volume of 180 µl of culture medium are sown in microtitre plates (96 well cell-culture plates) using a multichannel pipette. The cells are subsequently cultivated in a CO2 incubator (37° C. and 10% CO2).

2.3. Addition of the Test Substances

The test substances are dissolved, for example, in DMSO and subsequently employed in corresponding concentration (if desired in a dilution series) in the cell culture medium. The dilution steps can be adapted depending on the efficiency of the active compounds and the desired spread of the concentrations. Cell culture medium is added to the test substances in corresponding concentrations. The addition of the test substances to the cells can take place on the same day as the sowing of the cells. To this end, in each case 20 µl of substance solution from the predilution plate are added to the cultures/wells. The cells are cultivated for a further 4 days at 37° Celsius and 10% $CO_2$.

2.4. Measurement of the Colour Reaction

In each case, 20 µl of Alamar Blue reagent are added per well, and the microtitre plates are incubated, for example, for a further seven hours in a CO2 incubator (at 37° C. and 10% CO2). The plates are measured in a reader with a fluorescence filter at a wavelength of 540 nm. The plates can be shaken gently immediately before the measurement.

3. Evaluation

The absorbance value of the medium control (no cells and test substances used) is subtracted from all other absorbance values. The controls (cells without test substance) are set equal to 100 percent, and all other absorbance values are set in relation thereto (for example in % of control):

Calculation:

$$100 * \left( \frac{\text{value with cells and test substance} - \text{value of medium control}}{\text{value with cells} - \text{value of medium control}} \right)$$

$IC_{50}$ values (50% inhibition) are determined with the aid of statistics programs, such as, for example, RS1.

| Material | Order No. | Manufacturer |
|---|---|---|
| Microtitre plates for cell culture (Nunclon Surface 96-well plate) | 167008 | Nunc |
| DMEM | P04-03550 | Pan Biotech |
| PBS (10x) Dulbecco | 14200-067 | Gibco |
| 96-well plates (polypropylene) | 267334 | Nunc |
| AlamarBlue ™ | BUF012B | Serotec |
| FCS | 1302 | Pan Biotech GmbH |
| Trypsin/EDTA solution 10x | L 2153 | Biochrom AG |
| 75 cm² culture bottles | 353136 | BD Falcon |
| A2780 | 93112519 | ECACC |
| Colo205 | CCL222 | ATCC |
| MCF7 | HTB22 | ATCC |
| PC3 | CRL-1435 | ATCC |

Determination of the Proliferation Inhibition by Inhibitors of Methionine Aminopeptidase 2 in the BrdU Proliferation Test (Cellular Assay)

The inhibition of proliferation is determined by incorporation of bromodesoxyuridine (BrdU) into human umbilical vein endothelial cells (HUVECs, PromoCell, C-12200). The HUVECs are cultivated at 37° C. and 5% $CO_2$ in basal medium (PromoCell, C-22200) with supplement mix (PromoCell, C-39225). After detachment of the cells by means of trypsin/EDTA, the number of living cells is determined, and the cells are sown in a density of 1000 cells per cavity in a total volume of 175 µl (cavities are coated in advance either with supplemented culture medium for 1-2 hours at 37° C. or with 1.5% gelatine for 0.5-2 hours at 37° C.). After cultivation for 24 hours, the test substances are added in various concentrations (for example final concentrations 30 µM to 0.03 nM in 10-fold dilution steps) and a volume of 25 µl. The DMSO concentration is kept constant at 0.3%. After cultivation for a total of 48 or 72 hours, 20 µl of bromodesoxyuridine (Roche, #11647229001 diluted 1:1000 in culture medium, final concentration 10 µM) are added, and cultivation is continued for a further 20 to 24 hours. After incubation with test substances for a total of 72 or 96 hours, the culture medium is removed, and an immunohistochemical determination is carried out for detection of BrdU incorporation (BrdU ELISA, Roche, #11647229001). To this end, the cells are treated with a fixative for 30 min at room temperature and subsequently incubated with a peroxidase-labelled anti-BrdU antibody (diluted 1:100 in antibody dilution buffer) for 60 min at room temperature. After washing three times with 1-fold-concentrated DPBS buffer (Gibco, #14200), the enzymatic reaction is initiated in TMB substrate solution. The colour development is stopped after 15 min by addition of 25 µl of a 1M sulfuric acid solution. A determination of the optical density is carried out within 5 min by measurement at a wavelength of 450 nM. The controls used are cavities containing DMSO-treated cells (100% control) or empty cavities (blank value). The sensitivity of this test to inhibitors of methionine aminopeptidase is checked and confirmed using the inhibitor fumagillin.

MetAP-2 Activity Measurement

The MetAP-2 activity is determined by coupling enzymatic reactions. The $_{tripeptide}$ Met-Arg-Ser (MAS) is employed as substrate. The methionine liberated is firstly converted into $Met_{ox}$ and $H_2O_2$ by L-aminooxidase (AAO). In the second step, the peroxidase (POD) with the aid of the $H_2O_2$ catalyses the oxidation of the leukodye dianisidine to dianisidine$_{ox}$, the increase of which is detected photometrically at 450 nm.

MetAP-2 activity can be recorded continuously as kinetics. The reaction scheme illustrates that one mol of dianisidine$_{ox}$ is formed per mol of methionene. The MetAP-2 enzyme activity can therefore be calculated directly as Δ absorption per time unit. Qualification of the MetAP-2 activity (mol of Met/time unit) is possible with the aid of the dianisidine$_{ox}$ extinction coefficient. The change in extinction per time unit is depicted graphically and a slope calculation is carried out in the visually linear region of the reaction. The activities of the compounds are summarised in Table 1.

HUVEC Proliferation Quantified by BrdU Incorporation
HUVEC Means Human Umbilical Vein Endothelial Cells The activities of the compounds are summarised in Table 2.

Purpose/Definition of the Assay

HUVEC proliferation is measured after a 5 day incubation period using incorporation of BrdU as a measure of cell cycle activity. Cells are incubated in the presence or absence of test substances. During the last 18 to 24 hours of the incubation period BrdU is added to the medium. BrdU is incorporated into the DNA as the cells progress through S-phase (DNA synthesis) of the cell cycle. The cells are fixed and the amount of BrdU incorporated can be quantified using a commercial ELISA for detection of BrdU.

This assay was developed for screening test substances for the MetAP2 project but is applicable for assessing the effect of any substance that affects HUVEC proliferation.

Reagents
EGM MV—cell culture medium
Trypsin/EDTA (0.5%/0.53 mM solution)
Dulbeccos's PBS without Ca and Mg
Cell Proliferation ELISA BrdU colormetric
DMSO
Reference Compounds

| Abbott reference A-832234 | MSC2129790 |
| TNP-470 | MSC1902850 |

Procedure

HUVEC are routinely cultured in EGM MV medium and used between passages 3 and 8.

Day 1—Plate Cells

Pipet 75 µl/well growth medium EGM MV (Promocell) in a 96 well plate, Row H wells receive only medium, no cells for reagent blank.

Incubate plate at 37° C. while preparing the cells.
Harvest HUVEC with trypsin as usual:
Aspirate the culture medium, wash the cell monolayer once with 10 ml PBS, add 2 ml trypsin solution per T75 cm$^2$ flask and incubate at 37° C. for 2-5 min to detach cells.
Rinse the cells from the flask with 10 ml EGM MV and transfer to a centrifuge tube.
Centrifuge 5 min at 400×g, resuspend and count.
Adjust cell concentration to 1e4 cells/ml.
In the plate prepared with 75 ul/well, pipet 100 ul/well=1000 cells/well in 175 ul/well total volume.
Incubate plate at 37° C. overnight.

Day 2—Add Test Substances

In general, test substances are supplied by the dispensary at 10 mM in REMP tubes.

Test substances are pre-diluted in DMSO and then working dilutions in cell culture medium are prepared for addition to the cell plate.

Concentration range for test substances is 30 µM, serial 3-fold dilutions with a 6 point curve.

Reference Compounds—

| MSC 1902850 TNP-270 | start at 30 nM (1:1000 pre-dilution) |
| MSC 2129790 | start at 300 nM (1:100 pre-dilution) |

Reference compounds must be pre-diluted in DMSO to create a concentration curve in which the expected $EC_{50}$ falls in the middle of the 6-point curve. The 10 mM stock solution of the reference compounds is pre-diluted in DMSO, and then added to the plate as described below.

Pre-Dilution of Test Substances in DMSO:

In a 96 well polypropylene round bottom plate:
Row A—put 20 µl of the 10 mM test substance stock solution in DMSO (or reference compounds pre-diluted as noted above).
Row B-H put 20 ul DMSO
Serially dilute 3-fold by transferring 10 µl from Row A to Row B, mix and transfer 10 µl to Row C, etc to Row F.
Row G is for 100%=untreated, DMSO alone. This is the Neutral reference=value of 0% effect in Assay Explorer.
Row H is the reagent blank with no cells, just medium. This is the Scale Reference/Type Inhibition=value of −100% effect in Assay Explorer.

Working Dilutions in Culture Medium:

In a 96 well polypropylene round bottom plate:
Put 244 µl culture medium/well
Transfer 6 µl of the DMSO dilutions to the wells with cell culture medium=1:41,6 dilution=8-fold concentration.
Transfer 25 µl/well of the working dilution to the cell plates with 175 µl, =1:8 dilution.
From the 10 mM stock solution the final dilution is 1:333 (ie 41.6×8) for a final concentration of 30 µM in the test plate. All wells contain 0.3% DMSO.
Incubate the plate at 37° C. until Day 4.

Day 4—Add BrdU

BrdU stock solution is 10 mM in PBS (1000-fold stock).
Prepare a working dilution of 100 µM by diluting it 1:100 in culture medium.
Each plate requires 2.2 ml. Use 22 µl BrdU stock in 2.2 ml EGM MV medium.
Pipet 20 µl/well (1:10 dilution). Final concentration=10 µM BrdU.
Incubate the plate for 18-24 hr 37° C.

Day 5—Fix, Denature, ELISA—Follow Kit Instructions with the Following Changes in Volume:

Shake out the medium, lightly tap on paper towels to remove all medium.
Add 100 ul FixDenat solution from the kit and incubate at room temperature for 30 min.
Shake out the FixDenat and lightly tap on paper towels.
Briefly allow the plate to air-dry (1-2 min), allowing the alcohol in the fix to evaporate.
Prepare anti-BrdU peroxidase conjugate working solution fresh each time by diluting the stock 1:100 in the antibody dilution buffer supplied in the kit.
Each plate requires 5 ml, use 50 µl in 5 ml antibody dilution buffer.

Anti BrdU peroxidase conjugate stock solution is made by dissolving the lyophilized material in 1.1 ml MilliQ water. Stock is stored at 4° C. for several weeks, long term −20° C.

Add 50 ul/well anti-BrdU peroxidase conjugate and incubate 60-90 min at room temperature on the Eppendorf plate shaker 300 rpm.

Shake out the antibody solution and wash the plate 3× with 225 μl/well

Washing solution (supplied in the kit or PBS with Ca/Mg can also be used).

Add 100 μl/well substrate and incubate at room temperature for 5-10 min.

Add 25 μl/well 1 M $H_2SO_4$ stop solution and read the plate at 450 nm/reference 690 nm in the Tecan InfiniteM200.
Note:

Alternatively the following substrate mix can be used. Use 100 ml/well and 50 μl 1M $H_2SO_4$ stop solution. Wavelengths for measurement as stated above.
Substrate: Mix Fresh Each Time

| Citrate/Phosphate buffer pH 5 | 9 ml |
|---|---|
| 1 mg/ml tetramethyl benzidine in DMSO | 1 ml |

For each 10 ml substrate add 2 ul 30% $H_2O_2$ just before use 0.1M Citric acid
0.2M dibasic sodium phosphate
Mix 243 ml of citric acid+257 ml of Na Phosphate dibasic to get pH 5.0
Bring volume to 1000 ml with MilliQ water
3,3',5,5'Tetra methyl benzidine Merck VWR 1.08622
Plate Layout—End Concentrations

|   | 1 | 2 | 3 | 4 | 5 | 6 | 7 | 8 | 9 | 10 | 11 | 12 |
|---|---|---|---|---|---|---|---|---|---|---|---|---|
| A | 30 μM |   |   | 30 μM |   |   | 0.3 μM |   |   | 0.03 μM |   |   |
| B | 10 μM |   |   | 10 μM |   |   | 0.1 μM |   |   | 00.1 μM |   |   |
| C | 3.3 μM |   |   | 3.3 μM |   |   | 0.033 μM |   |   | 0.003 μM |   |   |
| D | 1.1 μM |   |   | 1.1 μM |   |   | 0.011 μM |   |   | 0.001 μM |   |   |
| E | 0.33 μM |   |   | 0.33 μM |   |   | 0.0037 μM |   |   | 3.7e−4 μM |   |   |
| F | 0.12 μM |   |   | 0.12 μM |   |   | 0.0012 μM |   |   | 1.2e−4 μM |   |   |
| G | 0 |   |   | 0 |   |   | 0 |   |   | 0 |   |   |
| H | No | Cells |   | No | Cells |   | No | Cells |   | No | Cells |   |
|   | Test 1 |   |   | Test 2 |   |   | 2129790 |   |   | 1902850 |   |   |

All substances are run in triplicate.
Statistical Methods/Data Analysis
Reference compounds are run in every assay. The expected values are:
8e-10M (range 2e-10M to 1e-9M) for MSC1902850A
2e-8M (range 8e-9M to 6e-8M) for MSC2129790A
Background Activity—the Blank Value or Scale Reference=Wells with No Cells, should be 10% or Less of the Neutral Reference (Untreated Cells) Value.

Data is analyzed using the Assay Explorer program. Briefly, the blank is subtracted from all values, the triplicates are averaged and normalized to the untreated. EC50 is determined from a 4-parameter general sigmoidal curve (Hill fit $y=(s0-slnf)/(1+(x/AC50)^{nHill})+slnf$) in Assay Explorer, Symyx). The processed data (EC50 or % Effect if no EC50 if reached, Efficacy) is uploaded directly from Assay Explorer to the MSRDB.
Safety Considerations The test substances are of unknown activity and should be handled with the usual safety precautions. Gloves and lab coat should be worn at all times.

When working with concentrated stock solutions in DMSO, nitrile rather than latex gloves are recommended.

All contaminated waste (tips, tubes, plates) are disposed of in the cytotoxic lab waste bins labeled with the appropriate sticker (2.29728.888).

List of Chemicals, Disposables and Equipment Required

| Product | Vendor | Order number |
|---|---|---|
| EGM MV | Promocell | C22020 |
| Endothelial Basal Medium containing: 0.4% |   |   |
| 5% FCS, |   |   |
| endothelial cell growth supplement (bovine hypothalamic extract), 10 ng/ml |   |   |
| EGF, 90 μg/ml |   |   |
| heparin, 1 μg/ml |   |   |
| hydrocortisone |   |   |
| Trypsin/EDTA | InVitrogen | 15400-054 |
| Final trypsin concentration = 0.05% |   |   |
| Final EDTA concnetration = 0.53 mM |   |   |
| Dulbecco's PBS, Ca, Mg - cation free | InVitrogen | 14190-094 |
| DMSO dimethylsulfoxide | VWR | 102931.0500 |
| Cell Proliferation ELISA, BrdU (colormetric) | Roche | 11 647229001 |
| 3,3',5,5'Tetra methyl benzidine | VWR | 1.08622 |
| NUNC 96-well (Nunclon) tissue culture plates | Nunc/VWR | 167008 (Nunc) |
| 96-well (0.5 ml/well) polypropylene round bottom plates | Nunc/VWR | 267334 (Nunc) |
| Tecan Infinitee M200 plate reader | Tecan |   |
| Multidrop combi Dispenser or other plate washer | Therno |   |

Solubility Measurement
Determination by shake flask solubility measurement
Eluent preparation:
Eluent A: 2 ml of diethylamine, for synthesis+1000 ml of methanol, LiChrosolv
Eluent B: 5 g of ammonium acetate, for analysis+5 ml of methanol, LiChrosolv+995 ml of ultrapure water
Sample Solvent:
Buffer: 3.954 g of sodium dihydrogenphosphate monohydrate+6.024 g of sodium chloride+950 ml of ultrapure water the pH is adjusted using 0.1 M NaOH or 0.1 M HCl.
Sample Preparation:
The samples are shaken at 37° C. and 450 rpm for 24 h.
After about 7 h, the pH of the samples is checked and adjusted if necessary.
It is also checked whether the sample is still present in excess.
Just before the end of the 24 h shaking time, the samples are again checked for pH and a precipitate.
Ultrapure water unit: MilliQ gradient, Millipore, instrument: F3PN37462D
Shaker: TiMix control, Bühler
Incubation hood: TH 15 Bühler pH meter: 766 Calimatic Knick instrument: pH 1
pH electrode: InLab 423 Mettler The racemic end products of the compounds according to the invention or the racemic intermediates can be separated simply and both on an analytical and also on a preparative scale via a chiral HPLC or SFC column.

LC-MS
column: Chromolith RP-18e 100-3
solvents:
A: water+0.05% formic acid
B: acetonitril+0.05% formic acid
flow: 2.4 ml/min
Gradient:
B: 0->2.8 min; 4%->100%
B: 2.8->3.3 min; 100%
time: 3.3 min

*LC-MS:
Column: XBridge C8, 3.5 μm, 4.6×50 mm; Solvent A: water+10 Mm NH$_4$HCO$_3$; Solvent B: ACN; Flow: 1 ml/min; Gradient: 0 min: 5% B, 8 min: 100% B, 8.1 min: 100% B, 8.5 min: 5% B, 10 min 5% B.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation.

Synthesis schemes for the preparation of compounds according to present invention:

a)

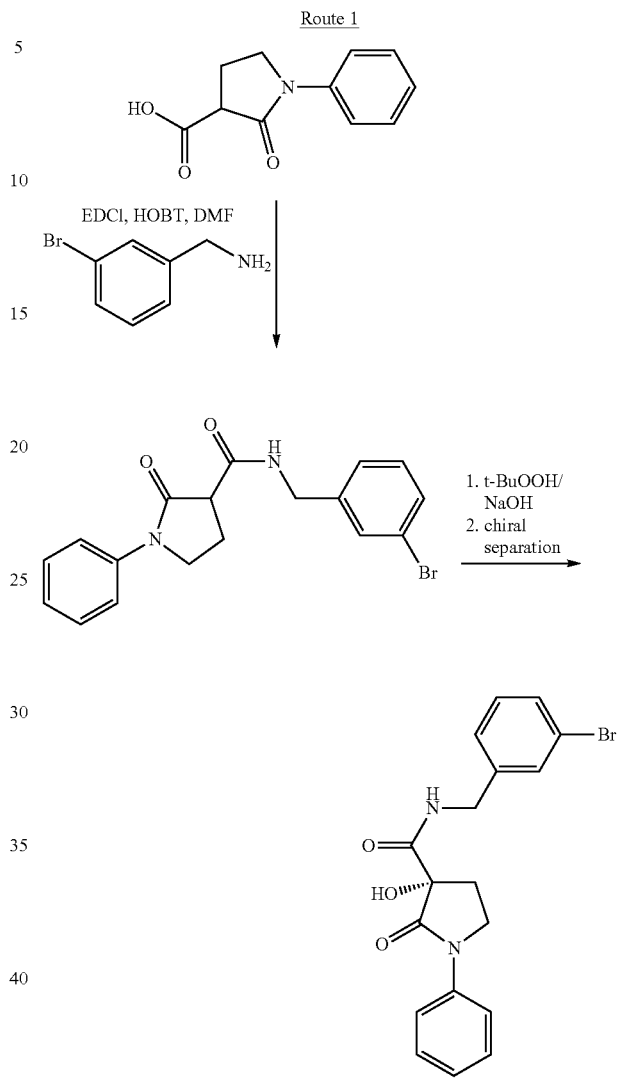

b)

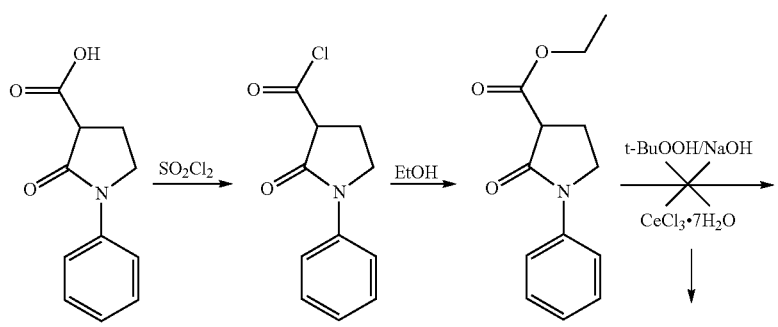

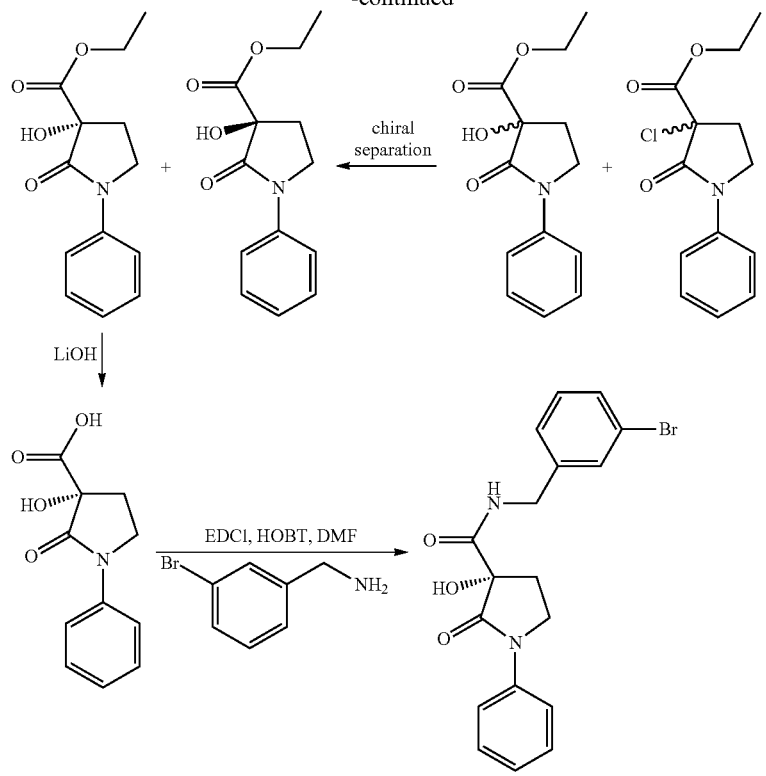

c)

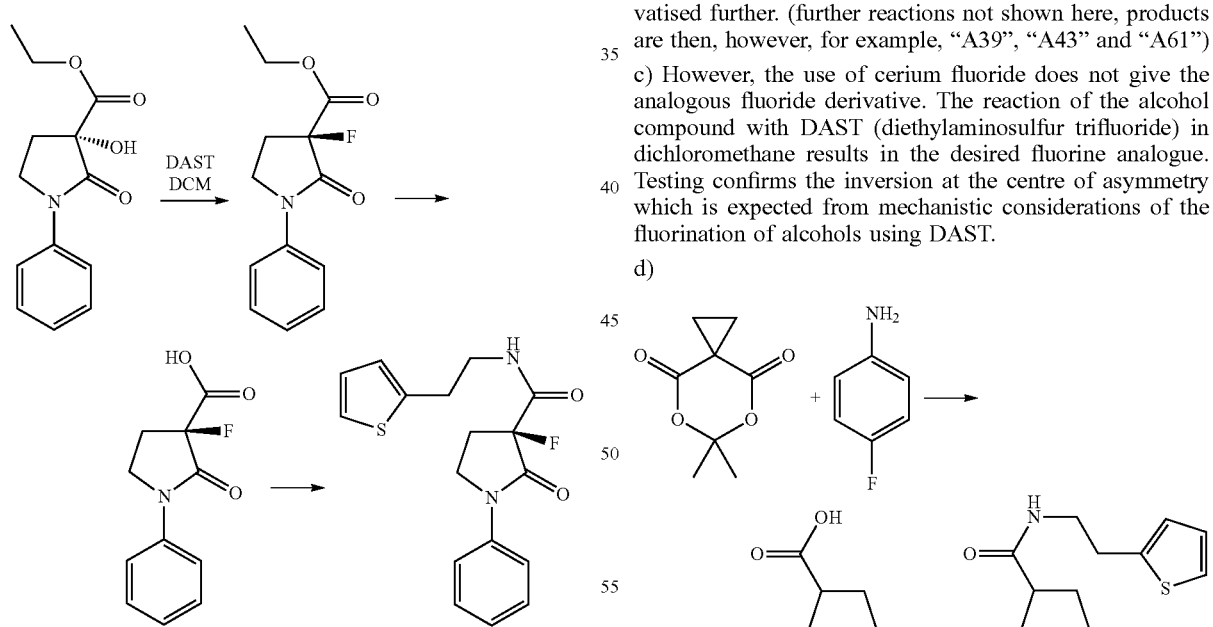

a) Route 1: The acid is converted into the corresponding amide in an amide coupling and then oxidised on the carbon between the two carboxyl groups using tertiary butyl hydroperoxide in a basic environment to give the alcohol (followed by enantiomer separation via chromatography).

b) Route 2: Alternatively, it has been found that, under the same oxidative conditions as described in route 1 for the amide, the ethyl ester of the starting acid cannot be oxidised. However, this does succeed with cerium chloride. The chlorine derivative obtained with 30% can be separated into the enantiomers analogously to the alcohols and then derivatised further. (further reactions not shown here, products are then, however, for example, "A39", "A43" and "A61")

c) However, the use of cerium fluoride does not give the analogous fluoride derivative. The reaction of the alcohol compound with DAST (diethylaminosulfur trifluoride) in dichloromethane results in the desired fluorine analogue. Testing confirms the inversion at the centre of asymmetry which is expected from mechanistic considerations of the fluorination of alcohols using DAST.

d)

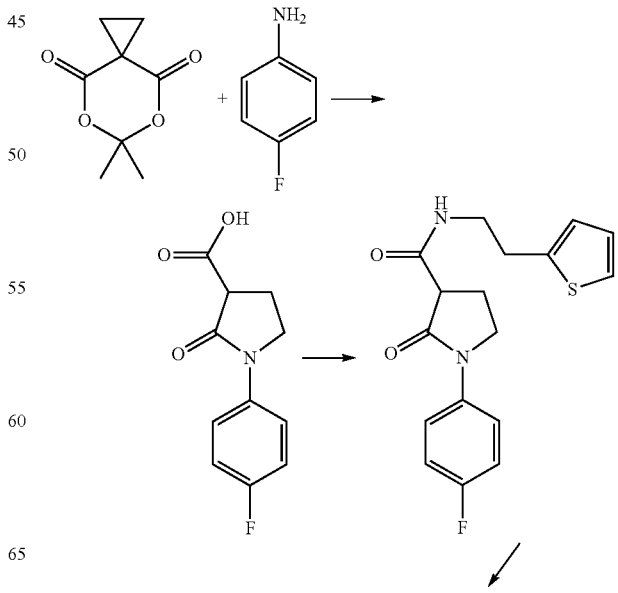

77
-continued

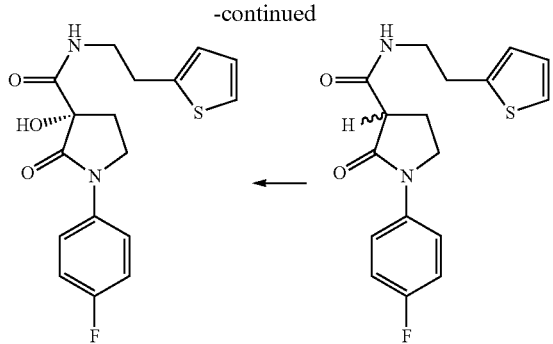

It is shown in d) how N-aryllactamcarboxylic acids can be prepared. This route can easily be carried out if the nitrogen compound is a liquid. It is found that joint melting of the starting materials, if the nitrogen-aryl compound is not liquid, is not advantageous. However, the desired product is obtained if the nitrogen-aryl compound is melted and the dicarboxylic acid ester (Meldrum's acid) is added to this melt.

e)

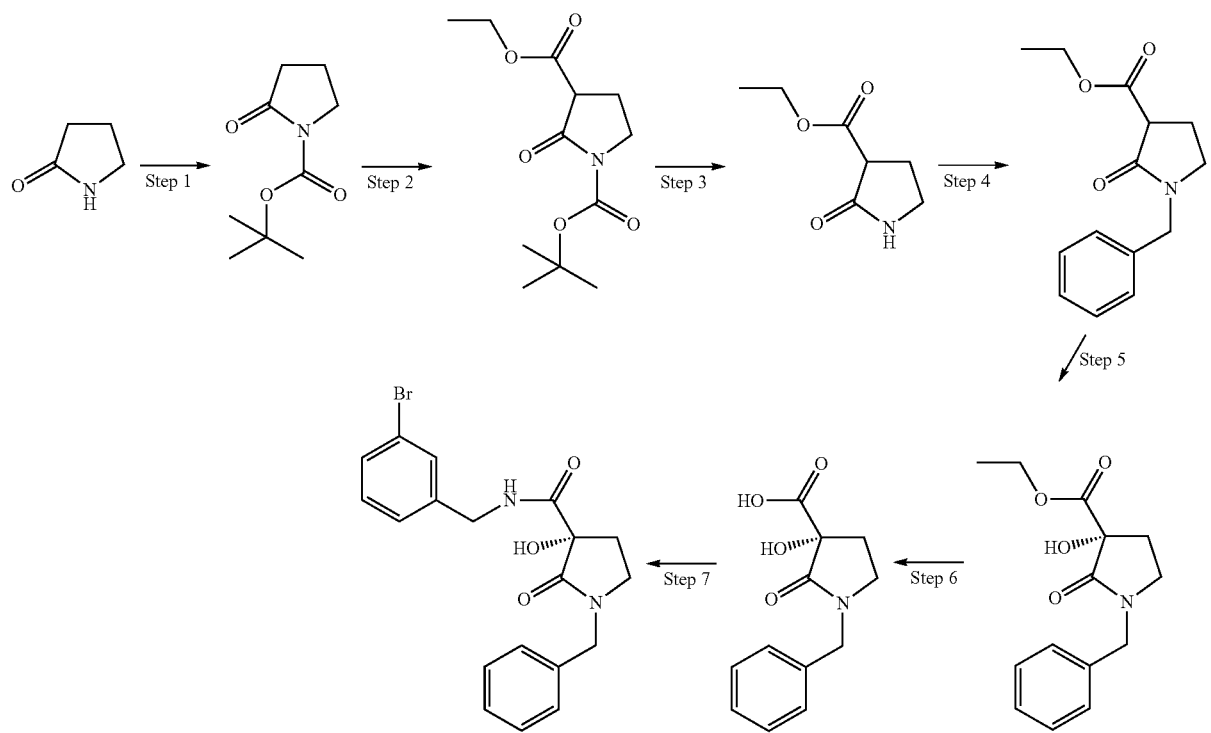

e) shows a route for the preparation of the N-alkaryllactam-carboxylic acid.

f)

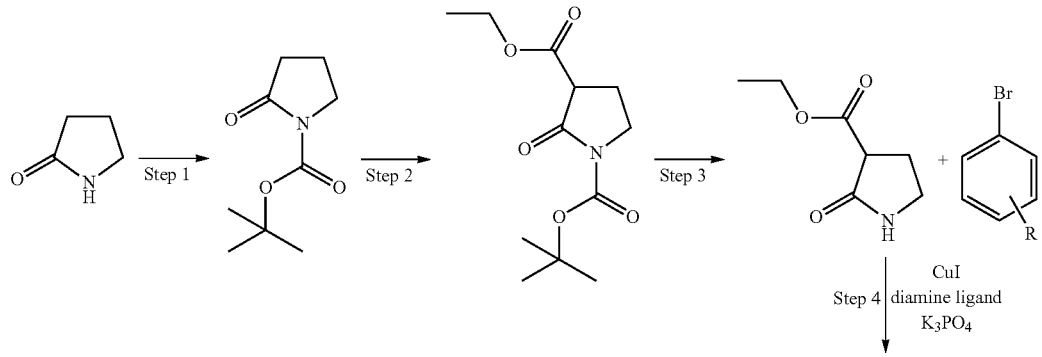

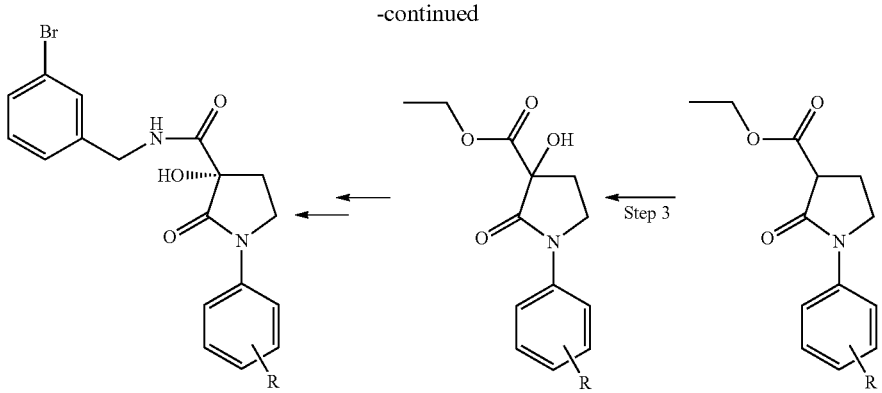

f) shows a further alternative, which is carried out in order to make available aryl radicals on the lactam nitrogen in which the analogous nitrogen compound is not a liquid. Here, the lactam nitrogen is coupled to an aryl halide, a step which is preferably catalysed by transition-metal compounds.

EXAMPLE 1

Synthesis of 3-hydroxy-1-(4-methanesulfoximinoyl-phenyl)-2-oxo-pyrrolidine-3-carboxylic acid 3-chloro-5-fluoro-benzylamide ("A64")

1.1

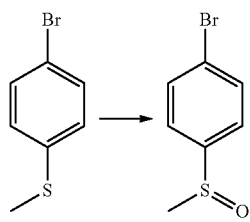

0.73 ml of a 30% H₂O₂ solution are added at 0° C. to a solution of 1 g 4-bromothioanisol in 5 ml acetic acid. The mixture is stirred for 12 h at RT and worked up with 10% NaOH solution. The aqueous phase is extracted with ethyl acetate. The organic phase is washed with saturated NaCl solution and dried over Na₂SO₄. Removal of the solvent gives 0.97 g crude product, which is used in the next step without further purification.

1.2

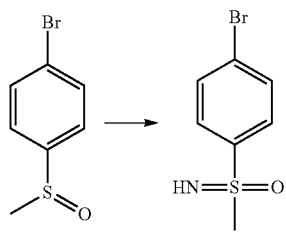

223 mg sodium azide are given dropwise at 0° C. to a solution of 900 mg 1-bromo-4-methanesulfinyl-benzene in 18 ml chloroform. The mixture is stirred at 0° for 12 h and ice water is added. Conventional work-up gives 600 mg crude product, which is used in the next step without further purification.

1.3

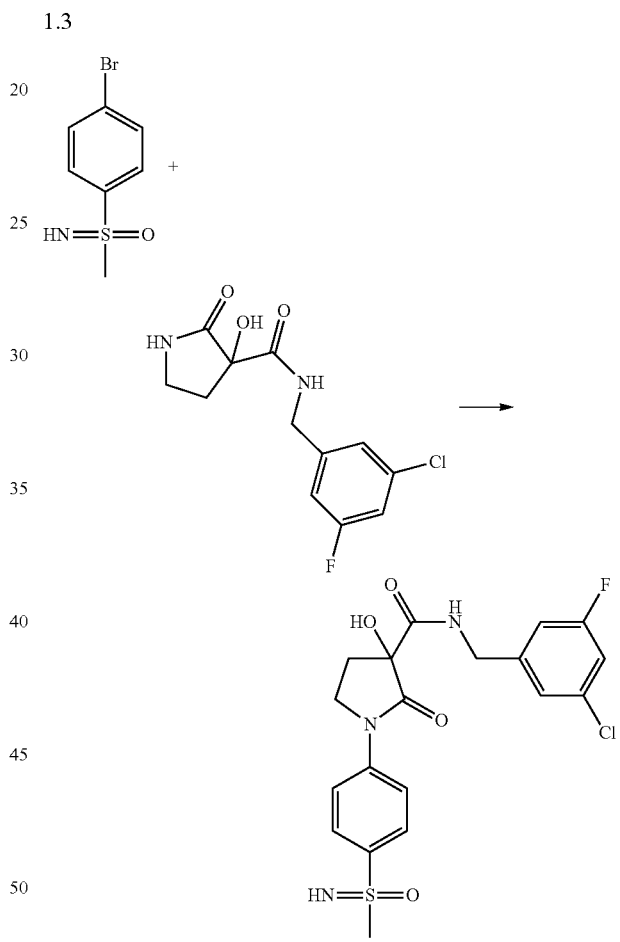

253 mg 3-hydroxy-2-oxo-pyrrolidine-3-carboxylic acid 3-chloro-5-fluoro-benzyl amide (described in WO 2013/149704), 359 mg potassium carbonate, 382 mg N',N'-dimethyl-ethane-1,2-diamine and 330 mg copper(I)iodide are added successively to a solution of 200 mg sulfoximin from step 1.2 in 12 ml degassed dioxane. The mixture is reacted for 2 h at 140° C. in a microwave oven. The mixture is filtrated over celite, and the solvents are removed in vacuo. Preparative HPLC gives 55 mg of "A64" (diastereomeric mixture);

¹H NMR 400 MHz, DMSO-d₆: δ [ppm] 8.79 (t, J=6.40 Hz, 1H), 7.90-7.96 (m, 4H), 7.26-7.29 (m, 1H), 7.20 (s, 1H), 7.10 (d, J=9.60 Hz, 1H), 6.87 (s, 1H), 4.35-4.41 (m, 1H), 4.20-4.27 (m, 2H), 3.90-3.93 (m, 2H), 3.04 (d, J=0.80 Hz, 3H), 2.58-2.62 (m, 1H), 2.12-2.19 (m, 1H).

EXAMPLE 2

Synthesis of (S)-3-Hydroxy-1-(1H-indazol-5-yl)-2-oxo-pyrrolidine-3-carboxylic acid 3,5-difluoro-benzylamide ("A75") and (R)-3-Hydroxy-1-(1H-indazol-5-yl)-2-oxo-pyrrolidine-3-carboxylic acid 3,5-difluoro-benzylamide 2.1

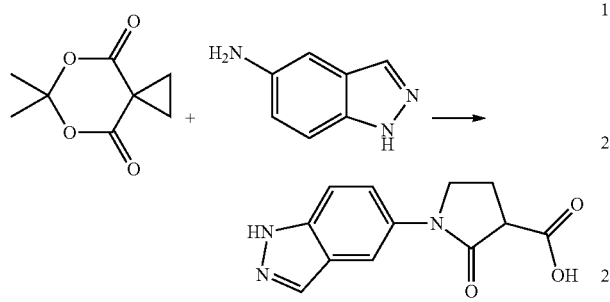

A solution of 11 g 6,6-dimethyl-5,7-dioxa-spiro[2.5]octane-4,8-dione and 7 g 5-aminoindazole in 50 ml acetonitrile and 50 ml DMF is stirred at 80° C. for 12 h. The solvents are removed and conventional work-up gives 13 g 1-(1H-indazol-5-yl)-2-oxo-pyrrolidine-3-carboxylic acid.

2.2

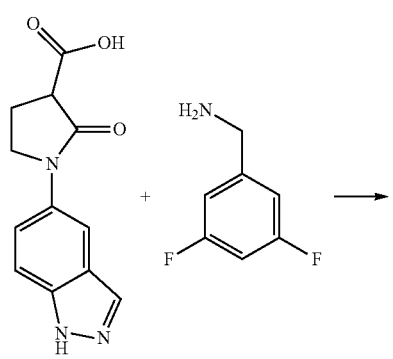

15 ml 4-Methylmorpholine and 16 g HATU (1-[Bis(dimethylamino)methylene]-1H-1,2,3-triazolo[4,5-b]pyridinium 3-oxid hexafluorophosphate) are added to a solution of 8.5 g 1-(1H-indazol-5-yl)-2-oxo-pyrrolidine-3-carboxylic acid in 20 ml DMF. The solution is stirred for 20 minutes at RT and added to a solution of 6 g 3,5-difluorobenzylamine in 20 ml DMF. The mixture is stirred at 60° C. for 2 h. Removal of the solvents and conventional work-up gives 9 g 1-(1H-indazol-5-yl)-2-oxo-pyrrolidine-3-carboxylic acid 3,5-difluoro-benzylamide.

2.3

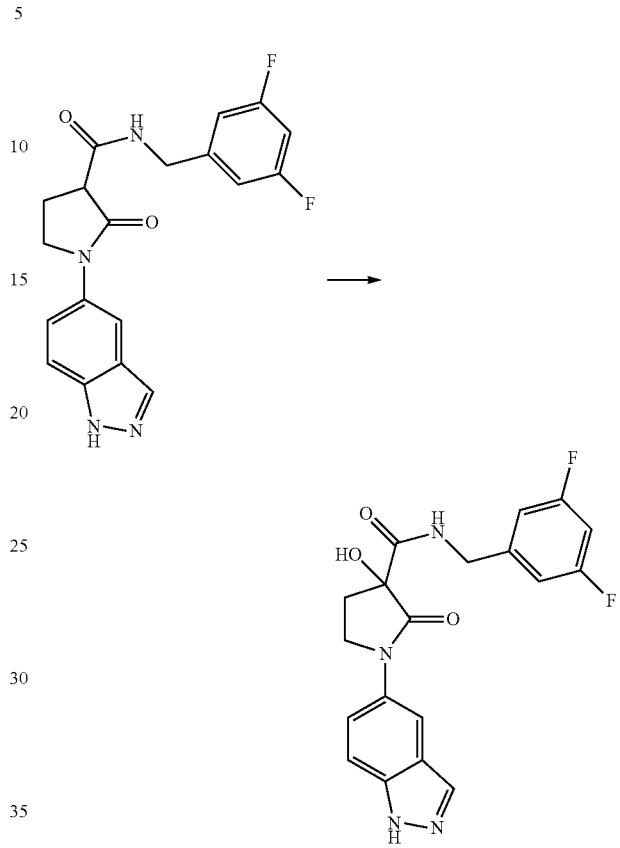

15.5 g Magnesium monoperoxyphthalate hexahydrate are added to a solution of 8.5 g 1-(1H-indazol-5-yl)-2-oxo-pyrrolidine-3-carboxylic acid 3,5-difluoro-benzylamide in 50 ml DMF. The yellow suspension is stirred at 60° C. for 12 h. After removal of the solvent and conventional work-up the residue is purified by chromatography (silica gel); yield: 5.1 g yellow oil of (S)-3-Hydroxy-1-(1H-indazol-5-yl)-2-oxo-pyrrolidine-3-carboxylic acid 3,5-difluoro-benzylamide ("A75") and (R)-3-Hydroxy-1-(1H-indazol-5-yl)-2-oxo-pyrrolidine-3-carboxylic acid 3,5-difluoro-benzylamide.

2.4

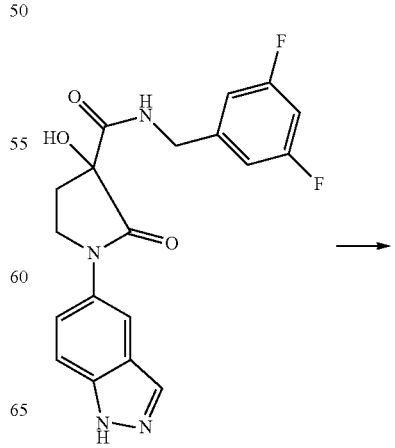

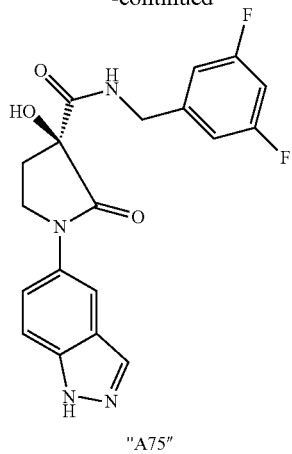

"A75"

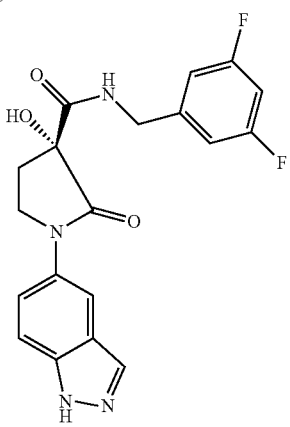

Separation of 5.1 g of the mixtures of enantiomers is performed by SF chromatography.
Column: ChiralPAK AS-H
Eluent: $CO_2$:methanol=80:20
Wave length: 220 nm
Flow: 100 ml/min.

Yield:

1.4 g (S)-3-Hydroxy-1-(1H-indazol-5-yl)-2-oxo-pyrrolidine-3-carboxylic acid 3,5-difluoro-benzylamide ("A75"), 1.3 g (R)-3-Hydroxy-1-(1H-indazol-5-yl)-2-oxo-pyrrolidine-3-carboxylic acid 3,5-difluoro-benzylamide ("A75");

"A75": LC-MS 1.776 min; [M+H$^+$] [387.1];

$^1$H NMR (500 MHz, DMSO-d$_6$) δ [ppm] 13.07 (s, 1H), 8.68 (t, J=6.4 Hz, 1H), 8.09 (d, J=10.3 Hz, 1H), 7.91 (d, J=1.6 Hz, 1H), 7.76 (dd, J=9.0, 2.0 Hz, 1H), 7.56 (t, J=7.6 Hz, 1H), 7.05 (tt, J=9.4, 2.3 Hz, 1H), 7.03-6.97 (m, 2H), 6.72 (s, 1H), 4.42 (dd, J=15.8, 6.8 Hz, 1H), 4.27 (dd, J=15.8, 6.0 Hz, 1H), 3.96-3.87 (m, 2H), 2.63 (ddd, J=12.0, 6.9, 4.9 Hz, 1H), 2.16 (dt, J=12.9, 7.5 Hz, 1H).

The following compounds are obtained analogously

| No. | Structure/name | $^1$H NMR (400 or 500 MHz, DMSO-d$_6$) δ [ppm] | LC-MS; rt; [M + H$^+$] |
|---|---|---|---|
| "A1" | (S)-3-Hydroxy-2-oxo-1-[3-(piperazine-1-sulfonyl)-phenyl]-pyrrolidine-3-carboxylic acid 3-chloro-5-fluoro-benzylamide | 500 MHz: 8.75 (t, J = 6.3 Hz, 1H), 8.25-8.15 (m, 1H), 7.92 (s, 1H), 7.90 (m, 1H), 7.70 (t, J = 8.0 Hz, 1H), 7.54 (d, J = 8.5 Hz, 1H), 7.26 (dd, J = 8.7, 2.0 Hz, 1H), 7.21 (s, 1H), 7.10 (d, J = 9.6 Hz, 1H), 4.38 (dd, J = 15.7, 6.6 Hz, 1H), 4.27 (dd, J = 15.7, 6.1 Hz, 1H), 3.98-3.89 (m, 2H), 3.52-3.40 (m, 3H), 3.00-2.89 (m, 3H), 2.83 (d, J = 4.7 Hz, 1H), 2.78-2.71 (m, 1H), 2.66-2.58 (m, 1H), 2.17 (ddd, J = 15.1, 10.2, 5.7 Hz, 1H) | 1.677 [511.1] |

| No. | Structure/name | 1H NMR (400 or 500 MHz, DMSO-d6) δ [ppm] | LC-MS; rt; [M + H+] |
|---|---|---|---|
| "A2" | 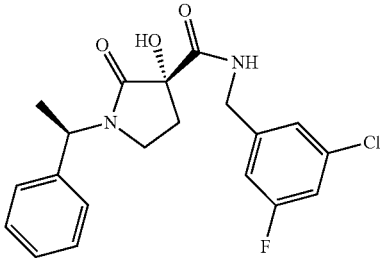<br>(S)-3-Hydroxy-2-oxo-1-((R)-1-phenyl-ethyl)-pyrrolidine-3-carboxylic acid 3-chloro-5-fluoro-benzylamide | | |
| "A3" | 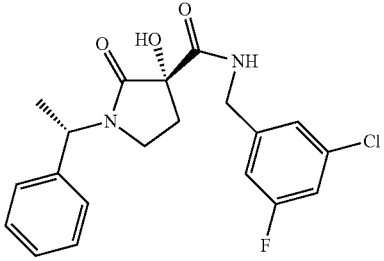<br>(S)-3-Hydroxy-2-oxo-1-((S)-1-phenyl-ethyl)-pyrrolidine-3-carboxylic acid 3-chloro-5-fluoro-benzylamide | | |
| "A4" | 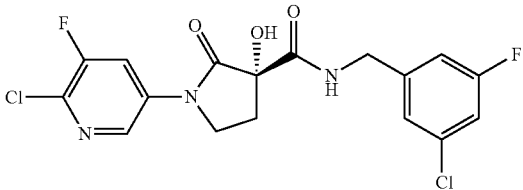<br>(S)-1-(6-Chloro-5-fluoro-pyridin-3-yl)-3-hydroxy-2-oxo-pyrrolidine-3-carboxylic acid 3-chloro-5-fluoro-benzylamide | | 2.259 [416.0] |
| "A5" | 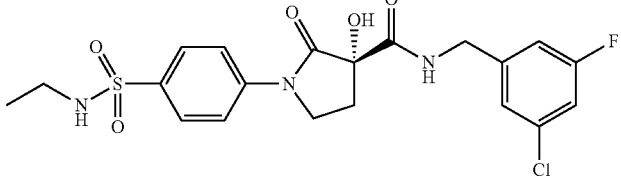<br>(S)-1-(4-Ethylsulfamoyl-phenyl)-3-hydroxy-2-oxo-pyrrolidine-3-carboxylic acid 3-chloro-5-fluoro-benzylamide | | 2.136 [470.0] |

-continued

| No. | Structure/name | $^1$H NMR (400 or 500 MHz, DMSO-$d_6$) δ [ppm] | LC-MS; rt; [M + H$^+$] |
|---|---|---|---|
| "A6" | 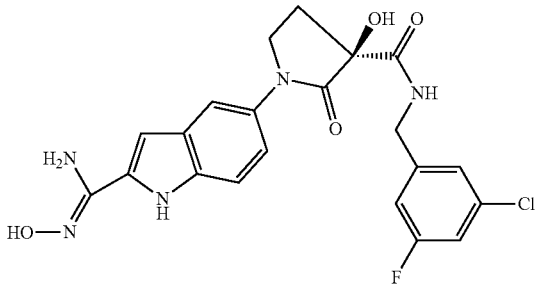<br>(S)-3-Hydroxy-1-[2-(N-hydroxycarbamimidoyl)-1H-indol-5-yl]-2-oxo-pyrrolidine-3-carboxylic acid 3-chloro-5-fluoro-benzylamide | 400 MHz: 11.08-11.04 (m, 1H), 9.58 (s, 1H), 8.65 (t, J = 6.4, 1H), 7.70 (d, J = 2.0, 1H), 7.42 (dd, J = 8.8, 2.0 1H), 7.37 (d, J = 8.8, 1H), 7.26 (dt, J = 8.7, 2.2, 1H), 7.24-7.21 (m, 1H), 7.15-7.09 (m, 1H), 6.85-6.83 (m, 1H), 6.65 (s, 1H), 5.81 (s, 2H), 4.40 (dd, J = 15.7, 6.7, 1H), 4.27 (dd, J = 15.7, 6.0, 1H), 3.91-3.85 (m, 2H), 2.65-2.57 (m, 1H), 2.13 (dt, J = 12.8, 7.5, 1H) | 1.723 [460.1] |
| "A7" | 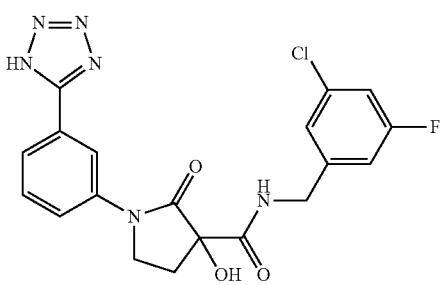<br>3-Hydroxy-2-oxo-1-[3-(1H-tetrazol-5-yl)-phenyl]-pyrrolidine-3-carboxylic acid 3-chloro-5-fluoro-benzylamide | | 1.984 [431.0] |
| "A8" | 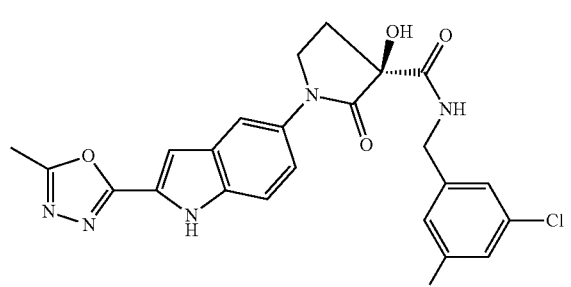<br>(S)-3-Hydroxy-1-[2-(5-methyl-[1,3,4]oxadiazol-2-yl)-1H-indol-5-yl]-2-oxo-pyrrolidine-3-carboxylic acid 3-chloro-5-fluoro-benzylamide | | 2.384 [458.1] |

| No. | Structure/name | $^1$H NMR (400 or 500 MHz, DMSO-$d_6$) δ [ppm] | LC-MS; rt; [M + H$^+$] |
|---|---|---|---|
| "A9" | 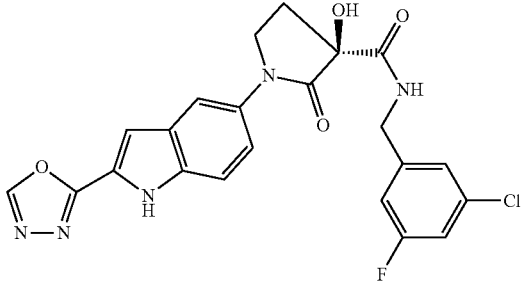<br>(S)-3-Hydroxy-1-(2-[1,3,4]oxadiazol-2-yl-1H-indol-5-yl)-2-oxo-pyrrolidine-3-carboxylic acid 3-chloro-5-fluoro-benzylamide | 500 MHz: 12.36-12.28 (m, 1H), 9.35 (s, 1H), 8.69 (t, J = 6.4, 1H), 7.87 (d, J = 2.0, 1H), 7.65 (dd, J = 8.9, 2.1, 1H), 7.53-7.47 (m, 1H), 7.27 (dt, J = 8.7, 2.2, 1H), 7.25-7.24 (m, 1H), 7.24-7.21 (m, 1H), 7.15-7.10 (m, 1H), 6.71 (s, 1H), 4.41 (dd, J = 15.7, 6.7, 1H), 4.27 (dd, J = 15.7, 6.0, 1H), 3.95-3.88 (m, 2H), 2.66-2.59 (m, 1H), 2.16 (dt, J = 12.8, 7.6, 1H) | 2.033 [470.0] |
| "A10" | 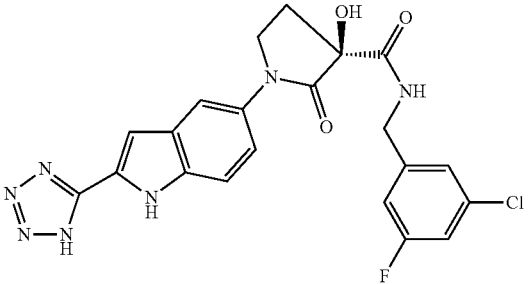<br>(S)-3-Hydroxy-2-oxo-1-[2-(1H-tetrazol-5-yl)-1H-indol-5-yl]-pyrrolidine-3-carboxylic acid 3-chloro-5-fluoro-benzylamide | 400 MHz: 17.95-15.96 (m, 1H), 12.14-12.07 (m, 1H), 8.68 (t, J = 6.4, 1H), 7.84 (d, J = 2.0, 1H), 7.59 (dd, J = 8.9, 2.1, 1H), 7.49 (d, J = 8.9, 1H), 7.27 (dt, J = 8.8, 2.2, 1H), 7.24-7.21 (m, 1H), 7.16-7.10 (m, 2H), 6.69 (s, 1H), 4.41 (dd, J = 15.8, 6.8, 1H), 4.27 (dd, J = 15.7, 6.0, 1H), 3.95-3.88 (m, 2H), 2.66-2.58 (m, 1H), 2.16 (dt, J = 12.8, 7.5, 1H) | 1.993 [470.0] |
| "A11" | 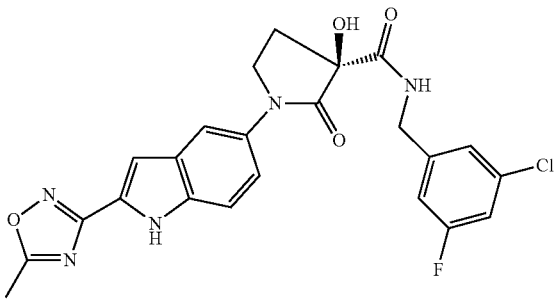<br>(S)-3-Hydroxy-1-[2-(5-methyl-[1,2,4]oxadiazol-3-yl)-1H-indol-5-yl]-2-oxo-pyrrolidine-3-carboxylic acid 3-chloro-5-fluoro-benzylamide | 400 MHz: 12.03 (s, 1H), 8.67 (t, J = 6.4, 1H), 7.82 (d, J = 2.0, 1H), 7.59 (dd, J = 8.9, 2.1, 1H), 7.47 (d, J = 8.9, 1H), 7.27 (dt, J = 8.7, 2.2, 1H), 7.24-7.21 (m, 1H), 7.16-7.09 (m, 2H), 6.69 (s, 1H), 4.41 (dd, J = 15.7, 6.7, 1H), 4.27 (dd, J = 15.7, 6.0, 1H), 3.90 (t, J = 6.7, 2H), 2.68 (s, 3H), 2.62 (dt, J = 12.1, 5.8, 1H), 2.20-2.11 (m, 1H) | 2.181 [484.1] |
| "A12" | 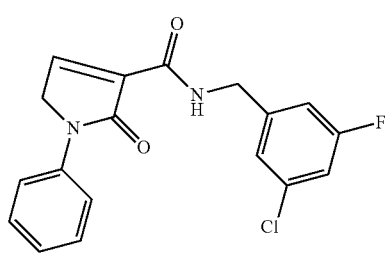<br>2-Oxo-1-phenyl-2,5-dihydro-1H-pyrrole-3-carboxylic acid 3-chloro-5-fluoro-benzylamide | | |

| No. | Structure/name | ¹H NMR (400 or 500 MHz, DMSO-d₆) δ [ppm] | LC-MS; rt; [M + H⁺] |
|---|---|---|---|
| "A13" | 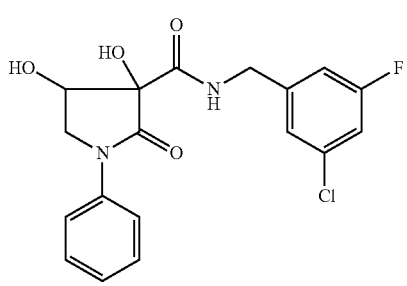<br>3,4-Dihydroxy-2-oxo-1-phenyl-pyrrolidine-3-carboxylic acid 3-chloro-5-fluoro-benzylamide | | |
| "A14" | 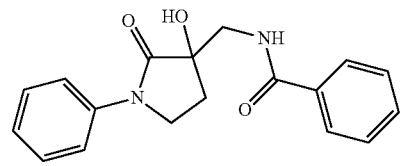<br>N-(3-Hydroxy-2-oxo-1-phenyl-pyrrolidin-3-ylmethyl)-benzamide | | |
| "A15" | 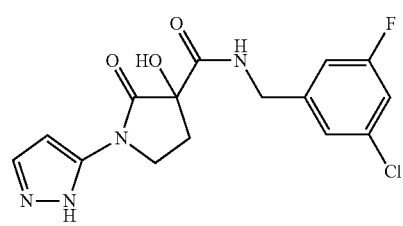<br>3-Hydroxy-2-oxo-1-(2H-pyrazol-3-yl)-pyrrolidine-3-carboxylic acid 3-chloro-5-fluoro-benzylamide | | |
| "A16" | 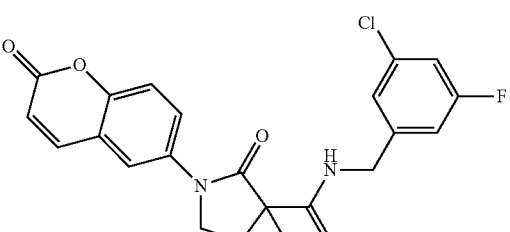<br>3-Hydroxy-2-oxo-1-(2-oxo-2H-chromen-6-yl)-pyrrolidine-3-carboxylic acid 3-chloro-5-fluoro-benzylamide | | 2.059 [431.05] |

| No. | Structure/name | ¹H NMR (400 or 500 MHz, DMSO-d₆) δ [ppm] | LC-MS; rt; [M + H⁺] |
|---|---|---|---|
| "A17" | 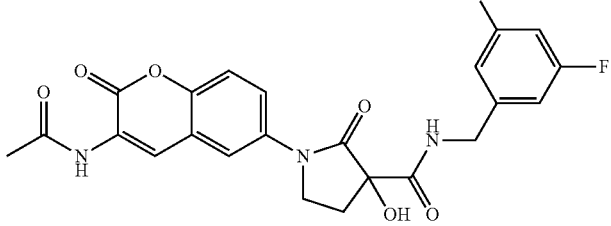<br>1-(3-Acetylamino-2-oxo-2H-chromen-6-yl)-3-hydroxy-2-oxo-pyrrolidine-3-carboxylic acid 3-chloro-5-fluoro-benzylamide | | 2.060 [488.1] |
| "A18" | 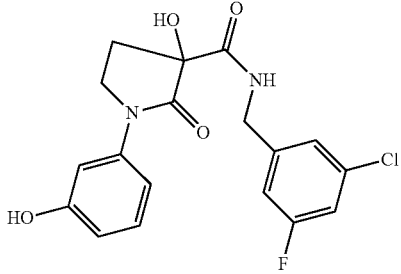<br>3-Hydroxy-1-(3-hydroxy-phenyl)-2-oxo-pyrrolidine-3-carboxylic acid 3-chloro-5-fluoro-benzylamide | 400 MHz: 9.50 (s, 1H), 8.67 (t, J = 6.4 Hz, 1H), 7.26 (td, J = 5.4, 2.7 Hz, 2H), 7.21 (s, 1H), 7.17 (t, J = 8.1 Hz, 1H), 7.10 (d, J = 9.6 Hz, 1H), 7.05-7.01 (m, 1H), 6.70 (s, 1H), 6.61-6.55 (m, 1H), 4.39 (dd, J = 15.7, 6.7 Hz, 1H), 4.25 (dd, J = 15.7, 6.0 Hz, 1H), 3.80 (dd, J = 7.4, 6.2 Hz, 2H), 2.62-2.53 (m, 1H), 2.11 (dt, J = 13.0, 7.6 Hz, 1H) | 1.997 [379.05] |
| "A19" | 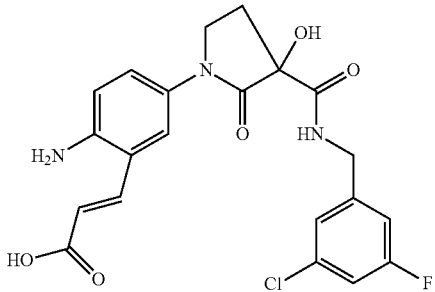<br>(E)-3-{2-Amino-5-[3-(3-chloro-5-fluoro-benzylcarbamoyl)-3-hydroxy-2-oxo-pyrrolidin-1-yl]-phenyl}-acrylic acid | | |
| "A20" | 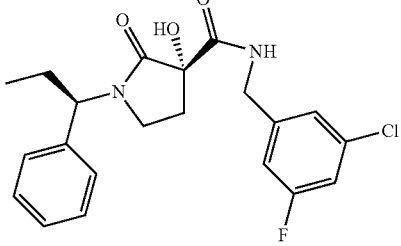<br>(S)-3-Hydroxy-2-oxo-1-((R)-1-phenyl-propyl)-pyrrolidine-3-carboxylic acid 3-chloro-5-fluoro-benzylamide | | |

| No. | Structure/name | ¹H NMR (400 or 500 MHz, DMSO-d₆) δ [ppm] | LC-MS; rt; [M + H⁺] |
|---|---|---|---|
| "A21" | 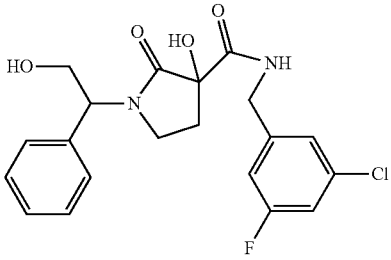<br>3-Hydroxy-1-(2-hydroxy-1-phenyl-ethyl)-2-oxo-pyrrolidine-3-carboxylic acid 3-chloro-5-fluoro-benzylamide | | |
| "A22" | 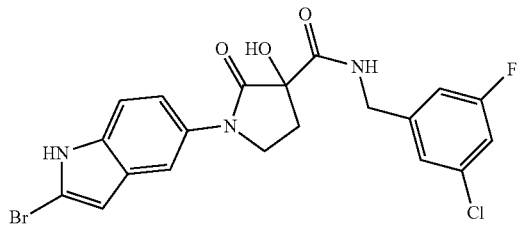<br>1-(2-Bromo-1H-indol-5-yl)-3-hydroxy-2-oxo-pyrrolidine-3-carboxylic acid 3-chloro-5-fluoro-benzylamide | | |
| "A23" | 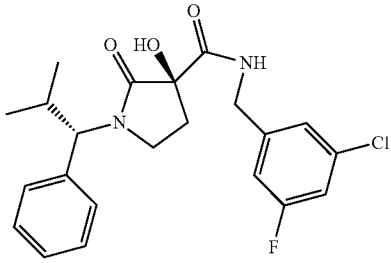<br>(R)-3-Hydroxy-1-((S)-2-methyl-1-phenyl-propyl)-2-oxo-pyrrolidine-3-carboxylic acid 3-chloro-5-fluoro-benzylamide | | |
| "A24" | 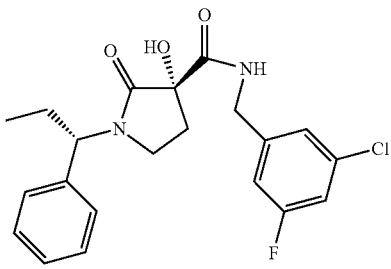<br>(S)-3-Hydroxy-2-oxo-1-((S)-1-phenyl-propyl)-pyrrolidine-3-carboxylic acid 3-chloro-5-fluoro-benzylamide | | |

| No. | Structure/name | ¹H NMR (400 or 500 MHz, DMSO-d₆) δ [ppm] | LC-MS; rt; [M + H⁺] |
|---|---|---|---|
| "A25" | 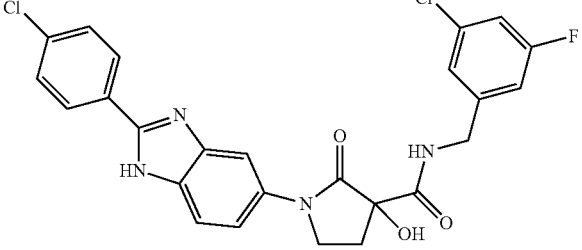<br>1-[2-(4-Chloro-phenyl)-1H-benzoimidazol-5-yl]-3-hydroxy-2-oxo-pyrrolidine-3-carboxylic acid 3-chloro-5-fluoro-benzylamide | | 2.066 [513.0] |
| "A26" | 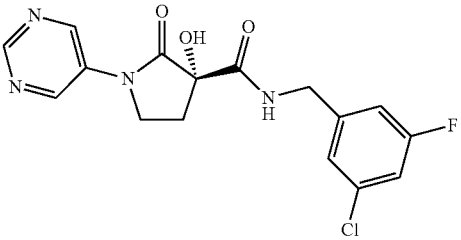<br>(S)-3-Hydroxy-2-oxo-1-pyrimidin-5-yl-pyrrolidine-3-carboxylic acid 3-chloro-5-fluoro-benzamide | | 1.816 [365.0] |
| "A27" | 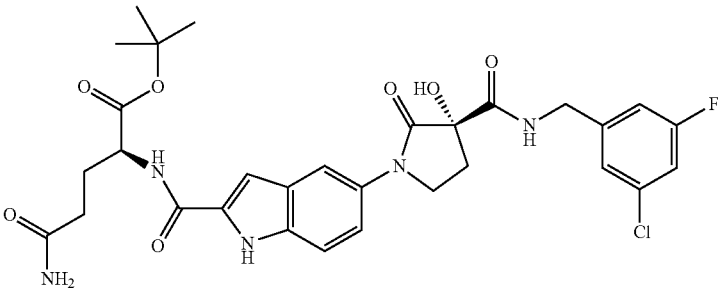<br>(S)-4-Carbamoyl-2-({5-[(S)-3-(3-chloro-5-fluoro-benzylcarbamoyl)-3-hydroxy-2-oxo-pyrrolidin-1-yl]-1H-indole-2-carbonyl}-amino)-butyric acid tert-butyl ester | 500 MHz: 11.67-11.61 (m, 1H), 8.72 (d, J = 7.3, 1H), 8.68 (t, J = 6.4, 1H), 7.81 (d, J = 2.1, 1H), 7.54 (dd, J = 8.9, 2.1, 1H), 7.43 (d, J = 8.9, 1H), 7.37-7.30 (m, 1H), 7.26 (dt, J = 8.8, 2.2, 1H), 7.24-7.20 (m, 2H), 7.15-7.09 (m, 1H), 6.81 (s, 1H), 6.68 (s, 1H), 4.41 (dd, J = 15.8, 6.8, 1H), 4.35-4.22 (m, 2H), 3.94-3.85 (m, 2H), 2.66-2.57 (m, 1H), 2.30-2.18 (m, 2H), 2.14 (dt, J = 12.8, 7.6, 1H), 2.11-2.01 (m, 1H), 1.98-1.87 (m, 1H), 1.43 (s, 9H) | 2.115 [630.1] |
| "A28" | 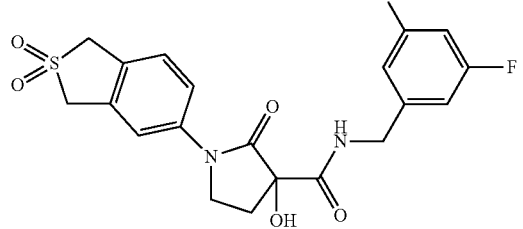<br>1-(2,2-Dioxo-2,3-dihydro-1H-2l6-benzo[c]thiophen-5-yl)-3-hydroxy-2-oxo-pyrrolidine-3-carboxylic acid 3-chloro-5-fluoro-benzylamide | | 2.002 [453.0] |

| No. | Structure/name | ¹H NMR (400 or 500 MHz, DMSO-d₆) δ [ppm] | LC-MS; rt; [M + H⁺] |
|---|---|---|---|
| "A29" | 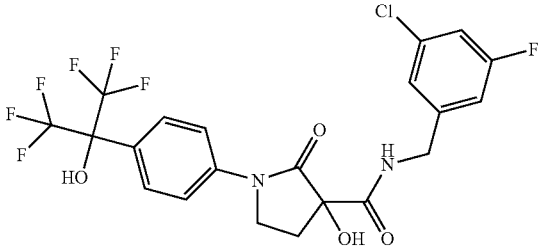<br>3-Hydroxy-2-oxo-1-[4-(2,2,2-trifluoro-1-hydroxy-1-trifluoromethyl-ethyl)-phenyl]-pyrrolidine-3-carboxylic acid 3-chloro-5-fluoro-benzylamide | 400 MHz:<br>8.75 (s, 1H), 8.73 (t, J = 6.3 Hz, 1H), 7.86 (d, J = 9.0 Hz, 2H), 7.71 (d, J = 8.7 Hz, 2H), 7.26 (ddd, J = 11.5, 6.8, 4.7 Hz, 1H), 7.21 (s, 1H), 7.10 (d, J = 9.6 Hz, 1H), 6.83 (s, 1H), 4.39 (dd, J = 15.7, 6.7 Hz, 1H), 4.26 (dd, J = 15.7, 6.0 Hz, 1H), 3.90 (t, J = 6.8 Hz, 2H), 2.65-2.57 (m, 1H), 2.16 (dt, J = 13.0, 7.6 Hz, 1H) | 2.390<br>[529.95] |
| "A30" | 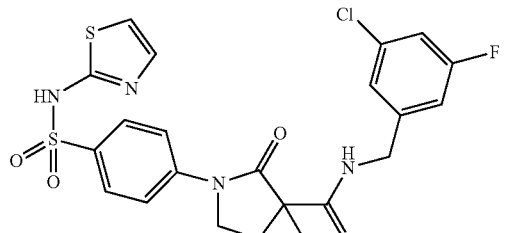<br>3-Hydroxy-2-oxo-1-[4-(thiazol-2-ylsulfamoyl)-phenyl]-pyrrolidine-3-carboxylic acid 3-chloro-5-fluoro-benzylamide | 500 MHz:<br>12.71 (s, 1H), 8.73 (t, J = 6.4 Hz, 1H), 7.88-7.85 (m, 2H), 7.84-7.80 (m, 2H), 7.26 (dt, J = 8.8, 2.1 Hz, 1H), 7.24 (d, J = 4.6 Hz, 1H), 7.20 (s, 1H), 7.09 (d, J = 9.6 Hz, 1H), 6.81 (t, J = 2.2 Hz, 2H), 4.38 (dd, J = 15.7, 6.7 Hz, 1H), 4.25 (dd, J = 15.7, 6.0 Hz, 1H), 3.95-3.82 (m, 2H), 2.65-2.55 (m, 1H), 2.15 (dt, J = 13.0, 7.7 Hz, 1H). | 1.956<br>[524.90] |
| "A31" | 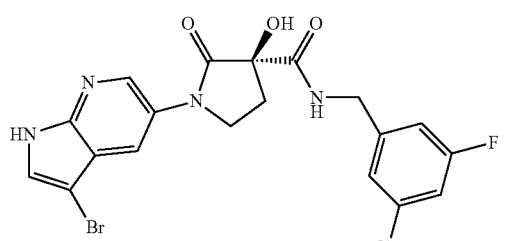<br>(R)-1-(3-Bromo-1H-pyrrolo[2,3-b]pyridin-5-yl)-3-hydroxy-2-oxo-pyrrolidine-3-carboxylic acid 3-chloro-5-fluoro-benzylamide | | |
| "A32" | 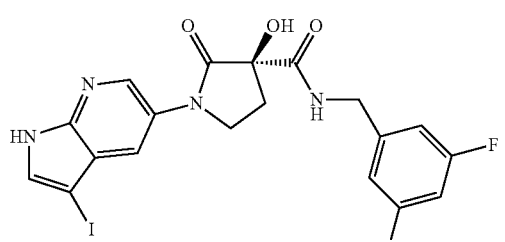<br>(R)-3-Hydroxy-1-(3-iodo-1H-pyrrolo[2,3-b]pyridin-5-yl)-2-oxo-pyrrolidine-3-carboxylic acid 3-chloro-5-fluoro-benzylamide | | |

| No. | Structure/name | ¹H NMR (400 or 500 MHz, DMSO-d₆) δ [ppm] | LC-MS; rt; [M + H⁺] |
|---|---|---|---|
| "A33" | 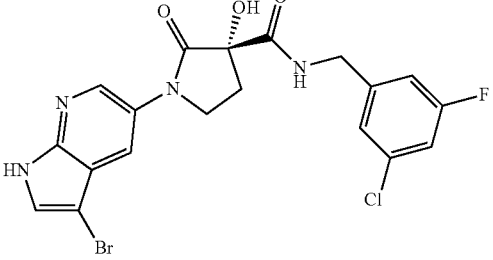<br>(S)-1-(3-Bromo-1H-pyrrolo[2,3-b]pyridin-5-yl)-3-hydroxy-2-oxo-pyrrolidine-3-carboxylic acid 3-chloro-5-fluoro-benzylamide | 500 MHz: 12.15-12.11 (m, 1H), 8.72 (t, J = 6.4, 1H), 8.55 (d, J = 2.4, 1H), 8.11 (d, J = 2.3, 1H), 7.76 (d, J = 2.6, 1H), 7.26 (dt, J = 8.8, 2.2, 1H), 7.24-7.21 (m, 1H), 7.14-7.10 (m, 1H), 6.77 (s, 1H), 4.41 (dd, J = 15.7, 6.7, 1H), 4.28 (dd, J = 15.7, 6.0, 1H), 4.02-3.92 (m, 2H), 2.68-2.62 (m, 1H), 2.22-2.15 (m, 1H) | 2.137 [482.9] |
| "A34" | 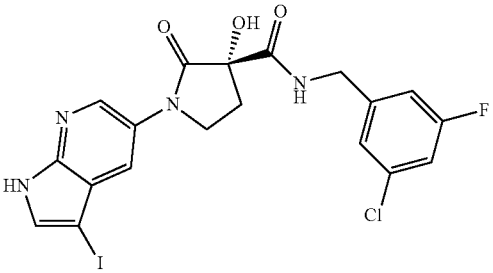<br>(S)-3-Hydroxy-1-(3-iodo-1H-pyrrolo[2,3-b]pyridin-5-yl)-2-oxo-pyrrolidine-3-carboxylic acid 3-chloro-5-fluoro-benzylamide | 500 MHz: 12.21-12.12 (m, 1H), 8.72 (t, J = 6.4, 1H), 8.48 (d, J = 2.4, 1H), 8.00-7.95 (m, 1H), 7.75 (d, J = 2.6, 1H), 7.26 (dt, J = 8.7, 2.2, 1H), 7.24-7.21 (m, 1H), 7.15-7.09 (m, 1H), 6.77 (s, 1H), 4.41 (dd, J = 15.7, 6.7, 1H), 4.28 (dd, J = 15.7, 6.1, 1H), 4.00-3.92 (m, 2H), 2.69-2.60 (m, 1H), 2.24-2.15 (m, 1H) | 2.158 [528.90] |
| "A35" | 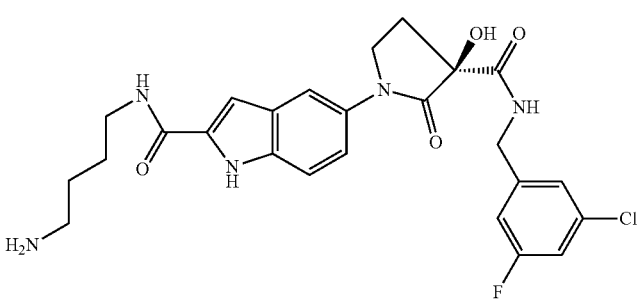<br>5-[(S)-3-(3-Chloro-5-fluoro-benzylcarbamoyl)-3-hydroxy-2-oxo-pyrrolidin-1-yl]-1H-indole-2-carboxylic acid (4-amino-butyl)-amide | 500 MHz: 11.81-11.58 (m, 1H), 8.69 (t, J = 6.4, 1H), 8.59 (t, J = 5.8, 1H), 8.38 (s, 1H), 7.78 (d, J = 2.1, 1H), 7.52 (dd, J = 8.9, 2.1, 1H), 7.43 (d, J = 8.9, 1H), 7.26 (dt, J = 8.7, 2.2, 1H), 7.24-7.21 (m, 1H), 7.15-7.08 (m, 2H), 4.40 (dd, J = 15.8, 6.7, 1H), 4.26 (dd, J = 15.8, 6.0, 1H), 3.92-3.86 (m, 2H), 3.33-3.27 (m, 2H), 2.81-2.75 (m, 2H), 2.65-2.48 (m, 1H), 2.14 (dt, J = 12.8, 7.5, 1H), 1.64-1.44 (m, 4H) | 1.611 [516.10] |

-continued

| No. | Structure/name | $^1$H NMR (400 or 500 MHz, DMSO-$d_6$) δ [ppm] | LC-MS; rt; [M + H$^+$] |
|---|---|---|---|
| "A36" | 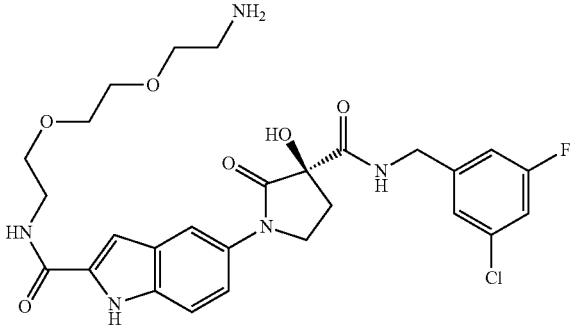<br>5-[(R)-3-(3-Chloro-5-fluoro-benzylcarbamoyl)-3-hydroxy-2-oxo-pyrrolidin-1-yl]-1H-indole-2-carboxylic acid {2-[2-(2-amino-ethoxy)-ethoxy]-ethyl}-amide | 500 MHz: 11.57 (s, 1H), 8.69 (t, J = 6.4, 1H), 8.60 (t, J = 5.7, 1H), 8.33 (s, 1H), 7.78 (d, J = 2.0, 1H), 7.53 (dd, J = 8.9, 2.1, 1H), 7.43 (d, J = 8.9, 1H), 7.26 (dt, J = 8.7, 2.2, 1H), 7.24-7.21 (m, 1H), 7.15-7.09 (m, 2H), 4.40 (dd, J = 15.8, 6.8, 1H), 4.26 (dd, J = 15.8, 6.0, 1H), 3.93-3.85 (m, 2H), 3.61-3.54 (m, 6H), 3.51 (t, J = 5.5, 2H), 3.45 (q, J = 5.8, 2H), 2.83 (t, J = 5.5, 2H), 2.61 (dt, J = 12.8, 5.8, 1H), 2.14 (dt, J = 12.8, 7.5, 1H) | 1.611 [576.1] |
| "A37" | 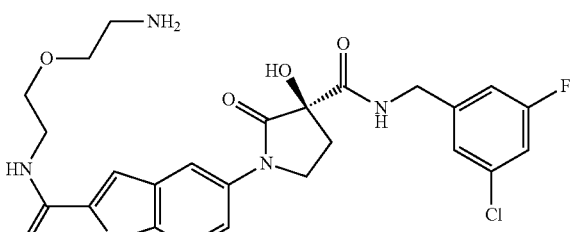<br>5-[(R)-3-(3-Chloro-5-fluoro-benzylcarbamoyl)-3-hydroxy-2-oxo-pyrrolidin-1-yl]-1H-indole-2-carboxylic acid [2-(2-amino-ethoxy)-ethyl]-amide | 500 MHz: 12.41-11.26 (m, 1H), 8.65 (dt, J = 32.8, 6.0, 2H), 8.32 (s, 1H), 7.78 (d, J = 2.0, 1H), 7.53 (dd, J = 8.9, 2.1, 1H), 7.43 (d, J = 8.9, 1H), 7.26 (dt, J = 8.7, 2.2, 1H), 7.23-7.20 (m, 1H), 7.16-7.08 (m, 2H), 7.00-6.25 (m, 2H), 4.40 (dd, J = 15.8, 6.8, 1H), 4.26 (dd, J = 15.7, 6.0, 1H), 3.92-3.86 (m, 2H), 3.61-3.56 (m, 4H), 3.52-3.46 (m, 2H), 2.92 (t, J = 5.3, 2H), 2.61 (dt, J = 12.8, 5.8, 1H), 2.14 (dt, J = 12.9, 7.5, 1H) | 1.536 [532.1] |
| "A38" | 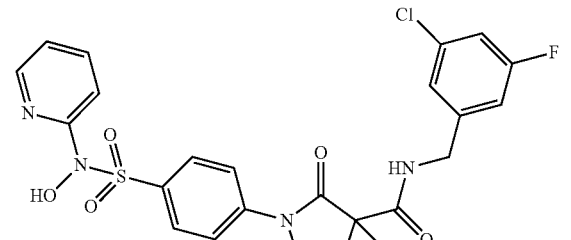<br>3-Hydroxy-1-[4-(hydroxy-pyridin-2-yl-sulfamoyl)-phenyl]-2-oxo-pyrrolidine-3-carboxylic acid 3-chloro-5-fluoro-benzylamide | 500 MHz: 8.72 (t, J = 6.4 Hz, 1H), 8.25 (dd, J = 6.8, 1.4 Hz, 1H), 7.95 (s, 1H), 7.92-7.88 (m, 2H), 7.87-7.83 (m, 2H), 7.57 (ddd, J = 8.8, 7.3, 3.8 Hz, 1H), 7.43 (dd, J = 8.9, 1.5 Hz, 1H), 7.26 (dt, J = 8.8, 2.1 Hz, 1H), 7.19 (s, 1H), 7.12-7.06 (m, 1H), 6.83 (d, J = 24.8 Hz, 1H), 6.77 (td, J = 7.0, 1.7 Hz, 1H), 4.38 (dd, J = 15.7, 6.7 Hz, 1H), 4.25 (dd, J = 15.7, 6.0 Hz, 1H), 3.93-3.84 (m, 2H), 2.74-2.72 (m, 2H), 2.59 (ddd, J = 12.7, 7.1, 4.6 Hz, 1H), 2.14 (dt, J = 13.0, 7.7 Hz, 1H) | 1.972 [535.0] |

| No. | Structure/name | ¹H NMR (400 or 500 MHz, DMSO-d₆) δ [ppm] | LC-MS; rt; [M + H⁺] |
|---|---|---|---|
| "A39" | 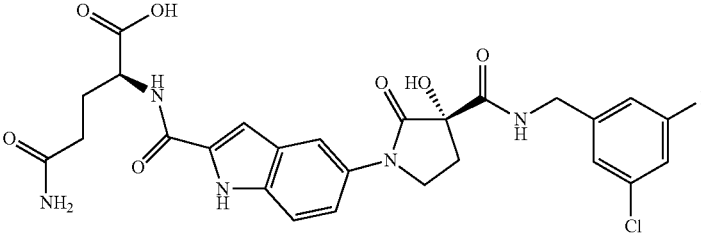<br>(S)-4-Carbamoyl-2-({5-[(S)-3-(3-chloro-5-fluoro-benzylcarbamoyl)-3-hydroxy-2-oxo-pyrrolidin-1-yl]-1H-indole-2-carbonyl}-amino)-butyric acid | 500 MHz: 12.63 (s, 1H), 11.61 (d, J = 2.2, 1H), 8.72-8.64 (m, 2H), 7.81 (d, J = 2.0, 1H), 7.54 (dd, J = 8.9, 2.1, 1H), 7.44 (d, J = 8.9, 1H), 7.32 (s, 1H), 7.25 (dt, J = 8.7, 2.2, 1H), 7.23-7.21 (m, 2H), 7.15-7.09 (m, 1H), 6.79 (s, 1H), 6.68 (s, 1H), 4.44-4.35 (m, 2H), 4.27 (dd, J = 15.7, 6.0, 1H), 3.93-3.87 (m, 2H), 2.65-2.58 (m, 1H), 2.26-2.21 (m, 2H), 2.18-2.07 (m, 2H), 1.99-1.89 (m, 1H) | 1.833 [574.0] |
| "A40" | 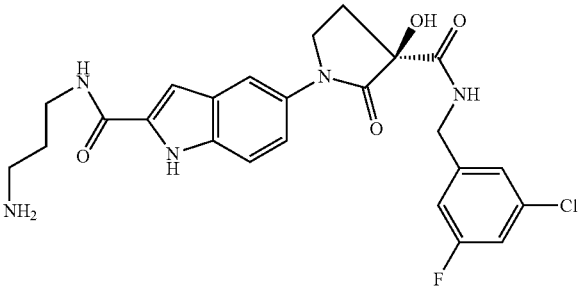<br>5-[(S)-3-(3-Chloro-5-fluoro-benzylcarbamoyl)-3-hydroxy-2-oxo-pyrrolidin-1-yl]-1H-indole-2-carboxylic acid (3-amino-propyl)-amide | 500 MHz: 11.70 (s, 1H), 8.73 (t, J = 5.8, 1H), 8.69 (t, J = 6.4, 1H), 8.36 (s, 1H), 7.79 (d, J = 2.1, 1H), 7.53 (dd, J = 8.9, 2.1, 1H), 7.43 (d, J = 8.9, 1H), 7.26 (dt, J = 8.7, 2.2, 1H), 7.24-7.20 (m, 1H), 7.14-7.10 (m, 2H), 4.40 (dd, J = 15.7, 6.8, 1H), 4.26 (dd, J = 15.8, 6.0, 1H), 3.93-3.85 (m, 2H), 3.38-3.33 (m, 2H), 2.82 (t, J = 7.3, 2H), 2.64-2.57 (m, 1H), 2.18-2.11 (m, 1H), 1.79 (p, J = 6.9, 2H) | 1.601 [502.0] |
| "A41" | 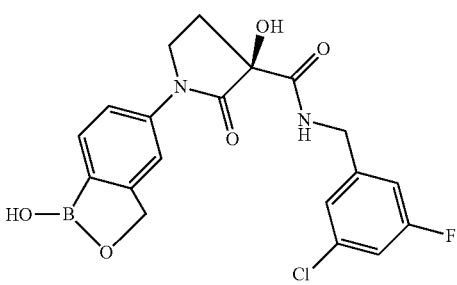<br>(S)-3-Hydroxy-1-(1-hydroxy-1,3-dihydro-benzo[c][1,2]oxaborol-5-yl)-2-oxo-pyrrolidine-3-carboxylic acid 3-chloro-5-fluoro-benzylamide | | |

| No. | Structure/name | ¹H NMR (400 or 500 MHz, DMSO-d$_6$) δ [ppm] | LC-MS; rt; [M + H⁺] |
|---|---|---|---|
| "A42" | 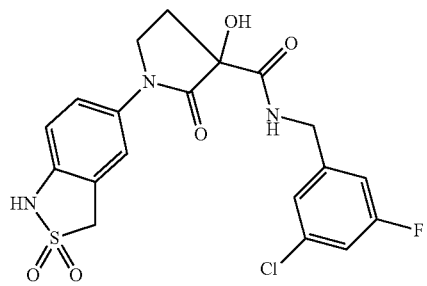<br>1-(2,2-Dioxo-2,3-dihydro-1H-2l6-benzo[c]isothiazol-5-yl)-3-hydroxy-2-oxo-pyrrolidine-3-carboxylic acid 3-chloro-5-fluoro-benzylamide | | |
| "A43" | 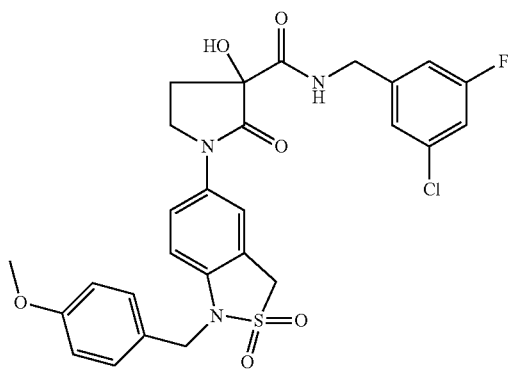<br>3-Hydroxy-1-[1-(4-methoxy-benzyl)-2,2-dioxo-2,3-dihydro-1H-2l6-benzo[c]isothiazol-5-yl]-2-oxo-pyrrolidine-3-carboxylic acid 3-chloro-5-fluoro-benzylamide | | |
| "A44" | 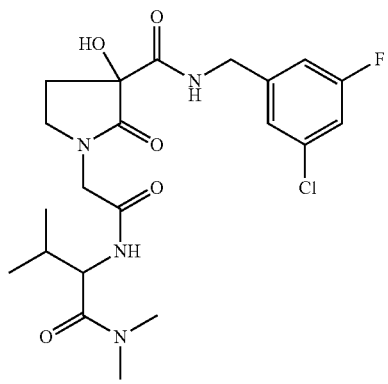<br>1-[(1-Dimethylcarbamoyl-2-methyl-propylcarbamoyl)-methyl]-3-hydroxy-2-oxo-pyrrolidine-3-carboxylic acid 3-chloro-5-fluoro-benzylamide | | |

| No. | Structure/name | $^1$H NMR (400 or 500 MHz, DMSO-$d_6$) δ [ppm] | LC-MS; rt; [M + H$^+$] |
|---|---|---|---|
| "A46" | 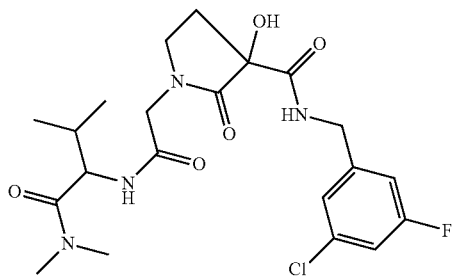<br>1-[(1-Dimethylcarbamoyl-2-methyl-propylcarbamoyl)-methyl]-3-hydroxy-2-oxo-pyrrolidine-3-carboxylic acid 3-chloro-5-fluoro-benzylamide | | |
| "A47" | 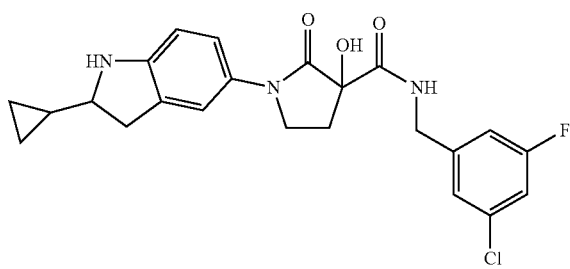<br>1-(2-Cyclopropyl-2,3-dihydro-1H-indol-5-yl)-3-hydroxy-2-oxo-pyrrolidine-3-carboxylic acid 3-chloro-5-fluoro-benzylamide | | |
| "A48" | 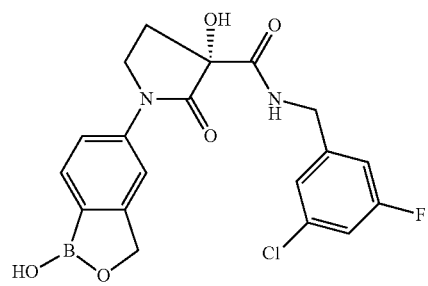<br>(R)-3-Hydroxy-1-(1-hydroxy-1,3-dihydro-benzo[c][1,2]oxaborol-5-yl)-2-oxo-pyrrolidine-3-carboxylic acid 3-chloro-5-fluoro-benzylamide | | |

-continued

| No. | Structure/name | $^1$H NMR (400 or 500 MHz, DMSO-$d_6$) δ [ppm] | LC-MS; rt; [M + H$^+$] |
|---|---|---|---|
| "A49" | 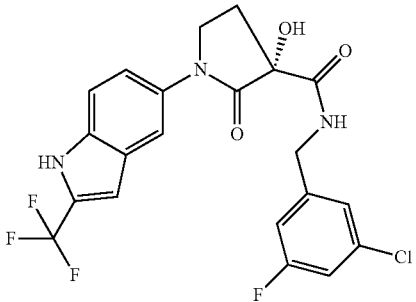<br>(R)-3-Hydroxy-2-oxo-1-(2-trifluoromethyl-1H-indol-5-yl)-pyrrolidine-3-carboxylic acid 3-chloro-5-fluoro-benzylamide | | 2.335 [470.0] |
| "A50" | 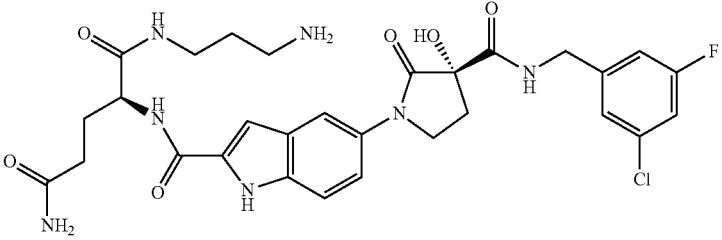<br>(S)-2-({5-[(S)-3-(3-Chloro-5-fluoro-benzylcarbamoyl)-3-hydroxy-2-oxo-pyrrolidin-1-yl]-1H-indole-2-carbonyl}-amino)-pentanedioic acid 5-amide 1-[(3-amino-propyl)-amide] | 500 MHz: 11.69 (s, 1H), 8.74-8.64 (m, 2H), 8.35 (s, 1H), 8.17 (t, J = 5.9, 1H), 7.81 (dd, J = 14.2, 2.1, 1H), 7.59-7.52 (m, 1H), 7.48-7.41 (m, 1H), 7.35 (s, 1H), 7.26 (dt, J = 8.7, 2.2, 1H), 7.24-7.20 (m, 2H), 7.15-7.10 (m, 1H), 6.78 (s, 1H), 4.41 (dd, J = 15.9, 7.0, 1H), 4.37-4.33 (m, 1H), 4.26 (dd, J = 15.8, 6.0 1H), 3.94-3.86 (m, 2H), 3.18-3.13 (m, 2H), 2.78-2.70 (m, 2H), 2.66-2.57 (m, 1H), 2.25-2.10 (m, 3H), 2.08-1.98 (m, 1H), 1.96-1.85 (m, 1H), 1.72-1.61 (m, 2H) | 1.577 [630.2] |
| "A51" | 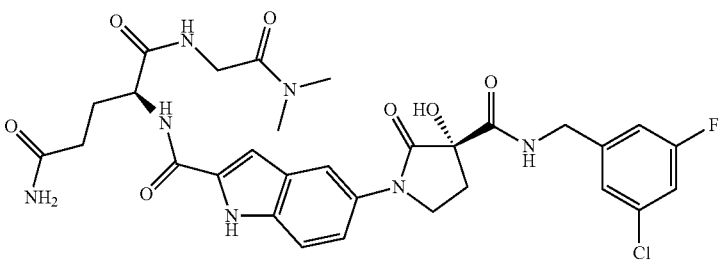<br>(S)-2-({5-[(S)-3-(3-Chloro-5-fluoro-benzylcarbamoyl)-3-hydroxy-2-oxo-pyrrolidin-1-yl]-1H-indole-2-carbonyl}-amino)-pentanedioic acid 5-amide 1-dimethylcarbamoylmethyl-amide | 500 MHz: 11.66-11.59 (m, 1H), 8.72-8.62 (m, 2H), 7.92 (t, J = 5.2, 1H), 7.83-7.78 (m, 1H), 7.59-7.52 (m, 1H), 7.44 (d, J = 8.9, 1H), 7.34-7.28 (m, 1H), 7.28-7.20 (m, 3H), 7.15-7.09 (m, 1H), 6.78 (s, 1H), 6.69 (s, 1H), 4.54-4.46 (m, 1H), 4.41 (dd, J = 15.7, 6.8, 1H), 4.27 (dd, J = 15.8, 6.0, 1H), 4.01-3.87 (m, 4H), 2.94 (s, 3H), 2.83 (s, 3H), 2.66-2.57 (m, 1H), 2.26-2.20 (m, 2H), 2.18-2.11 (m, 1H), 2.11-2.03 (m, 1H), 1.97-1.86 (m, 1H) | 1.868 [658.2] |

| No. | Structure/name | ¹H NMR (400 or 500 MHz, DMSO-d₆) δ [ppm] | LC-MS; rt; [M + H⁺] |
|---|---|---|---|
| "A52" | 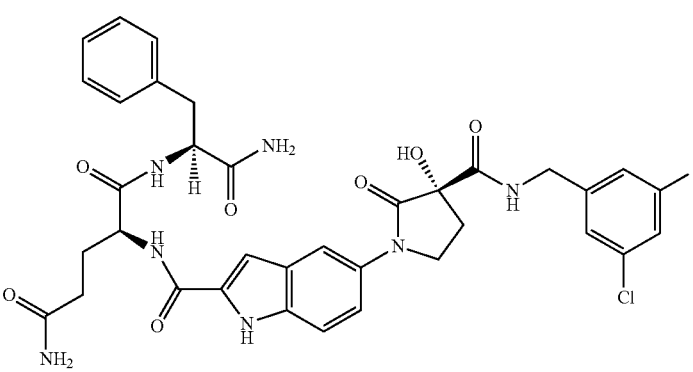<br>(S)-2-({5-[(S)-3-(3-Chloro-5-fluoro-benzylcarbamoyl)-3-hydroxy-2-oxo-pyrrolidin-1-yl]-1H-indole-2-carbonyl}-amino)-pentanedioic acid 5-amide 1-[((S)-1-carbamoyl-2-phenyl-ethyl)-amide] | 500 MHz: 11.72-11.59 (m, 1H), 8.72-8.65 (m, 1H), 8.62 (t, J = 7.4, 1H), 8.21-7.91 (m, 1H), 7.81 (dd, J = 7.9, 2.0, 1H), 7.56 (dd, J = 8.8, 2.0, 1H), 7.45 (dd, J = 8.9, 2.4, 1H), 7.39-7.33 (m, 1H), 7.31-7.04 (m, 11H), 6.83-6.73 (m, 1H), 6.71-6.64 (m, 1H), 4.49-4.33 (m, 3H), 4.27 (dd, J = 15.8, 6.0, 1H), 3.97-3.85 (m, 2H), 3.11-2.98 (m, 1H), 2.88-2.76 (m, 1H), 2.67-2.58 (m, 1H), 2.19-2.10 (m, 2H), 2.07-1.71 (m, 3H) | 1.974 [720.2] |
| "A53" | 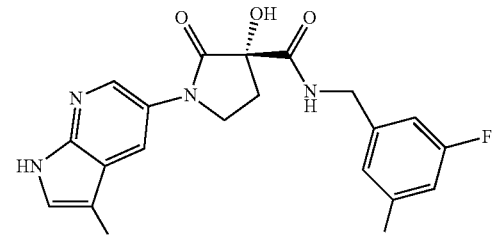<br>(S)-1-(3-Fluoro-1H-pyrrolo[2,3-b]pyridin-5-yl)-3-hydroxy-2-oxo-pyrrolidine-3-carboxylic acid 3-chloro-5-fluoro-benzylamide | 500 MHz: 11.54 (s, 1H), 8.74-8.70 (m, 1H), 8.59 (d, J = 2.4, 1H), 8.21 (d, J = 2.4, 1H), 7.53-7.50 (m, 1H), 7.29-7.25 (m, 1H), 7.23-7.22 (m, 1H), 7.15-7.10 (m, 1H), 6.78 (s, 1H), 4.41 (dd, J = 15.7, 6.7, 1H), 4.27 (dd, J = 15.7, 6.0, 1H), 3.98-3.92 (m, 2H), 2.68-2.61 (m, 1H), 2.22-2.14 (m, 1H) | 2.028 [421.0] |
| "A54" | 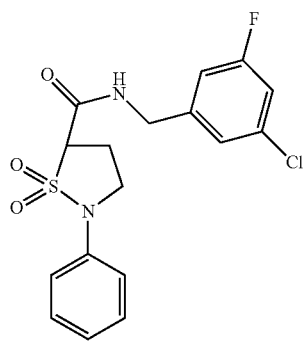<br>1,1-Dioxo-2-phenyl-1λ6-isothiazolidine-5-carboxylic acid 3-chloro-5-fluoro-benzylamide | | |

-continued

| No. | Structure/name | ¹H NMR (400 or 500 MHz, DMSO-d₆) δ [ppm] | LC-MS; rt; [M + H⁺] |
|---|---|---|---|
| "A55" | 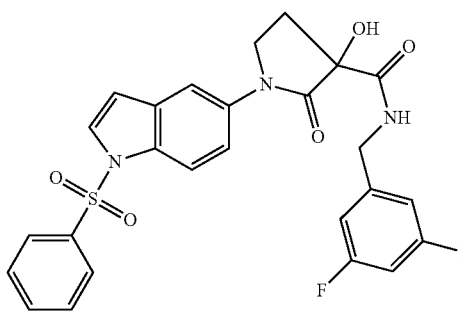<br>1-(1-Benzenesulfonyl-1H-indol-5-yl)-3-hydroxy-2-oxo-pyrrolidine-3-carboxylic acid 3,5-difluoro-benzylamide | 400 MHz: 8.70 (t, 1H), 8.01-7.92 (m, 2H), 7.87 (d, J = 2.1, 1H), 7.83 (d, J = 3.6, 1H), 7.77-7.65 (m, 2H), 7.64-7.53 (m, 2H), 7.06 (tt, J = 9.3, 2.4, 1H), 7.02-6.94 (m, 1H), 6.88 (dd, J = 3.7, 0.7, 1H), 6.75 (s, 1H), 4.49-4.33 (m, 1H), 4.33-4.18 (m, 1H), 3.88 (t, J = 6.8, 2H), 2.66-2.55 (m, 1H), 2.22-2.05 (m, 1H) | 2.377 [526.1] |
| "A56" | 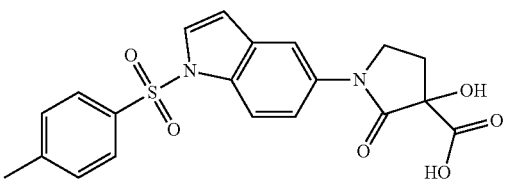<br>3-Hydroxy-2-oxo-1-[1-(toluene-4-sulfonyl)-1H-indol-5-yl]-pyrrolidine-3-carboxylic acid | 400 MHz: 7.92 (d, J = 9.1 Hz, 1H), 7.85 (d, J = 2.0 Hz, 1H), 7.83 (d, J = 8.4 Hz, 2H), 7.77 (d, J = 3.7 Hz, 1H), 7.70 (dd, J = 9.1, 2.1 Hz, 1H), 7.36 (d, J = 8.1 Hz, 2H), 6.85 (d, J = 3.5 Hz, 1H), 3.89 (q, J = 8.5 Hz, 1H), 3.72 (t, J = 8.5 Hz, 1H), 3.49-3.39 (m, 1H), 2.41 (dd, J = 12.1, 7.0 Hz, 1H), 2.30 (s, 3H), 2.00 (dt, J = 12.1, 9.1 Hz, 1H) | 2.099 [415.0] |
| "A57" | 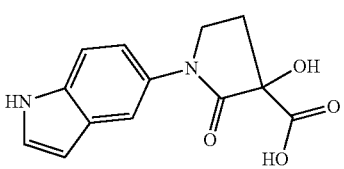<br>3-Hydroxy-1-(1H-indol-5-yl)-2-oxo-pyrrolidine-3-carboxylic acid | | |
| "A58" | 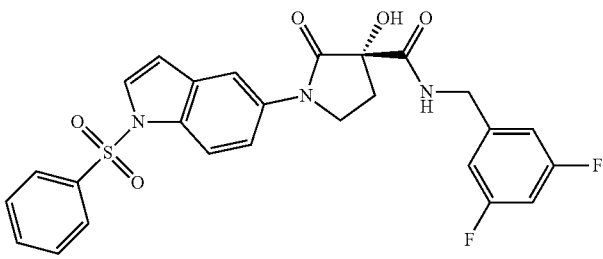<br>(S)-1-(1-Benzenesulfonyl-1H-indol-5-yl)-3-hydroxy-2-oxo-pyrrolidine-3-carboxylic acid 3,5-difluoro-benzylamide | 500 MHz: 8.67 (t, J = 6.4, 1H), 7.98-7.92 (m, 3H), 7.86 (d, J = 2.2, 1H), 7.82 (d, J = 3.7, 1H), 7.75-7.65 (m, 2H), 7.61-7.55 (m, 2H), 7.05 (tt, J = 9.3, 2.4, 1H), 7.01-6.93 (m, 2H), 6.89-6.84 (m, 1H), 6.72 (s, 1H), 4.39 (dd, J = 15.8, 6.8, 1H), 4.25 (dd, J = 15.8, 6.0, 1H), 3.90-3.83 (m, 2H), 2.65-2.54 (m, 1H), 2.17-2.09 (m, 1H) | 2.376 [526.1] |

| No. | Structure/name | ¹H NMR (400 or 500 MHz, DMSO-d₆) δ [ppm] | LC-MS; rt; [M + H⁺] |
|---|---|---|---|
| "A59" | 2-(1H-Indol-5-yl)-1,1-dioxo-1l6-isothiazolidine-5-carboxylic acid 3,5-difluoro-benzylamide | | |
| "A60" | 1-(4-Difluoromethyl-phenyl)-3-hydroxy-2-oxo-pyrrolidine-3-carboxylic acid 3-chloro-5-fluoro-benzylamide | | |
| "A61" | 1-(6-Difluoromethyl-pyridin-3-yl)-3-hydroxy-2-oxo-pyrrolidine-3-carboxylic acid 3-chloro-5-fluoro-benzylamide | | |
| "A62" | (S)-1-(2,3-Dichloro-1H-pyrrolo[2,3-b]pyridin-5-yl)-3-hydroxy-2-oxo-pyrrolidine-3-carboxylic acid 3-chloro-5-fluoro-benzylamide | | |

| No. | Structure/name | ¹H NMR (400 or 500 MHz, DMSO-d$_6$) δ [ppm] | LC-MS; rt; [M + H⁺] |
|---|---|---|---|
| "A63" | 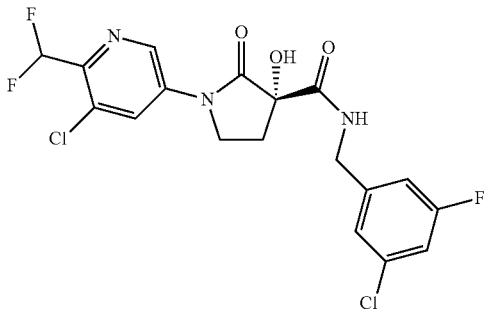<br>(S)-1-(5-Chloro-6-difluoromethyl-pyridin-3-yl)-3-hydroxy-2-oxo-pyrrolidine-3-carboxylic acid 3-chloro-5-fluoro-benzylamide | 400 MHz:<br>9.01 (d, J = 2.20 Hz, 1H), 8.82 (t, J = 6.32 Hz, 1H), 8.47 (d, J = 2.08 Hz, 1H), 7.29-7.03 (m, 4H), 6.95-0.00 (m, 1H), 4.40-4.22 (m, 2H), 4.02-3.92 (m, 2H), 2.67-2.60 (m, 1H), 2.23-2.15 (m, 1H) | 4.44 min<br>[450.0]* |
| "A65" | 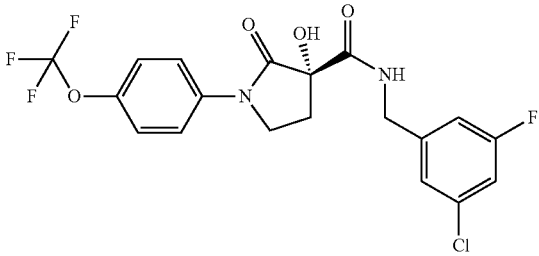<br>(S)-3-Hydroxy-2-oxo-1-(4-trifluoromethoxy-phenyl)-pyrrolidine-3-carboxylic acid 3-chloro-5-fluoro-benzylamide | 400 MHz:<br>8.77 (t, J = 6.40 Hz, 1H), 7.85-7.81 (m, 2H), 7.42 (d, J = 8.40 Hz, 2H), 7.29-7.26 (m, 1H), 7.20 (s, 1H), 7.11-7.08 (m, 1H), 6.83 (s, 1H), 4.40-4.35 (m, 1H), 4.26-4.21 (m, 1H), 3.87 (t, J = 6.04 Hz, 2H), 2.62-2.55 (m, 1H), 2.17-2.10 (m, 1H) | 6.31 min<br>[445.0]* |
| "A66" | 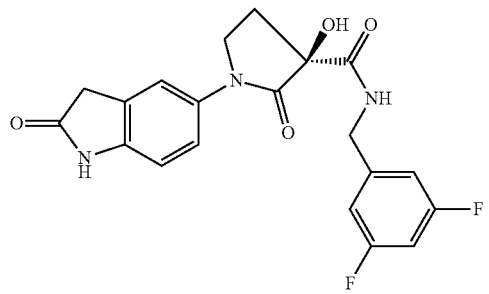<br>(S)-3-Hydroxy-2-oxo-1-(2-oxo-2,3-dihydro-1H-indol-5-yl)-pyrrolidine-3-carboxylic acid 3,5-difluoro-benzylamide | 500 MHz:<br>10.39 (s, 1H), 8.69 (t, J = 6.4, 1H), 7.58 (s, 1H), 7.42 (dd, J = 8.4, 2.2, 1H), 7.07 (tt, J = 9.3, 7.0, 2.3, 1H), 7.02-6.96 (m, 2H), 6.84 (d, J = 8.4, 1H), 6.71 (s, 1H), 4.41 (dd, J = 15.8, 6.8, 1H), 4.26 (dd, J = 15.8, 6.0, 1H), 3.86-3.76 (m, 2H), 3.51 (s, 2H), 2.64-2.56 (m, 1H), 2.15-2.05 (m, 1H) | 1.710<br>[402.1] |

| No. | Structure/name | ¹H NMR (400 or 500 MHz, DMSO-d₆) δ [ppm] | LC-MS; rt; [M + H⁺] |
|---|---|---|---|
| "A67" | 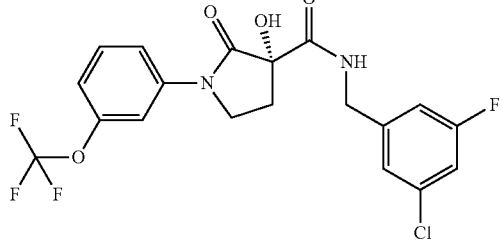<br>(S)-3-Hydroxy-2-oxo-1-(3-trifluoromethoxy-phenyl)-pyrrolidine-3-carboxylic acid 3-chloro-5-fluoro-benzylamide | | |
| "A68" | 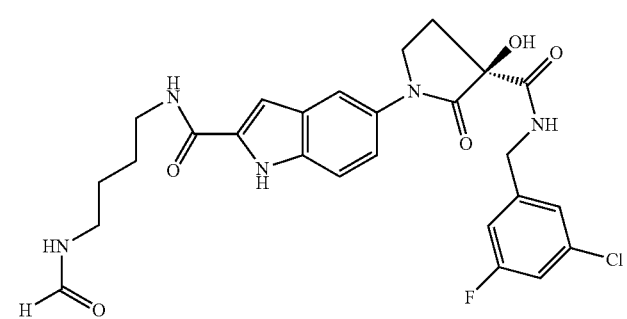<br>5-[(S)-3-(3-Chloro-5-fluoro-benzylcarbamoyl)-3-hydroxy-2-oxo-pyrrolidin-1-yl]-1H-indole-2-carboxylic acid (4-formylamino-butyl)-amide | 500 MHz: 11.61 (s, 1H), 8.71 (t, J = 6.3, 1H), 8.50 (t, J = 5.6, 1H), 8.00 (s, 2H), 7.78 (s, 1H), 7.53 (dd, J = 8.9, 1.7, 1H), 7.42 (d, J = 8.9, 1H), 7.27 (d, J = 8.7, 1H), 7.23 (s, 1H), 7.16-7.04 (m, 2H), 6.72 (s, 1H), 4.40 (dd, J = 15.7, 6.7, 1H), 4.26 (dd, J = 15.7, 5.9, 1H), 3.89 (t, J = 6.7, 2H), 3.30-3.24 (m, 2H), 3.12 (q, J = 6.4, 2H), 2.66-2.55 (m, 1H), 2.20-2.06 (m, 1H), 1.60-1.39 (m, 4H) | 1.935 [544.1] |
| "A69" | 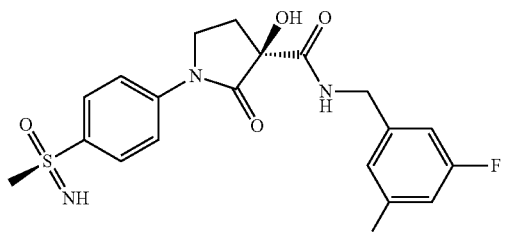<br>(R)$_S$,(S)-3-Hydroxy-1-(4-methanesulfoximinoyl-phenyl)-2-oxo-pyrrolidine-3-carboxylic acid 3-chloro-5-fluoro-benzylamide | | 1.784 [440.0] |
| "A70" | 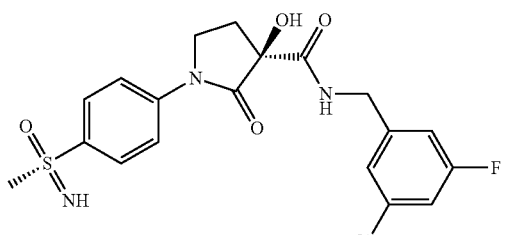<br>(S)$_S$,(S)-3-Hydroxy-1-(4-methanesulfoximinoyl-phenyl)-2-oxo-pyrrolidine-3-carboxylic acid 3-chloro-5-fluoro-benzylamide | | 1.787 [440.0] |

-continued

| No. | Structure/name | $^1$H NMR (400 or 500 MHz, DMSO-$d_6$) δ [ppm] | LC-MS; rt; [M + H$^+$] |
|---|---|---|---|
| "A71" | 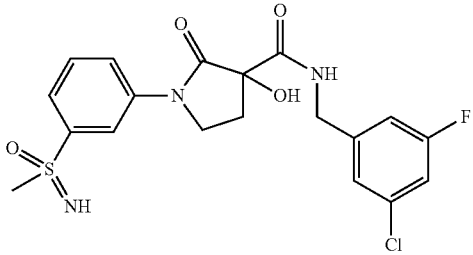<br>3-Hydroxy-1-(3-methanesulfoximinoyl-phenyl)-2-oxo-pyrrolidine-3-carboxylic acid 3-chloro-5-fluoro-benzylamide | | 3.05 min [440.0]* |
| "A72" | 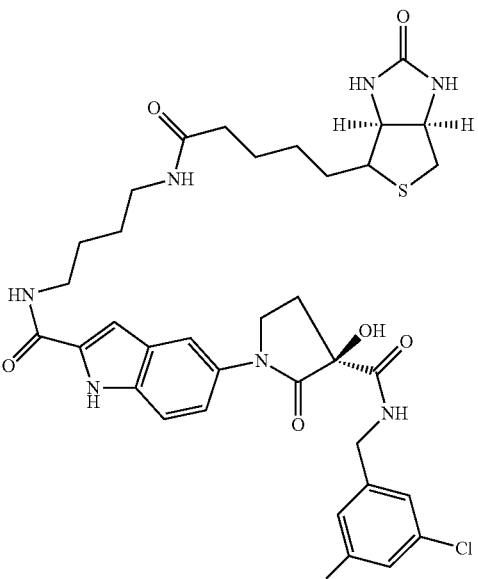<br>5-[(S)-3-(3-Chloro-5-fluoro-benzylcarbamoyl)-3-hydroxy-2-oxo-pyrrolidin-1-yl]-1H-indole-2-carboxylic acid {4-[5-((3aR,6aS)-2-oxo-hexahydro-thieno[3,4-d]imidazol-6-yl)-pentanoylamino]-butyl}-amide | 500 MHz: 11.86 (s, 1H), 8.78 (t, J = 6.4 Hz, 1H), 8.63 (t, J = 5.5 Hz, 1H), 7.80 (t, J = 5.6 Hz, 1H), 7.77 (d, J = 1.8 Hz, 1H), 7.52 (dd, J = 8.9, 2.0 Hz, 1H), 7.42 (d, J = 8.9 Hz, 1H), 7.27 (dt, J = 8.7, 2.1 Hz, 1H), 7.23 (s, 1H), 7.12 (d, J = 9.6 Hz, 1H), 7.09 (s, 1H), 6.92 (s, 1H), 6.42 (s, 1H), 6.35 (s, 1H), 4.40 (dd, J = 15.8, 6.7 Hz, 1H), 4.30-4.23 (m, 2H), 4.13-4.07 (m, 1H), 3.89 (t, J = 6.8 Hz, 2H), 3.30-3.19 (m, 5H), 3.11-3.00 (m, 3H), 2.79 (dd, J = 12.4, 5.1 Hz, 1H), 2.59 (ddd, J = 22.0, 13.2, 8.2 Hz, 2H), 2.14 (dt, J = 12.8, 7.5 Hz, 1H), 2.05 (dd, J = 13.5, 6.1 Hz, 2H), 1.66-1.57 (m, 3H), 1.57-1.38 (m, 7H), 1.37-1.20 (m, 2H). | 1.944 [742.2] |
| "A73" | 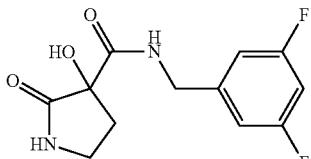<br>3-Hydroxy-2-oxo-pyrrolidine-3-carboxylic acid 3,5-difluoro-benzylamide | 400 MHz: 8.51 (s, 1H), 7.97 (s, 1H), 7.09-7.02 (m, 1H), 7.02-6.99 (m, 1H), 6.98 (d, J = 6.3 Hz, 1H), 6.35 (s, 1H), 4.40 (dd, J = 15.8, 6.0 Hz, 1H), 4.25 (dd, J = 16.0, 5.2 Hz, 1H), 3.24 (t, J = 6.6 Hz, 2H), 2.56-2.52 (m, 1H), 2.01 (dt, J = 13.1, 7.2 Hz, 1H) | 1.461 [271.0] |

| No. | Structure/name | ¹H NMR (400 or 500 MHz, DMSO-d₆) δ [ppm] | LC-MS; rt; [M + H⁺] |
|---|---|---|---|
| "A74" | 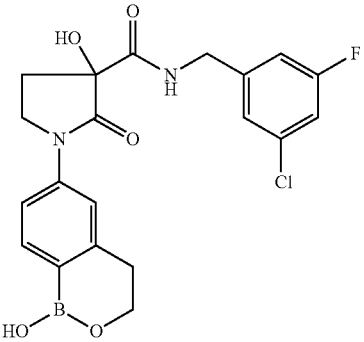<br>3-Hydroxy-1-(1-hydroxy-3,4-dihydro-1H-benzo[c][1,2]oxaborinin-6-yl)-2-oxo-pyrrolidine-3-carboxylic acid 3-chloro-5-fluoro-benzylamide | 400 MHz: 8.73 (t, J = 6.40 Hz, 1H), 8.41 (s, 1H), 7.69 (d, J = 8.00 Hz, 1H), 7.60-7.57 (m, 1H), 7.54 (s, 1H), 7.28-7.25 (m, 1H), 7.20 (s, 1H), 7.09 (d, J = 9.20 Hz, 1H), 6.77 (s, 1H), 4.39-4.35 (m, 1H), 4.26-4.21 (m, 1H), 4.10-4.04 (m, 2H), 3.88-3.84 (m, 2H), 2.86 (t, J = 5.60 Hz, 2H), 2.59-2.56 (m, 1H), 2.16-2.08 (m, 1H) | 4.91 min [431.0]* |
| "A76" | 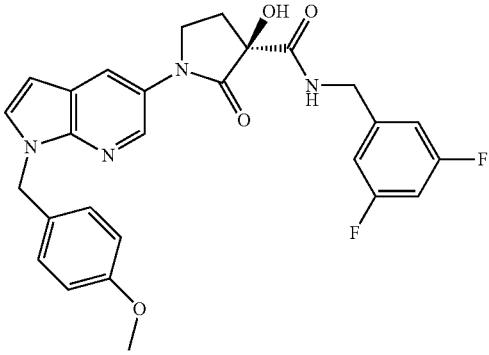<br>(S)-3-Hydroxy-1-[1-(4-methoxy-benzyl)-1H-pyrrolo[2,3-b]pyridin-5-yl]-2-oxo-pyrrolidine-3-carboxylic acid 3,5-difluoro-benzylamide | | 2.260 min [507.1] |
| "A77" | 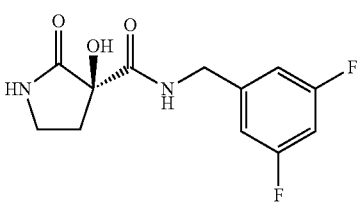<br>(S)-3-Hydroxy-2-oxo-pyrrolidine-3-carboxylic acid 3,5-difluoro-benzylamide | | 1.444 min [271.0] |
| "A78" | 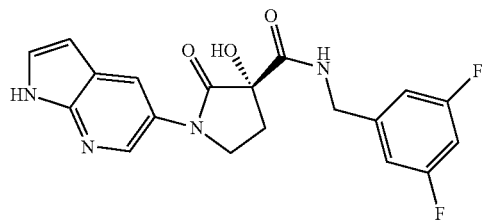<br>(S)-3-Hydroxy-2-oxo-1-(1H-pyrrolo[2,3-b]pyridin-5-yl)-pyrrolidine-3-carboxylic acid 3,5-difluoro-benzylamide | 500 MHz: 11.69 (s, 1H), 8.71 (t, J = 6.4, 1H), 8.50 (d, J = 2.4, 1H), 8.21-8.13 (m, 1H), 7.52 (dd, J = 3.4, 2.6, 1H), 7.07 (tt, J = 9.3, 2.4, 1H), 7.04-6.98 (m, 2H), 6.76 (s, 1H), 6.49 (dd, J = 3.4, 1.8, 1H), 4.43 (dd, J = 15.8, 6.8, 1H), 4.29 (dd, J = 15.8, 6.0, 1H), 3.97-3.90 (m, 2H), 2.70-2.62 (m, 1H), 2.23-2.15 (m, 1H) | 1.782 min [387.1] |

-continued

| No. | Structure/name | ¹H NMR (400 or 500 MHz, DMSO-d₆) δ [ppm] | LC-MS; rt; [M + H⁺] |
|---|---|---|---|
| "A79" | 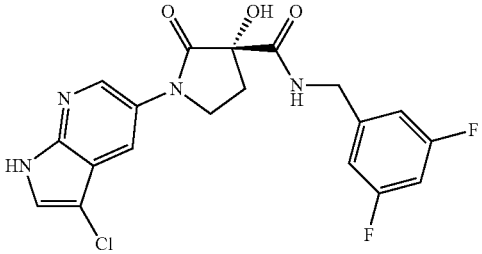<br>(S)-1-(3-Chloro-1H-pyrrolo[2,3-b]pyridin-5-yl)-3-hydroxy-2-oxo-pyrrolidine-3-carboxylic acid 3,5-difluoro-benzylamide | 500 MHz: 12.05 (s, 1H), 8.72 (t, J = 6.4, 1H), 8.58 (d, J = 2.4, 1H), 8.17 (d, J = 2.4, 1H), 7.72 (s, 1H), 7.13-6.92 (m, 3H), 6.78 (s, 1H), 4.42 (dd, J = 15.8, 6.8, 1H), 4.28 (dd, J = 15.8, 6.1, 1H), 4.06-3.91 (m, 2H), 2.70-2.58 (m, 1H), 2.27-2.13 (m, 1H) | 1.981 [421.0] |
| "A80" | 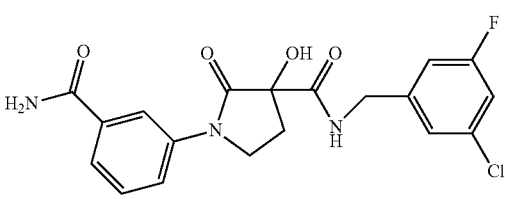<br>1-(3-Carbamoyl-phenyl)-3-hydroxy-2-oxo-pyrrolidine-3-carboxylic acid 3-chloro-5-fluoro-benzylamide | | 1.824 [406.0] |
| "A81" | 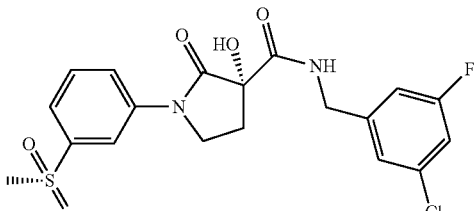<br>(S)$_S$,(S)-3-Hydroxy-1-(3-methanesulfoximinoyl-phenyl)-2-oxo-pyrrolidine-3-carboxylic acid 3-chloro-5-fluoro-benzylamide | | 1.793 [440.0] |
| "A82" | 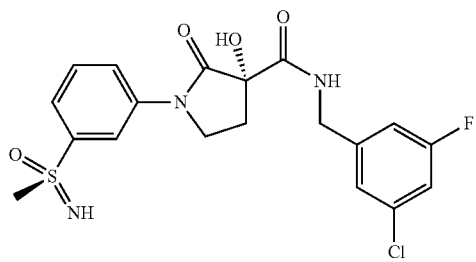<br>(R)$_S$,(S)-3-Hydroxy-1-(3-methanesulfoximinoyl-phenyl)-2-oxo-pyrrolidine-3-carboxylic acid 3-chloro-5-fluoro-benzylamide | | 1.798 [440.0] |

| No. | Structure/name | ¹H NMR (400 or 500 MHz, DMSO-d₆) δ [ppm] | LC-MS; rt; [M + H⁺] |
|---|---|---|---|
| "A83" | 6-[3-(3-Chloro-5-fluoro-benzylcarbamoyl)-3-hydroxy-2-oxo-pyrrolidin-1-yl]-quinoline-2-carboxylic acid amide | | 3.5 min [457.0]* |
| "A85" | 5-[(R)-3-(3,5-Difluoro-benzylcarbamoyl)-3-hydroxy-2-oxo-pyrrolidin-1-yl]-1H-indole-2-carboxylic acid ethyl ester | | 2.117 min [458.1] |
| "A86" | 5-[(S)-3-(3,5-Difluoro-benzylcarbamoyl)-3-hydroxy-2-oxo-pyrrolidin-1-yl]-1H-indole-2-carboxylic acid amide | 400 MHz: 11.57 (s, 1H), 8.68 (t, J = 6.3 Hz, 1H), 7.96 (s, 1H), 7.78 (s, 1H), 7.55 (d, J = 8.9 Hz, 1H), 7.43 (d, J = 8.9 Hz, 1H), 7.35 (s, 1H), 7.13 (s, 1H), 7.11-6.96 (m, 3H), 6.70 (s, 1H), 4.42 (dd, J = 15.8, 6.6 Hz, 1H), 4.28 (dd, J = 15.8, 5.9 Hz, 1H), 3.90 (t, J = 6.7 Hz, 2H), 2.73-2.58 (m, 1H), 2.22-2.07 (m, 1H) | 1.753 min [429.1] |
| "A87" | (3S,4R)-N-[(3-chloro-5-fluoro-phenyl)methyl]-3,4-dihydroxy-2-oxo-1-phenyl-pyrrolidine-3-carboxamide | 400 MHz: 8.77 (t, J = 6.40 Hz, 1H), 7.68 (d, J = 8.72 Hz, 2H), 7.40 (t, J = 8.48 Hz, 2H), 7.29-7.25 (m, 1H), 7.19-7.15 (m, 2H), 7.09 (d, J = 9.52 Hz, 1H), 6.50 (brs, 1H), 5.75-5.79 (brs, 1H), 4.38-4.24 (m, 3H), 4.16-4.12 (m, 1H), 3.60 (dd, J = 9.82, 2.96 Hz, 1H) | 3.92 min [379.0]* |

-continued

| No. | Structure/name | ¹H NMR (400 or 500 MHz, DMSO-d₆) δ [ppm] | LC-MS; rt; [M + H⁺] |
|---|---|---|---|
| "A88" | 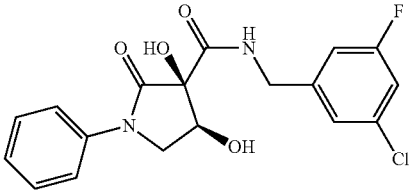<br>(3R,4S)-N-[(3-chloro-5-fluoro-phenyl)methyl]-3,4-dihydroxy-2-oxo-1-phenyl-pyrrolidine-3-carboxamide | 400 MHz: 8.77 (t, J = 6.40 Hz, 1H), 7.68 (d, J = 8.72 Hz, 2H), 7.40 (t, J = 8.48 Hz, 2H), 7.29-7.25 (m, 1H), 7.19-7.15 (m, 2H), 7.09 (d, J = 9.52 Hz, 1H), 6.50 (brs, 1H), 5.79 (brs, 1H), 4.38-4.24 (m, 3H), 4.16-4.12 (m, 1H), 3.60 (dd, J = 9.82, 2.96 Hz, 1H) | 3.92 min [379.0]* |
| "A89" | 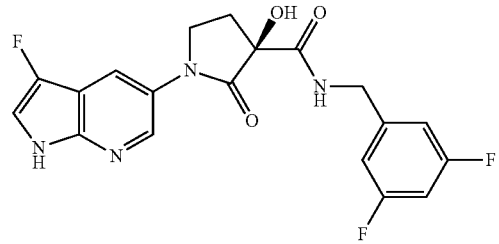<br>(S)-1-(3-Fluoro-1H-pyrrolo[2,3-b]pyridin-5-yl)-3-hydroxy-2-oxo-pyrrolidine-3-carboxylic acid 3,5-difluoro-benzylamide | 400 MHz: 11.54 (s, 1H), 8.70 (t, J = 6.4 Hz, 1H), 8.59 (d, J = 2.4 Hz, 1H), 8.20 (d, J = 2.3 Hz, 1H), 7.51 (t, J = 2.4 Hz, 1H), 7.09-7.03 (m, 1H), 7.02-6.97 (m, 2H), 6.76 (s, 1H), 4.42 (dd, J = 15.8, 6.8 Hz, 1H), 4.28 (dd, J = 15.9, 6.1 Hz, 1H), 3.95 (t, J = 6.8 Hz, 2H), 2.63 (t, J = 6.2 Hz, 1H), 2.18 (dt, J = 12.8, 7.4 Hz, 1H). | 1.888 min [404.9] |
| "A90" | (S)-1-(2-Bromo-1H-indol-5-yl)-3-hydroxy-2-oxo-pyrrolidine-3-carboxylic acid 3-chloro-5-fluoro-benzylamide | | |
| "A91" | (R)-1-(2-Bromo-1H-indol-5-yl)-3-hydroxy-2-oxo-pyrrolidine-3-carboxylic acid 3-chloro-5-fluoro-benzylamide | | |
| "A92" | 5-[(R)-3-(3-Chloro-5-fluoro-benzylcarbamoyl)-3-hydroxy-2-oxo-pyrrolidin-1-yl]-1H-indole-2-carboxylic acid (4-amino-butyl)-amide | | |

TABLE 1

Inhibition of MetAP-2
IC₅₀ of compounds according to the invention

| Compound No. | IC₅₀ enzyme [μM] | Compound No. | IC₅₀ enzyme [μM] |
|---|---|---|---|
| "A1" | 0.13 | "A27" | 0.089 |
| "A2" | 0.81 | "A28" | 0.14 |
| "A3" | 0.18 | "A29" | 0.18 |
| "A4" | 0.52 | "A30" | 0.058 |
| "A5" | 0.096 | "A31" | 6.3 |
| "A6" | 0.043 | "A32" | 5.2 |
| "A7" | 0.48 | "A33" | 0.055 |
| "A8" | 0.07 | "A34" | 0.07 |
| "A9" | 0.051 | "A35" | 0.039 |
| "A10" | 0.078 | "A36" | |
| "A11" | 0.083 | "A37" | |
| "A12" | | "A38" | 0.21 |
| "A13" | 0.14 | "A39" | 0.073 |
| "A14" | | "A40" | 0.034 |
| "A15" | 0.42 | "A41" | 0.22 |
| "A16" | 0.4 | "A42" | 0.28 |
| "A17" | 0.19 | "A43" | 0.84 |
| "A18" | 0.17 | "A44" | 9.1 |
| "A19" | 4.6 | "A46" | 0.24 |
| "A20" | 1 | "A47" | 0.27 |
| "A21" | 0.22 | "A48" | |
| "A22" | 0.15 | "A49" | 5.5 |
| "A23" | 7 | "A50" | 0.039 |
| "A24" | 3.5 | "A51" | 0.079 |
| "A25" | 0.41 | "A52" | 0.075 |
| "A26" | 0.5 | "A53" | 0.1 |

TABLE 1-continued

Inhibition of MetAP-2
IC$_{50}$ of compounds according to the invention

| Compound No. | IC$_{50}$ enzyme [μM] |
|---|---|
| "A54" | |
| "A55" | 0.41 |
| "A56" | |
| "A57" | |
| "A58" | 0.16 |
| "A59" | |
| "A60" | 0.13 |
| "A61" | 0.49 |
| "A62" | 0.37 |
| "A63" | 0.43 |
| "A64" | 0.36 |
| "A65" | 0.13 |
| "A66" | 0.1 |
| "A67" | 0.096 |
| "A68" | 0.068 |
| "A69" | 0.11 |
| "A70" | 0.085 |
| "A71" | 0.62 |
| "A72" | 0.067 |
| "A73" | 2.3 |
| "A74" | 0.12 |
| "A75" | 0.092 |
| "A76" | 0.15 |
| "A77" | 0.79 |
| "A78" | 0.091 |
| "A79" | 0.15 |
| "A80" | 0.16 |
| "A81" | 0.25 |
| "A82" | 0.29 |
| "A83" | 0.17 |
| "A85" | 2.8 |
| "A86" | 0.049 |
| "A87" | 0.063 |
| "A89" | 0.11 |

TABLE 2

HUVEC
IC$_{50}$ of compounds according to the invention

| Compound No. | IC$_{50}$ HUVEC [μM] |
|---|---|
| "A1" | 1 |
| "A2" | 7 |
| "A3" | 0.73 |
| "A4" | 11 |
| "A5" | 0.19 |
| "A6" | 0.03 |
| "A7" | 30 |
| "A8" | 0.017 |
| "A9" | 0.014 |
| "A10" | 3.8 |
| "A11" | 0.024 |
| "A12" | 3.3 |
| "A13" | 2.5 |
| "A14" | |
| "A15" | 5.2 |
| "A16" | 3.5 |
| "A17" | 1.1 |
| "A18" | 0.18 |
| "A19" | 0.18 |
| "A20" | |
| "A21" | 4.2 |
| "A22" | 0.13 |
| "A23" | |
| "A24" | |
| "A25" | 1.3 |
| "A26" | 11 |
| "A27" | 0.48 |
| "A28" | 0.53 |
| "A29" | 1.5 |
| "A30" | |
| "A31" | |
| "A32" | |
| "A33" | 0.0054 |
| "A34" | 0.0067 |
| "A35" | 0.051 |
| "A36" | |
| "A37" | |
| "A38" | |
| "A39" | 3.1 |
| "A40" | 0.2 |
| "A41" | 0.26 |
| "A42" | 1.3 |
| "A43" | 0.82 |
| "A44" | |
| "A46" | 0.045 |
| "A47" | 0.04 |
| "A48" | |
| "A49" | |
| "A50" | 3.5 |
| "A51" | 8.1 |
| "A52" | 4.4 |
| "A53" | 0.039 |
| "A54" | |
| "A55" | |
| "A56" | |
| "A57" | |
| "A58" | |
| "A59" | |
| "A60" | 1.8 |
| "A61" | |
| "A62" | 0.18 |
| "A63" | |
| "A64" | 6.1 |
| "A65" | 1.5 |
| "A66" | 0.076 |
| "A67" | 0.29 |
| "A68" | 0.11 |
| "A69" | 0.3 |
| "A70" | 0.7 |
| "A71" | 1.4 |
| "A72" | |
| "A73" | |
| "A74" | 0.014 |
| "A75" | 0.042 |
| "A76" | 0.26 |
| "A77" | |
| "A78" | 0.035 |
| "A79" | 0.0065 |
| "A80" | 0.24 |
| "A81" | 0.54 |
| "A82" | 0.31 |
| "A83" | 0.5 |
| "A85" | |
| "A86" | 0.071 |
| "A87" | 2.3 |
| "A89" | 0.032 |

135
Comparative Data

| compound | Solubility [μg/ml] | | |
|---|---|---|---|
| | pH 7.4 | pH 1.2 | pH 5.0 |
| WO 2013/149704 Compound "B8" | 40 | 33 | 70 |

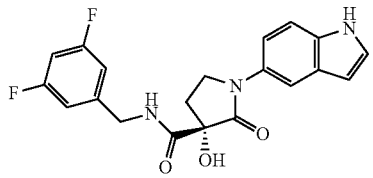 [SMILES: O=C(NCc1cc(F)cc(F)c1)[C@@]1(O)CCN(c2ccc3[nH]ccc3c2)C1=O]

(S)-3-Hydroxy-1-(1H-indol-5-yl)-
2-oxo-pyrrolidin3-3-carboxylic
acid-3,5-difluoro-benzylamide

| | | | |
|---|---|---|---|
| "A75" | 157 | 282 | 276 |
| "A78" | 70 | 850 | 172 |
| "A79" | 142 | 443 | 316 |

Compounds according to the invention such as "A75", "A78" and "A79" show higher solubility in comparison to the prior art compound. Higher solubility results in higher bioavailability when administering the compounds.

The following examples relate to medicaments:

EXAMPLE A: INJECTION VIALS

A solution of 100 g of an active compound according to the invention and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

EXAMPLE B: SUPPOSITORIES

A mixture of 20 g of an active compound according to the invention with 100 g of soya lecithin and 1400 g of cocoa butter is melted, poured into moulds and allowed to cool. Each suppository contains 20 mg of active compound.

EXAMPLE C: SOLUTION

A solution is prepared from 1 g of an active compound according to the invention, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D: OINTMENT 500 mg of an active compound according to the invention are mixed with 99.5 g of Vaseline under aseptic conditions.

EXAMPLE E: TABLETS

A mixture of 1 kg of active compound according to the invention, 4 kg of lactose, 1.2 kg of potato starch, 0.2 kg of talc and 0.1 kg of magnesium stearate is pressed in a conventional manner to give tablets in such a way that each tablet contains 10 mg of active compound.

136

EXAMPLE F: DRAGEES

Tablets are pressed analogously to Example E and subsequently coated in a conventional manner with a coating of sucrose, potato starch, talc, tragacanth and dye.

EXAMPLE G: CAPSULES 2 kg of active compound according to the invention are introduced into hard gelatine capsules in a conventional manner in such a way that each capsule contains 20 mg of the active compound.

EXAMPLE H: AMPOULES

A solution of 1 kg of active compound according to the invention in 60 l of bidistilled water is sterile filtered, transferred into ampoules, lyophilised under sterile conditions and sealed under sterile conditions. Each ampoule contains 10 mg of active compound.

The invention claimed is:
1. A compound of the formula

"A78"

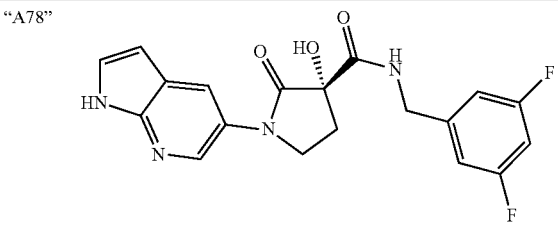

(S)-3-Hydroxy-2-oxo-1-(1H-pyrrolo[2,3-b]pyridin-5-yl)-
pyrrolidine-3-carboxylic acid 3,5-difluoro-benzylamide

"A79"

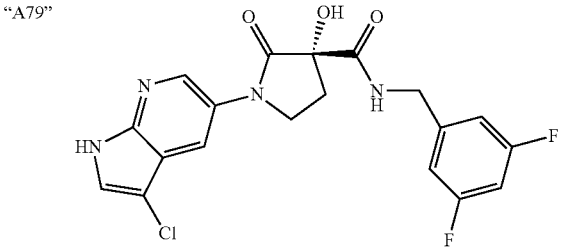

(S)-1-(3-Chloro-1H-pyrrolo[2,3-b]pyridin-5-yl)-3-hydroxy-2-
oxo-pyrrolidine-3-carboxylic acid 3,5-difluoro-benzylamide or pharmaceutically usable salts, tautomers or stereoisomers thereof, including mixtures thereof in all ratios.

2. The compound according to claim 1 of the formula

"A78"

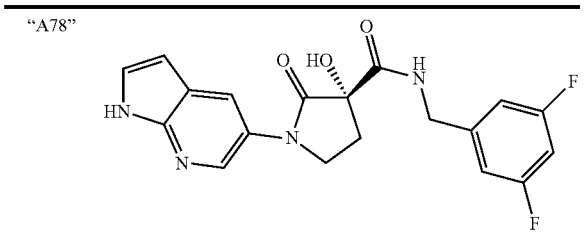

(S)-3-Hydroxy-2-oxo-1-(1H-pyrrolo[2,3-b]pyridin-5-yl)-
pyrrolidine-3-carboxylic acid 3,5-difluoro-benzylamide or pharmaceutically usable salts, tautomers or stereoisomers thereof, including mixtures thereof in all ratios.

3. The compound according to claim 1 of the formula

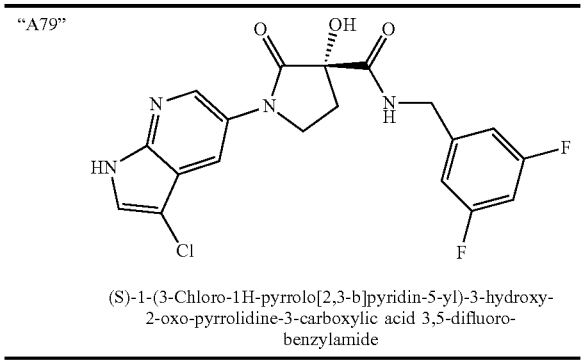

"A79"

(S)-1-(3-Chloro-1H-pyrrolo[2,3-b]pyridin-5-yl)-3-hydroxy-2-oxo-pyrrolidine-3-carboxylic acid 3,5-difluoro-benzylamide or pharmaceutically usable salts, tautomers or stereoisomers thereof, including mixtures thereof in all ratios.

4. A pharmaceutical composition comprising at least one compound according to claim 1 and/or pharmaceutically usable salts, tautomers or stereo-isomers thereof, including mixtures thereof in all ratios, and a pharmaceutically acceptable carrier.

5. A method for the treatment of tumours, tumour metastases, proliferative diseases of the mesangial cells, haemangioma, proliferative retinopathy, rheumatoid arthritis, atherosclerotic neovascularisation, psoriasis, ocular neovascularisation, osteoporosis, diabetes and obesity, lymphoid leukaemia, lymphoma, malaria is prostate hypertrophy, comprising administering to a host in need thereof an effective amount of a compound according to claim 1, or pharmaceutically usable salt, tautomer, stereoisomer or mixture thereof.

6. The method according to claim 5, where the tumour disease is of the squamous epithelium, the bladder, the stomach, the kidneys, of head and neck, the esophagus, the cervix, the thyroid, the intestine, the liver, the brain, the prostate, the urogenital tract, the lymphatic system, the stomach, the larynx, the lung, or of the skin, or is monocytic leukaemia, lung adenocarcinoma, small-cell lung carcinoma, pancreatic cancer, glio-blastoma, breast carcinoma, acute myeloid leukaemia, chronic myeloid leukaemia, acute lymphatic leukaemia, chronic lymphatic leukaemia, Hodgkin's lymphoma, or non-Hodgkin's lymphoma.

7. The method according to claim 5, comprising administering a therapeutically effective amount of a compound according to claim 1 in combination with a compound that is 1) an oestrogen receptor modulator, 2) an androgen receptor modulator, 3) a retinoid receptor modulator, 4) a cytotoxic agent, 5) a antiproliferative agent, 6) a prenyl-protein transferase inhibitor, 7) a HMG-CoA reductase inhibitor, 8) a HIV protease inhibitor, 9) a reverse transcriptase inhibitor or 10) an angiogenesis inhibitor.

8. The method according to claim 5, comprising administering a therapeutically effective amount of a compound according to claim 1 in combination with radiotherapy and 1) an oestrogen receptor modulator, 2) an androgen receptor modulator, 3) a retinoid receptor modulator, 4) a cytotoxic agent, 5) an antiproliferative agent, 6) a prenyl-protein transferase inhibitor, 7) an HMG-CoA reductase inhibitor, 8) an HIV protease inhibitor, 9) a reverse transcriptase inhibitor or 10) an angiogenesis inhibitor.

* * * * *